United States Patent
Shin et al.

(10) Patent No.: US 12,065,406 B2
(45) Date of Patent: Aug. 20, 2024

(54) COMPOUND, ORGANIC OPTOELECTRONIC DEVICE AND DISPLAY DEVICE

(71) Applicant: LT MATERIALS CO., LTD., Yongin-Si (KR)

(72) Inventors: Jin-Hwan Shin, Yongin-si (KR); Yong-Woo Kim, Yongin-si (KR); Gwang-Il Dong, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 471 days.

(21) Appl. No.: 17/426,880

(22) PCT Filed: Jan. 30, 2020

(86) PCT No.: PCT/KR2020/001444
§ 371 (c)(1),
(2) Date: Jul. 29, 2021

(87) PCT Pub. No.: WO2020/159266
PCT Pub. Date: Aug. 6, 2020

(65) Prior Publication Data
US 2022/0106332 A1    Apr. 7, 2022

(30) Foreign Application Priority Data
Jan. 30, 2019 (KR) .................. 10-2019-0012105

(51) Int. Cl.
C07D 209/86 (2006.01)
C07D 209/82 (2006.01)
(Continued)

(52) U.S. Cl.
CPC ......... *C07D 209/86* (2013.01); *C07D 209/82* (2013.01); *C07D 405/04* (2013.01); *C07D 405/12* (2013.01); *C07D 409/04* (2013.01); *C07D 409/12* (2013.01); *C07D 519/00* (2013.01); *H10K 50/11* (2023.02); *H10K 50/14* (2023.02); *H10K 85/624* (2023.02);
(Continued)

(58) Field of Classification Search
None
See application file for complete search history.

(56) References Cited

U.S. PATENT DOCUMENTS

2009/0284143 A1    11/2009 Nomura et al.
2010/0237773 A1    9/2010 Nomura et al.
(Continued)

FOREIGN PATENT DOCUMENTS

CN    107936957 A    4/2018
KR    10-2011-0097784 A    8/2011
(Continued)

OTHER PUBLICATIONS

English text machine translation of Kim et al. (WO-2018155826-A1) accessed online from Espacenet; PDF pp. 1-30. (Year: 2018).*
(Continued)

*Primary Examiner* — Katie L. Hammer
(74) *Attorney, Agent, or Firm* — Birch, Stewart, Kolasch & Birch, LLP

(57) ABSTRACT

The present application relates to a compound represented by Chemical Formula 1, an organic optoelectronic diode and a display device.

10 Claims, 3 Drawing Sheets

(51) Int. Cl.
*C07D 405/04* (2006.01)
*C07D 405/12* (2006.01)
*C07D 409/04* (2006.01)
*C07D 409/12* (2006.01)
*C07D 519/00* (2006.01)
*H10K 50/11* (2023.01)
*H10K 50/14* (2023.01)
*H10K 50/15* (2023.01)
*H10K 85/60* (2023.01)

(52) U.S. Cl.
CPC ......... *H10K 85/633* (2023.02); *H10K 85/636* (2023.02); *H10K 85/6572* (2023.02); *H10K 85/6574* (2023.02); *H10K 85/6576* (2023.02); *H10K 50/15* (2023.02)

(56) References Cited

U.S. PATENT DOCUMENTS

2011/0278551 A1 11/2011 Yabunouchi et al.
2012/0248426 A1 10/2012 Kato
2015/0318464 A1 11/2015 Buesing et al.

FOREIGN PATENT DOCUMENTS

| KR | 10-2015-0016325 A | 2/2015 | |
| KR | 10-2015-0088295 A | 7/2015 | |
| KR | 10-2018-0098130 A | 9/2018 | |
| WO | WO-2018155826 A1 * | 8/2018 | ........... C07D 209/82 |

OTHER PUBLICATIONS

International Search Report (PCT/ISA/210) issued in PCT/KR2020/001444, dated Jun. 12, 2020.

* cited by examiner

【FIG. 1】
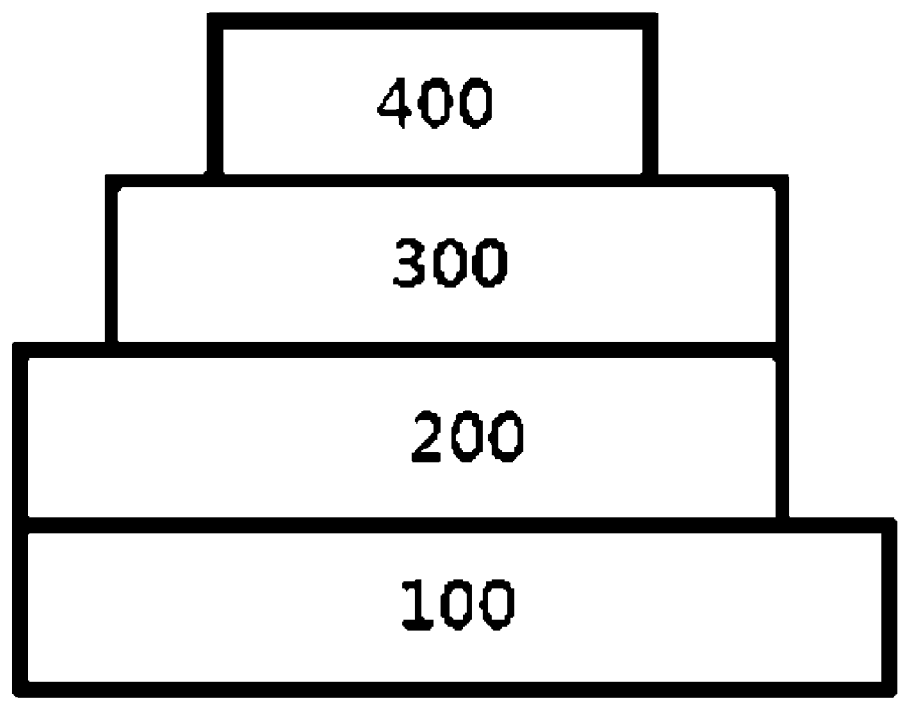

【FIG. 2】
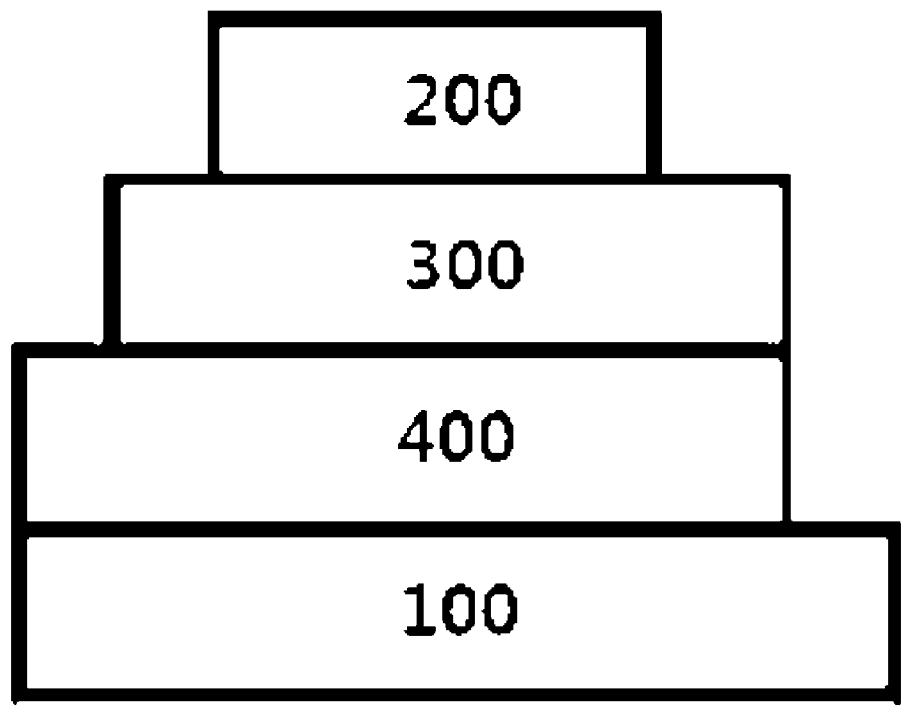

[FIG. 3]
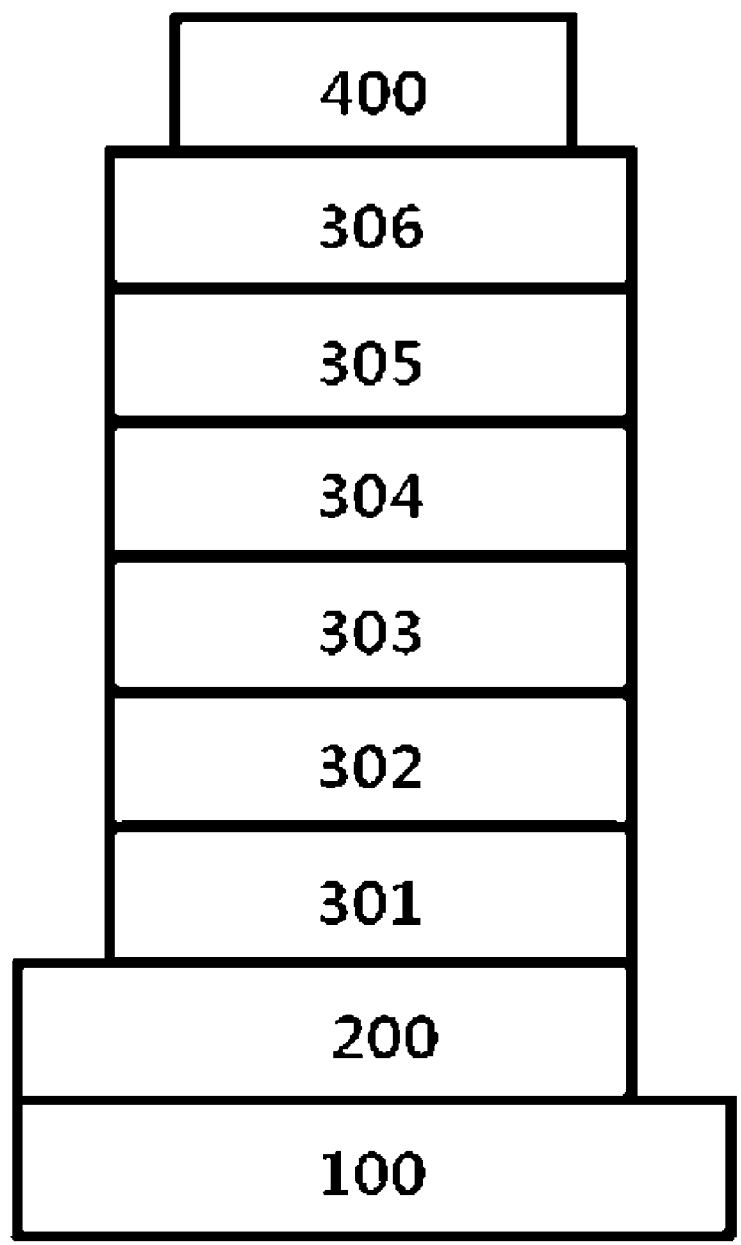

COMPOUND, ORGANIC OPTOELECTRONIC DEVICE AND DISPLAY DEVICE

TECHNICAL FIELD

This application claims priority to and the benefits of Korean Patent Application No. 10-2019-0012105, filed with the Korean Intellectual Property Office on Jan. 30, 2019, the entire contents of which are incorporated herein by reference.

The present application relates to a compound, an organic optoelectronic diode and a display device.

BACKGROUND ART

An organic optoelectronic diode is a device capable of interconverting electrical energy and light energy.

An organic optoelectronic diode may be divided into two types depending on the operating principle. One is an optoelectronic diode in which excitons formed by light energy are separated into electrons and holes and electrical energy is generated while the electrons and the holes are each transferred to different electrodes, and the other one is a light emitting diode generating light energy from electrical energy by supplying a voltage or a current to electrodes.

Examples of the organic optoelectronic diode may include an organic photoelectric diode, an organic light emitting diode, an organic solar cell, an organic photo conductor drum and the like.

Among these, an organic light emitting diode (OLED) has received much attention recently as demands for flat panel display devices have increased. An organic light emitting diode is a device converting electrical energy to light, and performance of an organic light emitting diode is greatly affected by organic materials disposed between electrodes.

An organic light emitting diode has a structure disposing an organic thin film between two electrodes. When a voltage is applied to an organic light emitting diode having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used.

In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting diode.

DISCLOSURE

Technical Problem

One embodiment of the present specification is directed to providing a compound capable of obtaining an organic optoelectronic diode with high efficiency and long lifetime.

Another embodiment of the present specification is directed to providing an organic optoelectronic diode including the compound.

Still another embodiment of the present specification is directed to providing a display device including the organic optoelectronic diode.

Technical Solution

One embodiment of the present application provides a compound represented by the following Chemical Formula 1.

[Chemical Formula 1]

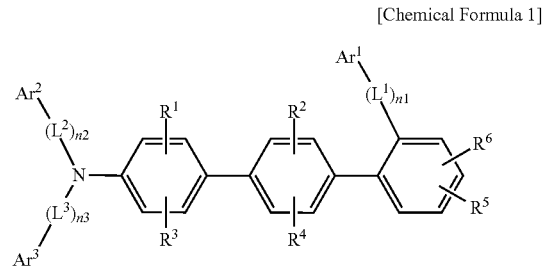

In Chemical Formula 1, $Ar^1$ is a substituted or unsubstituted C2 to C60 heteroaryl group, $Ar^2$ and $Ar^3$ are each independently a substituted or unsubstituted C6 to C60 aryl group, or any one of the following Chemical Formulae 3-1 to 3-4, $L^1$ to $L^3$ are each independently a single bond, a substituted or unsubstituted C6 to C60 arylene group, or a substituted or unsubstituted C2 to C60 heteroarylene group, n1 to n3 are each independently one of integers of 0 to 2, and $R^1$ to $R^6$ are each independently hydrogen, deuterium, a cyano group, a substituted or unsubstituted C1 to C60 alkyl group, or a substituted or unsubstituted C6 to C60 aryl group.

[Chemical Formula 3-1]

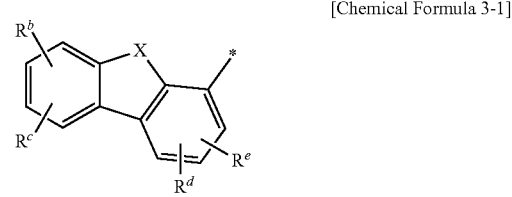

[Chemical Formula 3-2]

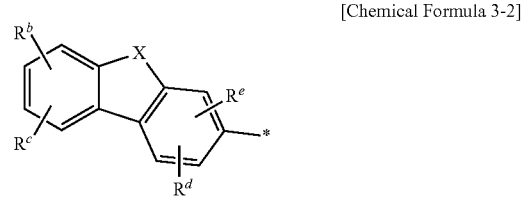

[Chemical Formula 3-3]

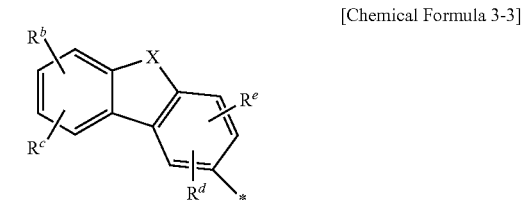

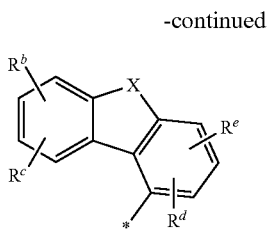

[Chemical Formula 3-4]

In Chemical Formula 3-1 to Chemical Formula 3-4,

X is —O—, —S— or —CR$^x$R$^y$—,

R$^x$ and R$^y$ are each independently hydrogen, deuterium, a cyano group, a substituted or unsubstituted C1 to C60 alkyl group or a C6 to C60 aryl group, or fused to each other to form a ring, and R$^b$ to R$^e$ are each independently hydrogen, deuterium, a cyano group, a substituted or unsubstituted C1 to C60 alkyl group, or a C6 to C60 aryl group.

Advantageous Effects

When using a compound represented by Chemical Formula 1 according to one embodiment of the present application as a material of an organic material layer of an organic optoelectronic diode, hole injection and hole transfer abilities are further strengthened, and an organic optoelectronic diode with high efficiency and long lifetime can be obtained.

The compound represented by Chemical Formula 1 according to one embodiment of the present application has a property of enhancing thin film stability by suppressing material crystallization.

DESCRIPTION OF DRAWINGS

FIG. 1 to FIG. 3 are sectional diagrams each illustrating an organic light emitting diode according to one embodiment of the present specification.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, embodiments of the present disclosure will be described in detail. However, these are for illustrative purposes only, and the present disclosure is not limited thereto, and is only defined by the category of claims to describe later.

In the present specification, "substituted or unsubstituted" means being substituted with one or more substituents selected from the group consisting of deuterium; a halogen group; —CN; a C1 to C60 linear or branched alkyl group; a C2 to C60 linear or branched alkenyl group; a C2 to C60 linear or branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; —SiRR'R"; —P(=O)RR'; a C1 to C20 alkylamine group; a C6 to C60 monocyclic or polycyclic arylamine group; a C2 to C60 monocyclic or polycyclic heteroarylamine group and a substituted or unsubstituted alkoxy group, or being unsubstituted, or being substituted with a substituent bonding two or more of the substituents, or being unsubstituted, or being substituted with a substituent linking two or more substituents selected from among the above-mentioned substituents, or being unsubstituted. In addition, these may further form a ring with adjacent substituents.

For example, the "substituent linking two or more substituents" may include a biphenyl group. In other words, a biphenyl group may be an aryl group, or interpreted as a substituent linking two phenyl groups. The additional substituents may be further substituted. R, R' and R" are the same as or different from each other, and each independently hydrogen; deuterium; —CN; a substituted or unsubstituted C1 to C60 linear or branched alkyl group; a substituted or unsubstituted C3 to C60 monocyclic or polycyclic cycloalkyl group; a substituted or unsubstituted C6 to C60 monocyclic or polycyclic aryl group; or a substituted or unsubstituted C2 to C60 monocyclic or polycyclic heteroaryl group.

According to one embodiment of the present application, the "substituted or unsubstituted" means being substituted with one or more substituents selected from the group consisting of deuterium, a halogen group, —CN, —SiRR'R", —P(=O)RR', a C1 to C20 linear or branched alkyl group, a C6 to C60 monocyclic or polycyclic aryl group and a C2 to C60 monocyclic or polycyclic heteroaryl group, or being unsubstituted, and R, R' and R" are the same as or different from each other and each independently hydrogen; deuterium; —CN; a C1 to C60 alkyl group unsubstituted or substituted with deuterium, a halogen group, —CN, a C1 to C20 alkyl group, a C6 to C60 aryl group and a C2 to C60 heteroaryl group; a C3 to C60 cycloalkyl group unsubstituted or substituted with deuterium, halogen, —CN, a C1 to C20 alkyl group, a C6 to C60 aryl group and a C2 to C60 heteroaryl group; a C6 to C60 aryl group unsubstituted or substituted with deuterium, halogen, —CN, a C1 to C20 alkyl group, a C6 to C60 aryl group and a C2 to C60 heteroaryl group; or a C2 to C60 heteroaryl group unsubstituted or substituted with deuterium, halogen, —CN, a C1 to C20 alkyl group, a C6 to C60 aryl group and a C2 to C60 heteroaryl group.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may include fluorine, chlorine, bromine or iodine.

In the present specification, the alkyl group includes a C1 to C60 linear or branched, and may be further substituted with other substituents. The number of carbon atoms of the alkyl group may be from 1 to 60, specifically from 1 to 40, and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes a C2 to C60 linear or branched, and may be further substituted with other substituents. The number of carbon atoms of the alkenyl group may be from 2 to 60, specifically from 2 to 40, and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes a C2 to C60 linear or branched, and may be further substituted with other substituents. The number of carbon atoms of the alkynyl group may be from 2 to 60, specifically from 2 to 40, and more specifically from 2 to 20.

In the present specification, the cycloalkyl group includes a C3 to C60 monocyclic or polycyclic, and may be further substituted with other substituents. Herein, the polycyclic means a group in which the cycloalkyl group is directly linked to or fused with another cyclic group. Herein, the another cyclic group may be a cycloalkyl group, but may also include other types of cyclic groups such as a heterocycloalkyl group, an aryl group and a heteroaryl group. The number of carbon atoms of the cycloalkyl group may be from 3 to 60, specifically from 3 to 40, and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may include a C1 to C10 alkoxy group, and more specifically, a methoxy group, an ethoxy group, a propoxy group, a butoxy group, a pentoxy group and the like.

In the present specification, the silyl group may be represented by —SiRR'R", and R, R' and R" have the same definitions as above. More specifically, a dimethylsilyl group, a diethylsilyl group, a methylethylsilyl group and the like may be included.

In the present specification, the phosphine oxide group may be represented by —P(=O)RR', and R and R' have the same definitions as above. More specifically, dimethyl phosphine, diethyl phosphine, methylethyl phosphine and the like may be included.

In the present specification, the fluorenyl group means a substituent including various substituents at the number 9 position. Specifically, a concept including a fluorenyl group in which the number 9 position is substituted with two hydrogens, two alkyl groups, two aryl groups or two heteroaryl groups may be used. More specifically, a 9-di-H-fluorenyl group, a 9-di-methyl-fluorenyl group, a 9-di-phenyl-fluorenyl group or the like may be used.

In the present specification, the heterocycloalkyl group includes O, S, Se, N or Si as a heteroatom, includes a C2 to C60 monocyclic or polycyclic, and may be further substituted with other substituents. Herein, the polycyclic means a group in which the heterocycloalkyl group is directly linked to or fused with another cyclic group. Herein, the another cyclic group may be a heterocycloalkyl group, but may also include other types of cyclic groups such as a cycloalkyl group, an aryl group and a heteroaryl group. The number of carbon atoms of the heterocycloalkyl group may be from 2 to 60, specifically from 2 to 40, and more specifically from 3 to 20.

In the present specification, the aryl group includes a C6 to C60 monocyclic or polycyclic, and may be further substituted with other substituents. Herein, the polycyclic means a group in which the aryl group is directly linked to or fused with another cyclic group. Herein, the another cyclic group may be an aryl group, but may also include other types of cyclic groups such as a cycloalkyl group, a heterocycloalkyl group and a heteroaryl group. The aryl group includes a spiro group. The number of carbon atoms of the aryl group may be from 6 to 60, specifically from 6 to 40, and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof and the like, but are not limited thereto.

In the present specification, the spiro group is a group including a spiro structure, and may be from C15 to C60. For example, the spiro group may include a structure in which a 2,3-dihydro-1H-indene group or a cyclohexane group spiro-bonds to a fluorenyl group. Specifically, the spiro group may include any one of the groups of the following structural formulae.

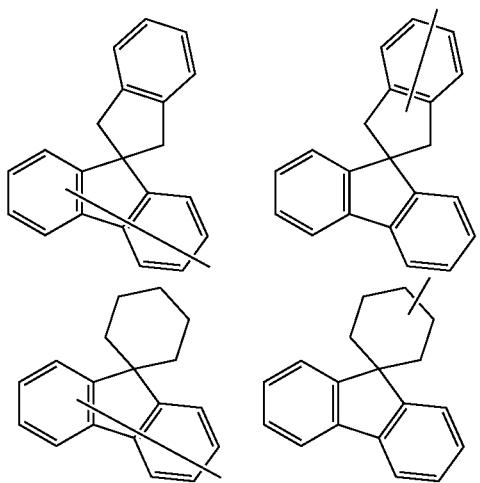

-continued

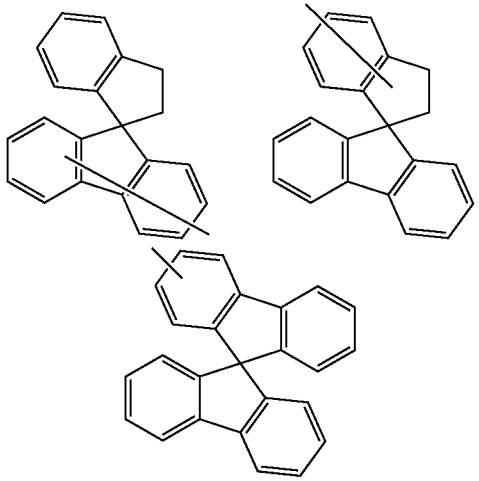

In the present specification, the heteroaryl group includes S, O, Se, N or Si as a heteroatom, includes a C2 to C60 monocyclic or polycyclic, and may be further substituted with other substituents. Herein, the polycyclic means a group in which the heteroaryl group is directly linked to or fused with another cyclic group. Herein, the another cyclic group may be a heteroaryl group, but may also include other types of cyclic groups such as a cycloalkyl group, a heterocycloalkyl group and an aryl group. The number of carbon atoms of the heteroaryl group may be from 2 to 60, specifically from 2 to 40, and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolinyl group, a naphthyridyl group, an acridinyl group, a phenanthridinyl group, an imidazopyridinyl group, diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, 9,10-dihydroacridinyl group, a phenanthrazinyl group, a phenothiathiazinyl group, a phthalazinyl group, a naphthyridinyl group, a phenanthrolinyl group, a benzo[c][1,2,5]thiadiazolyl group, 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH₂; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means an aryl group having two bonding sites, that is, a divalent group. Descriptions on the aryl group provided above may be applied thereto except for each being a divalent group. In addition, the heteroarylene group means a heteroaryl group having two bonding sites, that is, a divalent group. Descriptions on the heteroaryl group provided above may be applied thereto except for each being a divalent group.

In the present specification, hole properties refer to properties capable of forming holes by donating electrons when applying an electric field, and means properties of, by having conducting properties along the HOMO level, facilitating injection of holes forming in an anode to a light emitting layer, migration of holes formed in a light emitting layer to an anode and migration in the light emitting layer.

Substituents having hole properties include a substituted or unsubstituted C6 to C60 aryl group having hole properties, a substituted or unsubstituted C2 to C60 heteroaryl group having hole properties, a substituted or unsubstituted arylamine group, a substituted or unsubstituted heteroarylamine group, or the like.

More specifically, the substituted or unsubstituted C6 to C60 aryl group having hole properties may be a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluorenyl group, a substituted or unsubstituted terphenyl group, a substituted or unsubstituted pyrenyl group, a substituted or unsubstituted perylenyl group, or a combination thereof.

More specifically, the substituted or unsubstituted C2 to C60 heteroaryl group having hole properties is a substituted or unsubstituted carbazolyl group, a substituted or unsubstituted dibenzofuranyl group, a substituted or unsubstituted dibenzothiophenyl group, a substituted or unsubstituted indolecarbazolyl group, or the like.

The aryl group or the heteroaryl group, a substituent bonding to the nitrogen of the substituted or unsubstituted arylamine group and the substituted or unsubstituted heteroarylamine group may be, more specifically, a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

In addition, electron properties refer to properties capable of receiving electrons when applying an electric field, and means properties of, by having conducting properties along the LUMO level, facilitating injection of electrons forming in a cathode to a light emitting layer, migration of electrons formed in a light emitting layer to a cathode and migration in the light emitting layer.

The substituted or unsubstituted C2 to C60 heteroaryl group having electron properties may be a substituted or unsubstituted imidazolyl group, a substituted or unsubstituted tetrazolyl group, a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazoline group, a substituted or unsubstituted benzoxadiazoline group, a substituted or unsubstituted oxatriazolyl group, a substituted or unsubstituted thiophenyl group, a substituted or unsubstituted benzothiophenyl group, a substituted or unsubstituted isothiazoline group, a substituted or unsubstituted benzoisothiazoline group, a substituted or unsubstituted thiazoline group, a substituted or unsubstituted benzothiazoline group, a substituted or unsubstituted pyridazinyl group, a substituted or unsubstituted benzopyridazinyl group, a substituted or unsubstituted pyrazinyl group, a substituted or unsubstituted benzopyrazinyl group, a substituted or unsubstituted phthalazinyl group, a substituted or unsubstituted benzoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

More specifically, the substituted or unsubstituted C2 to C60 heteroaryl group having electron properties may be any one of the following Chemical Formulae X-1 to X-5.

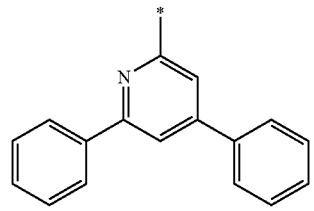

[Chemical Formula X-1]

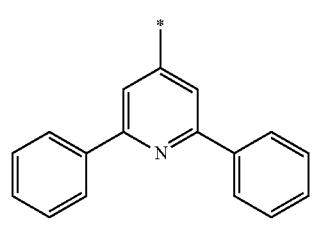

[Chemical Formula X-2]

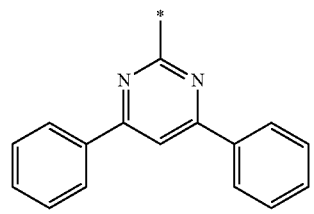

[Chemical Formula X-3]

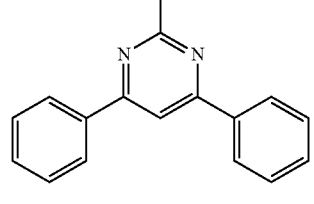

[Chemical Formula X-4]

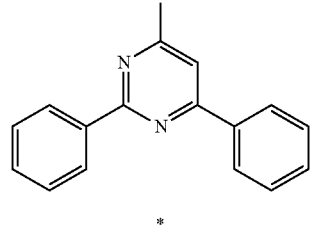

[Chemical Formula X-5]

In one embodiment of the present application, L" may be a direct bond (or a single bond); a substituted or unsubstituted arylene group; or a substituted or unsubstituted heteroarylene group.

In another embodiment, L" may be a direct bond; a substituted or unsubstituted C6 to C60 arylene group; or a substituted or unsubstituted C2 to C60 heteroarylene group.

In another embodiment, L" may be a direct bond; a substituted or unsubstituted C6 to C40 arylene group; or a substituted or unsubstituted C2 to C40 heteroarylene group.

In L", n means a number for distinguishing substituents.

For example, n is an integer of 1 to 3. In other words, L" in the present specification may each be represented by $L^1$, $L^2$ and $L^3$.

Hereinafter, a compound according to one embodiment will be described.

The compound according to one embodiment is represented by the following Chemical Formula 1.

[Chemical Formula 1]

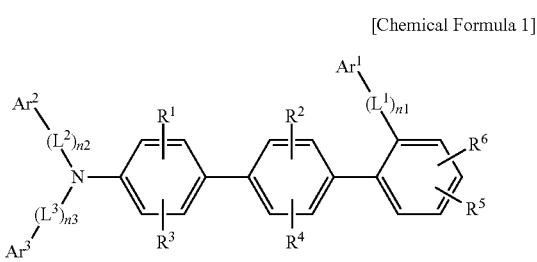

In Chemical Formula 1, $Ar^1$ is a substituted or unsubstituted C2 to C60 heteroaryl group, $Ar^2$ and $Ar^3$ are each independently a substituted or unsubstituted C6 to C60 aryl group or any one of the following Chemical Formulae 3-1 to 3-4, $L^1$ to $L^3$ are each independently a single bond, a substituted or unsubstituted C6 to C60 arylene group or a substituted or unsubstituted C2 to C60 heteroarylene group, n1 to n3 are each independently one of integers of 0 to 2, and $R^1$ to $R^6$ are each independently hydrogen, deuterium, a cyano group, a substituted or unsubstituted C1 to C60 alkyl group or a substituted or unsubstituted C6 to C60 aryl group.

[Chemical Formula 3-1]

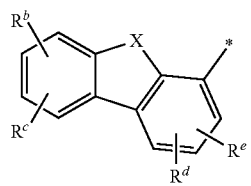

[Chemical Formula 3-2]

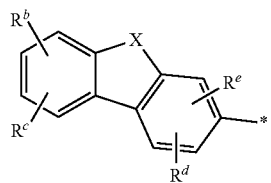

[Chemical Formula 3-3]

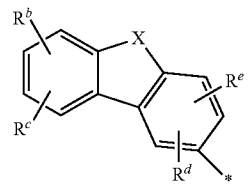

[Chemical Formula 3-4]

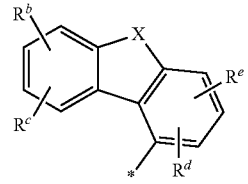

In Chemical Formula 3-1 to Chemical Formula 3-4,

X is —O—, —S— or —$CR^xR^y$—, $R^x$ and $R^y$ are each independently hydrogen, deuterium, a cyano group, a substituted or unsubstituted C1 to C60 alkyl group or a C6 to C60 aryl group, or fused to each other to form a ring, and $R^b$ to $R^e$ are each independently hydrogen, deuterium, a cyano group, a substituted or unsubstituted C1 to C60 alkyl group or a C6 to C60 aryl group.

The compound represented by Chemical Formula 1 has a structure in which any one of substituents of the amine group is a terphenylene group, and a substituted or unsubstituted heteroaryl group bonds to an ortho position based on the phenyl group farthest from the position of the terphenylene group at which the amine group bonds.

From the bonding structure of the amine group and the terphenylene, the HOMO electron cloud is expanded, and through this, the HOMO energy level increases and hole injection and hole transfer abilities are further strengthened, and as a result, a driving voltage of a diode using the same may be lowered.

Moreover, by increasing the HOMO energy level from the substituted or unsubstituted heteroaryl group bonding to an ortho position based on the phenyl group farthest from the position of the terphenylene at which the amine group bonds, hole injection and hole transfer abilities are further strengthened, and high efficiency and long lifetime may be expected.

This is due to the fact that intermolecular interactions are reduced by increasing a steric size when compared to a compound including a substituted or unsubstituted heteroaryl group bonding to a para position based on the phenyl group farthest from the position of the terphenylene at which the amine group bonds, which enhances thin film stability by suppressing material crystallization.

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting diode to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and thereby has excellent thermal stability. Such an increase in the thermal stability becomes an important factor in providing driving stability to a device.

As one example, $Ar^1$ may be any one of the following Chemical Formulae 2-1 to 2-5.

[Chemical Formula 2-1]

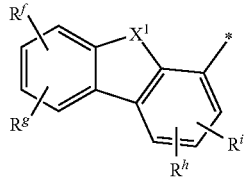

[Chemical Formula 2-2]

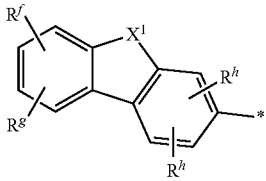

-continued

[Chemical Formula 2-3]

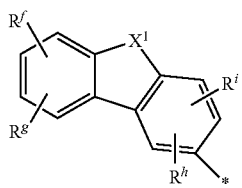

[Chemical Formula 2-4]

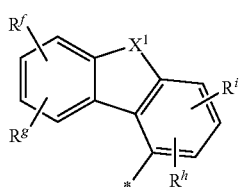

[Chemical Formula 2-5]

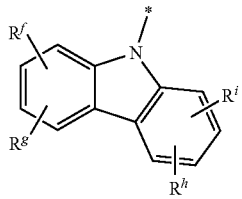

In Chemical Formula 2-1 to Chemical Formula 2-5, $X^1$ is —$NR^x$—, —O— or —S—, $R^h$ to $R^i$ are each independently hydrogen, deuterium, a cyano group, a substituted or unsubstituted C1 to C60 alkyl group, a substituted or unsubstituted C6 to C60 aryl group, or a substituted or unsubstituted C2 to C60 heteroaryl group.

From Chemical Formulae 2-1 to 2-5, the compound has properties of enhanced rigidity and heat resistance, and by having low electric field strength, an effect of improving a hole migration rate may be expected.

More specifically, $Ar^1$ may be a substituted or unsubstituted carbazolyl group. Herein, the HOMO electron cloud is expanded, and through this, the HOMO energy level increases and hole injection and hole transfer abilities are further strengthened, and as a result, a driving voltage of a diode using the same may be lowered.

More specifically, $Ar^1$ may be a substituted or unsubstituted dibenzofuranyl group. Herein, the compound has properties of enhanced rigidity and heat resistance, and by having low electric field strength, a property of high hole migration rate is obtained.

$Ar^1$ may be a substituted or unsubstituted dibenzothiophenyl group. Similarly, the compound has properties of enhanced rigidity and heat resistance, and by having low electric field strength, a property of high hole migration rate is obtained.

$R^h$ to $R^i$ are each independently hydrogen, a substituted or unsubstituted C6 to C60 aryl group, or a substituted or unsubstituted C2 to C60 heteroaryl group.

$R^h$ to $R^i$ are each independently hydrogen, a substituted or unsubstituted C6 to C40 aryl group, or a substituted or unsubstituted C2 to C40 heteroaryl group.

$R^h$ to $R^i$ are each independently hydrogen, a substituted or unsubstituted C6 to C20 aryl group, or a substituted or unsubstituted C2 to C20 heteroaryl group.

$R^h$ to $R^i$ are each independently hydrogen, a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group.

$R^h$ to $R^i$ are each independently hydrogen, a phenyl group, a biphenyl group, a naphthyl group, a dibenzofuranyl group or a dibenzothiophenyl group.

$Ar^2$ and $Ar^3$ may be each independently any one of substituents of the following Group I.

[Group I]

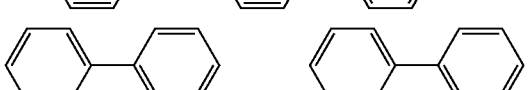
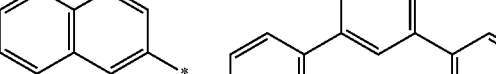
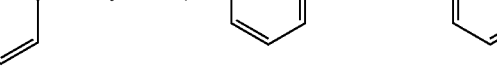
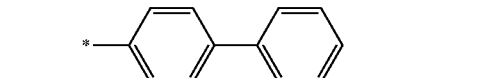
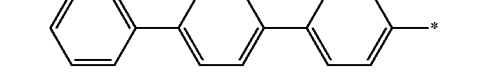
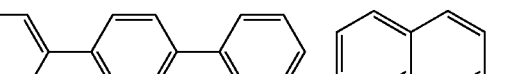
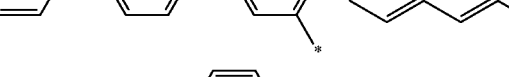
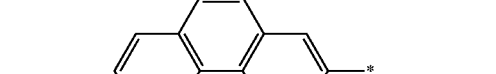
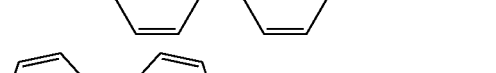
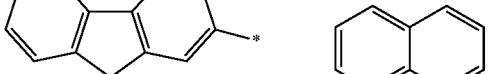

In Group I,

* means a bonding position.

When the substituents of $Ar^2$ and $Ar^3$ are one of the substituents of Group I, hole mobility may be improved, and a low driving value is obtained even when used in a hole transfer layer.

More specifically, any one of $Ar^2$ and $Ar^3$ may be any one of the following Chemical Formulae 3-1 to 3-4.

[Chemical Formula 3-1]

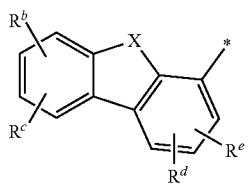

[Chemical Formula 3-2]

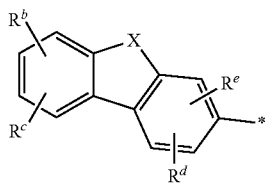

[Chemical Formula 3-3]

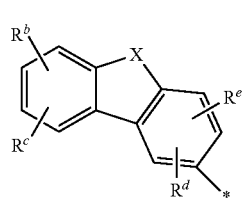

[Chemical Formula 3-4]

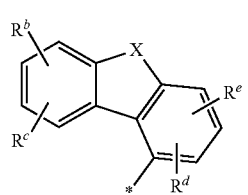

In Chemical Formula 3-1 to Chemical Formula 3-4,

X is —O—, —S— or —CR$^x$R$^y$—, R$^x$ and R$^y$ are each independently hydrogen, deuterium, a cyano group, a substituted or unsubstituted C1 to C60 alkyl group or a C6 to C60 aryl group, and R$^b$ to R$^e$ are each independently hydrogen, deuterium, a cyano group, a substituted or unsubstituted C1 to C60 alkyl group or a C6 to C60 aryl group.

The compound of the one example described above may be represented by any one of compounds of the following Group II.

[Group II]

A1-1

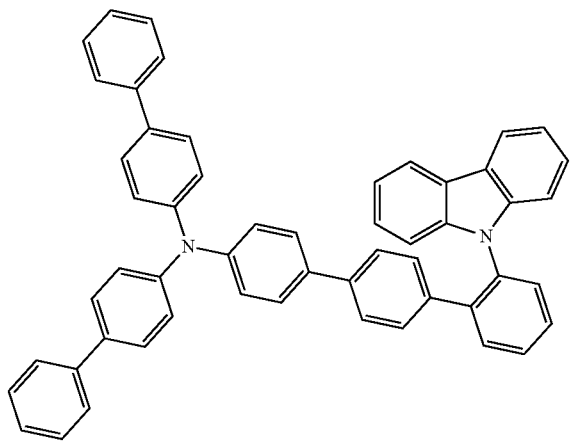

A1-2

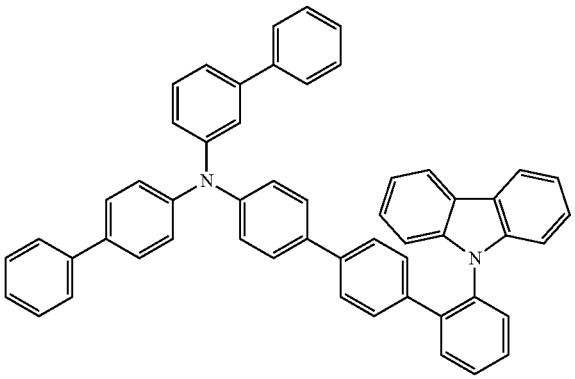

A1-3

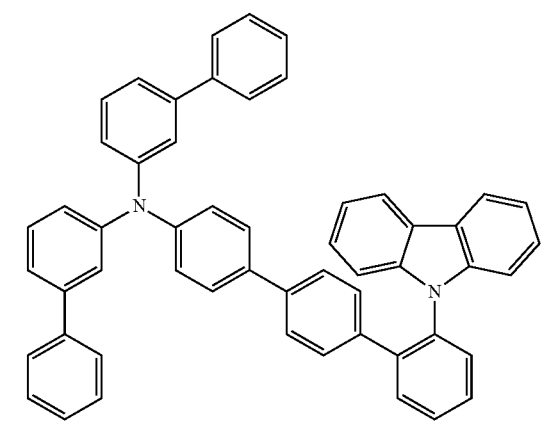

A1-4

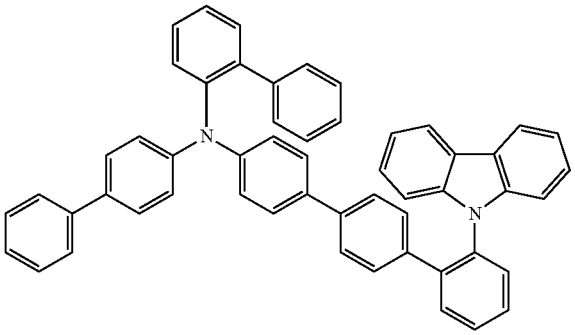

A1-5

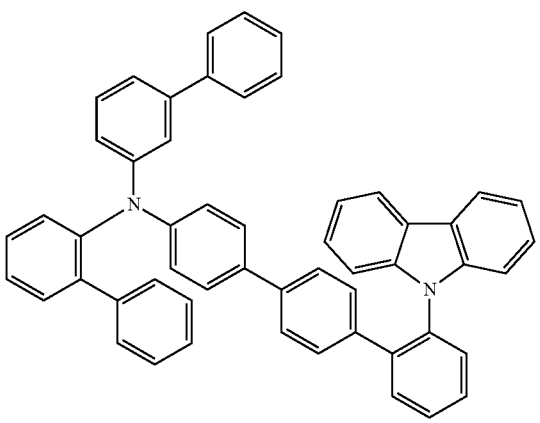

A1-6
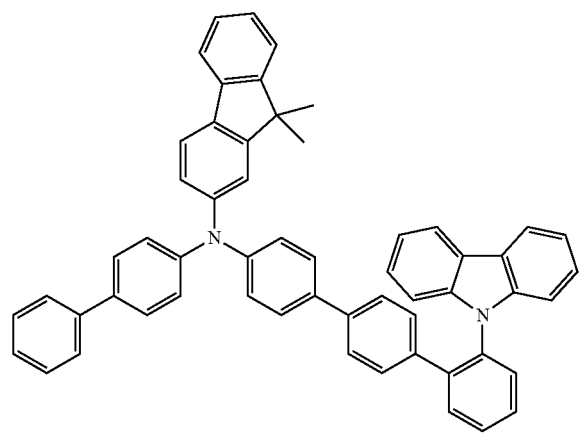
A1-7
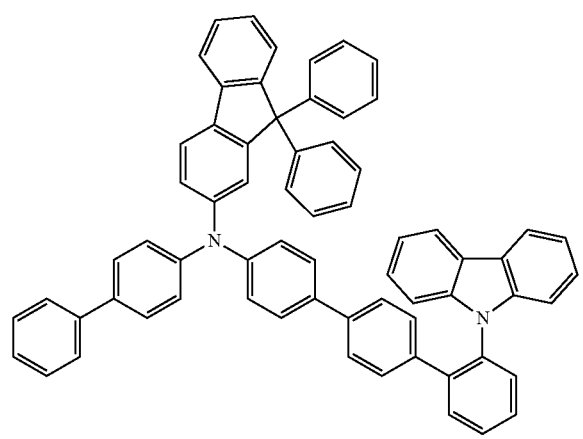
A1-8
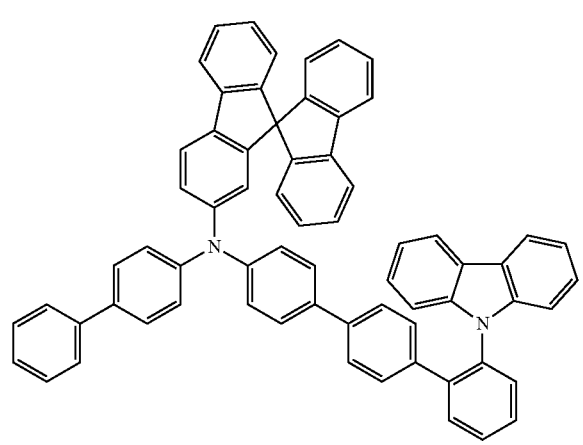
A1-9
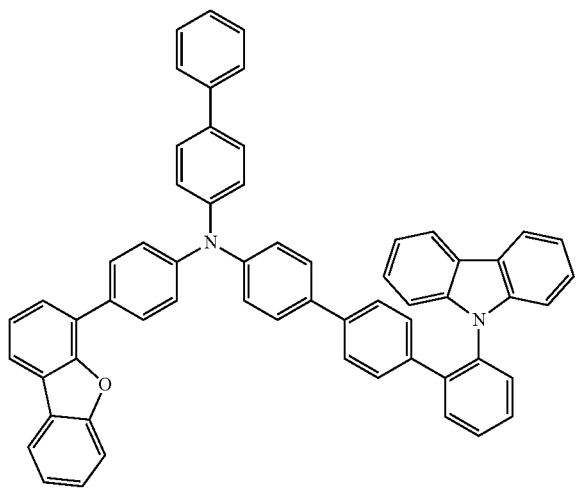
A1-10
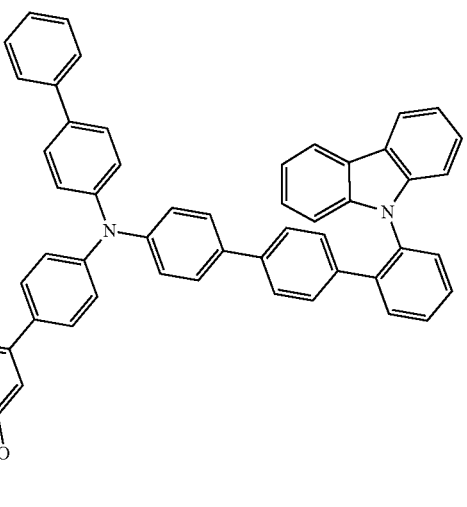
A1-11
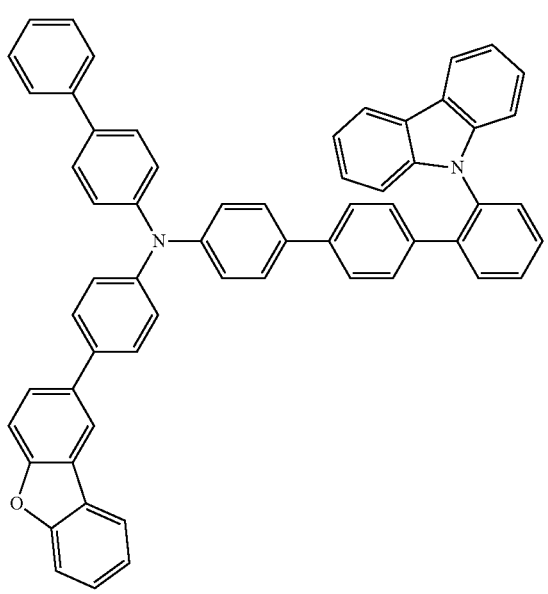

A1-12
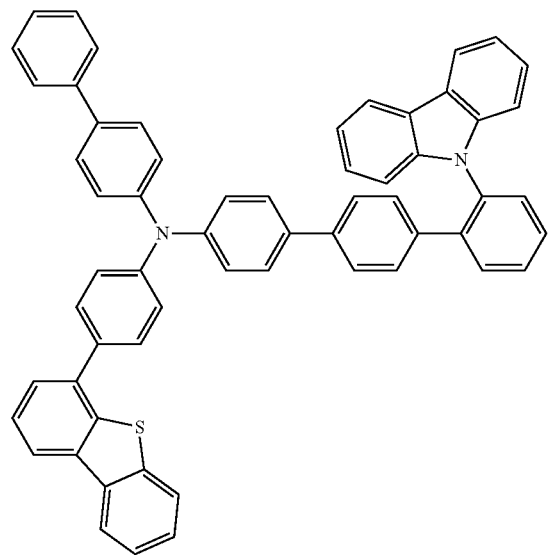
A1-13
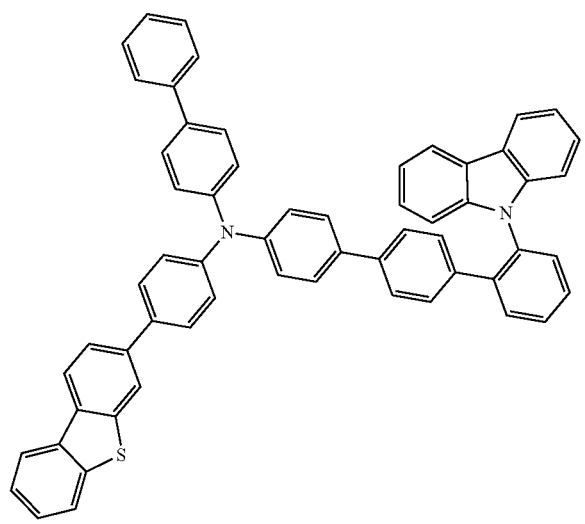
A1-14
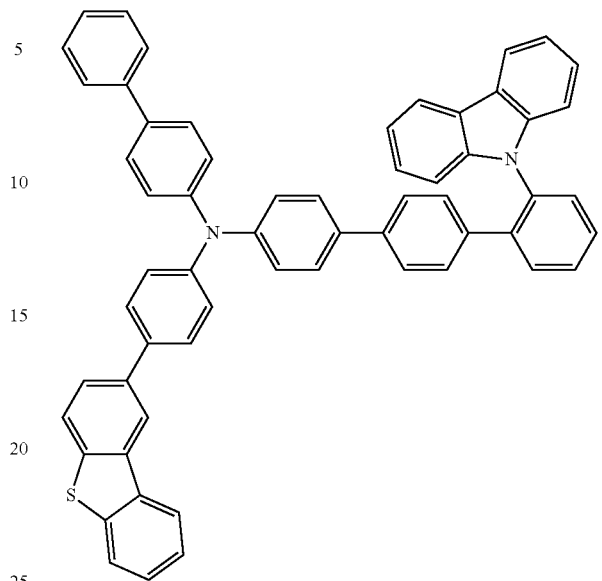
A1-15
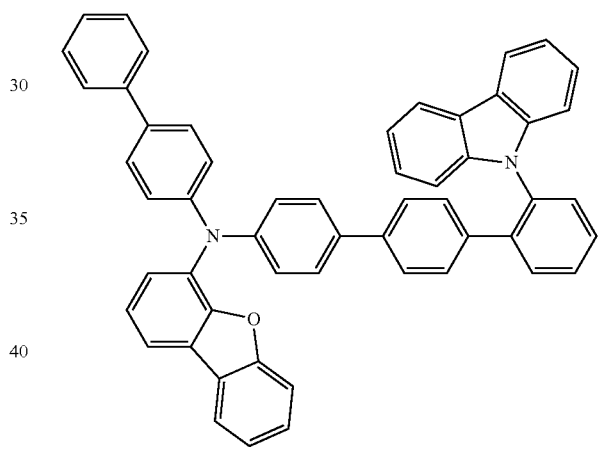
A1-16
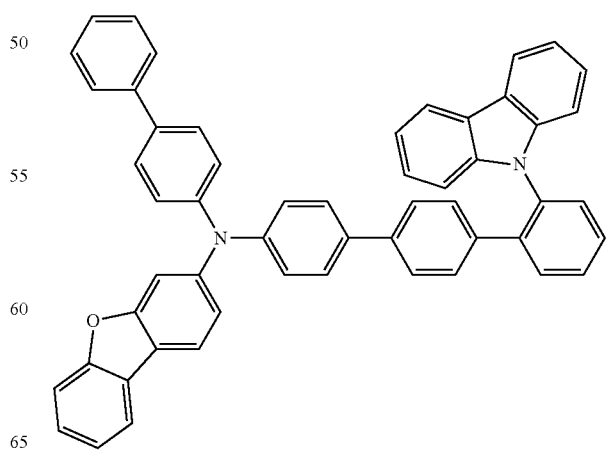

A1-17
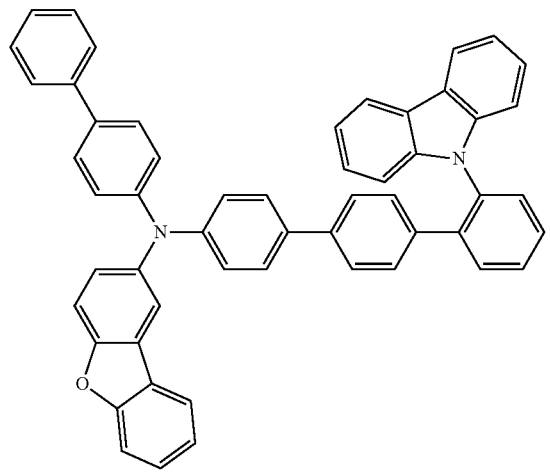
A1-18
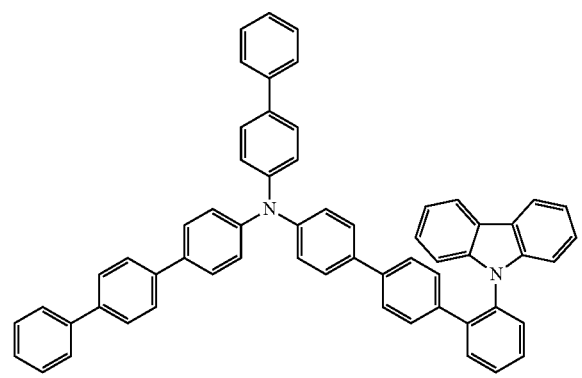
A1-19
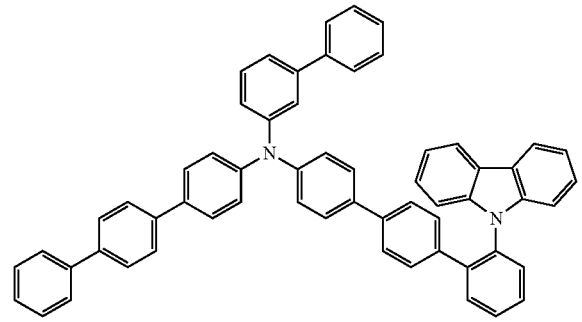
A1-20
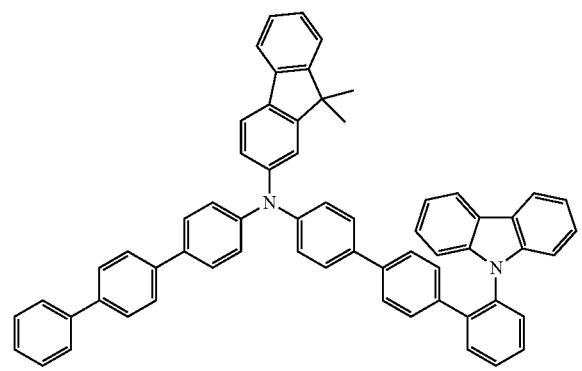
A1-21
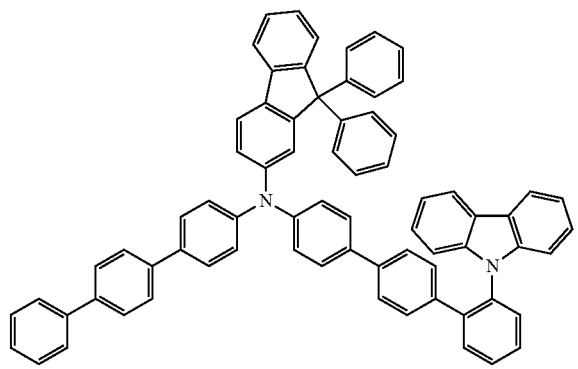
A1-22
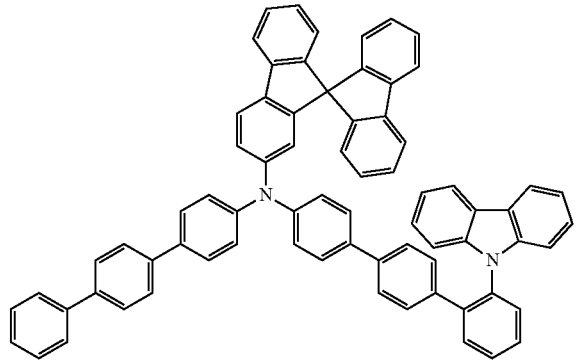
A1-23
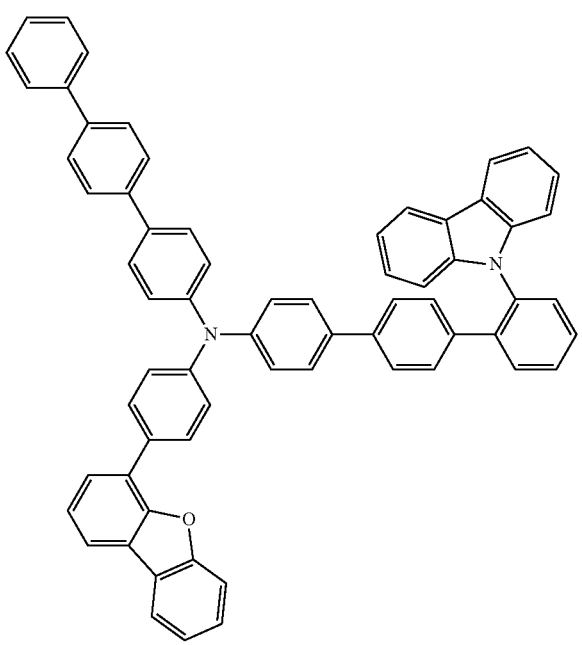

A1-24
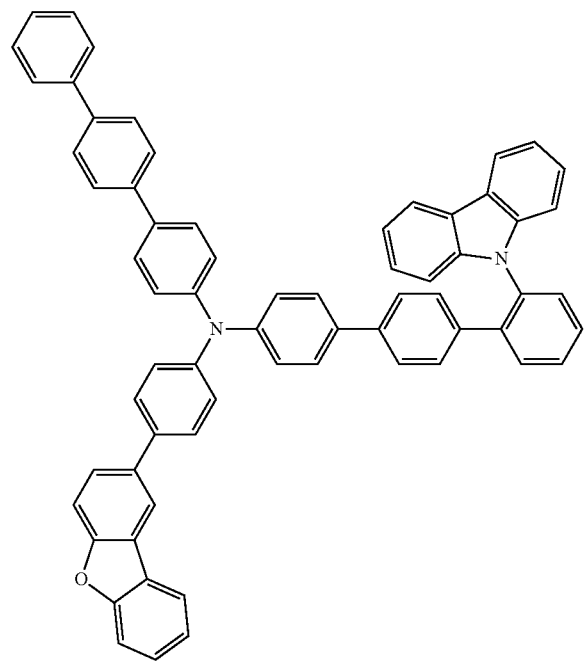
A1-25
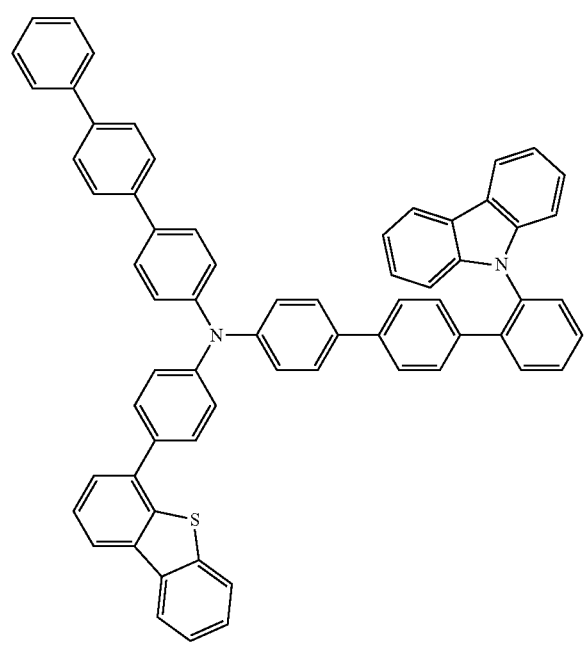
A1-26
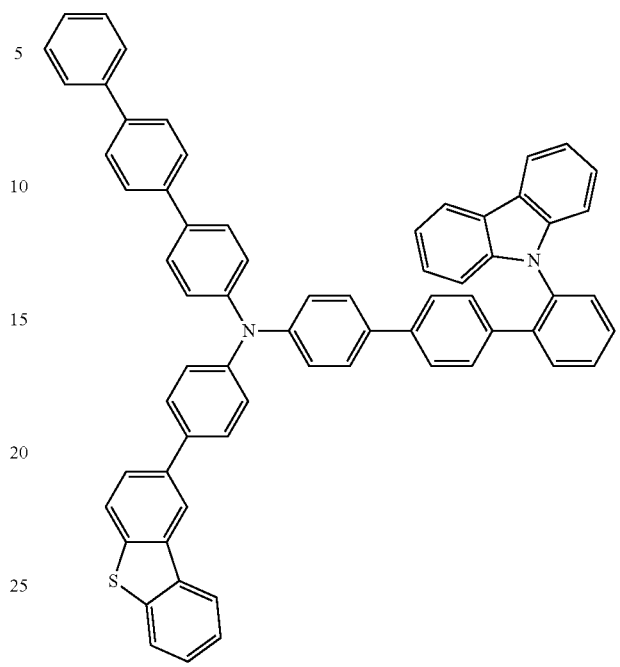
A1-27
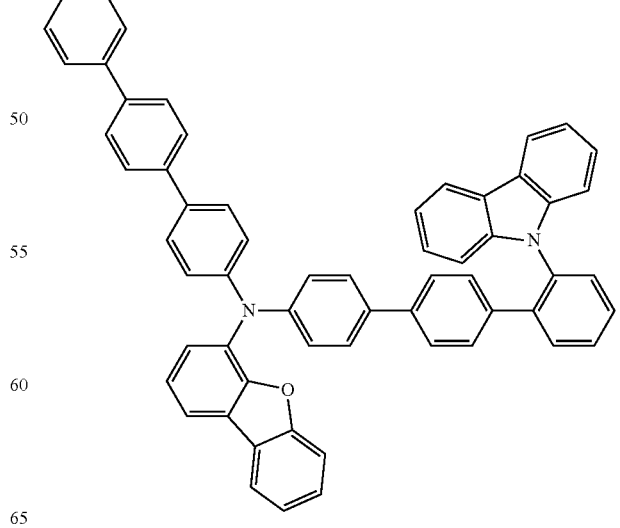

A1-28
A1-30
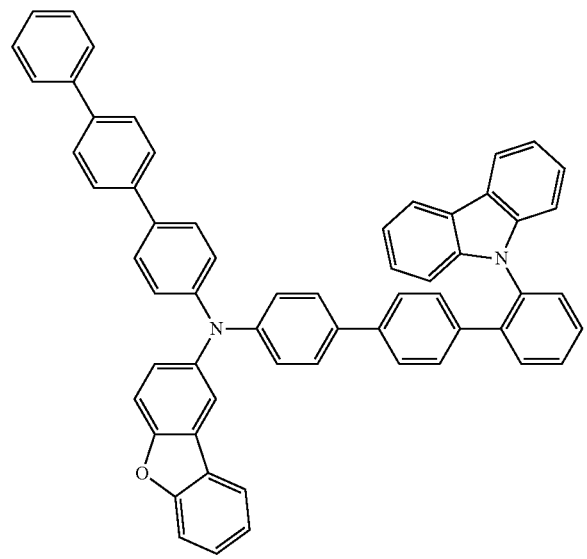
A1-29
A1-31
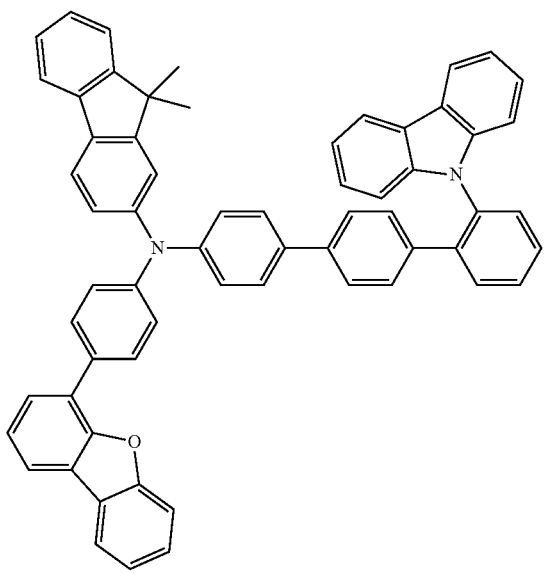

-continued
A1-32
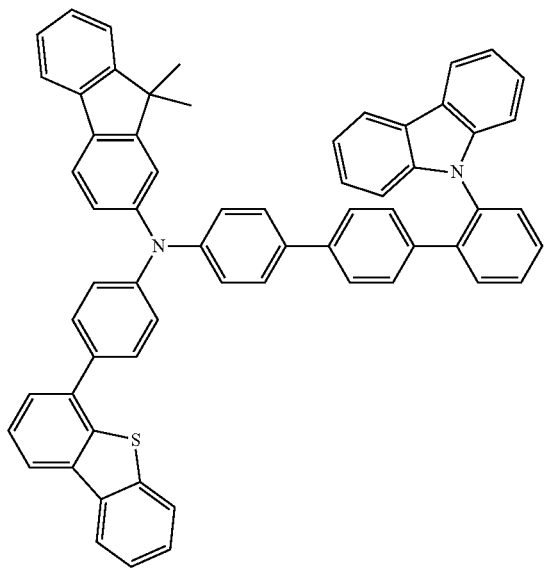
A1-35
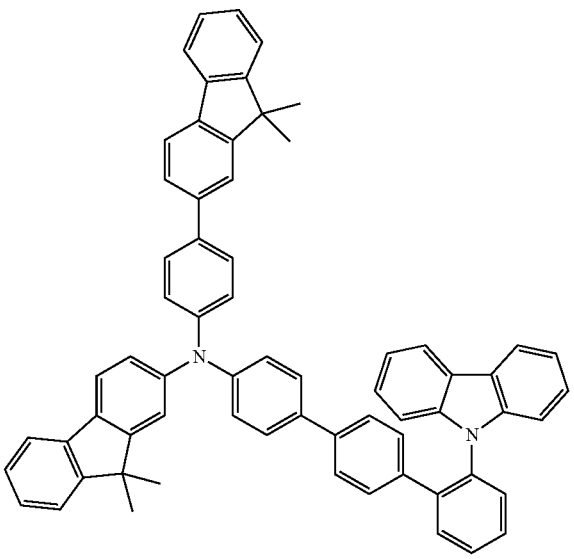
A1-33
A1-34
A1-36
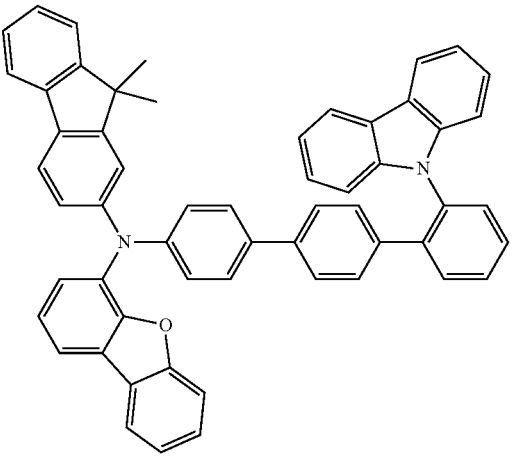
A1-37
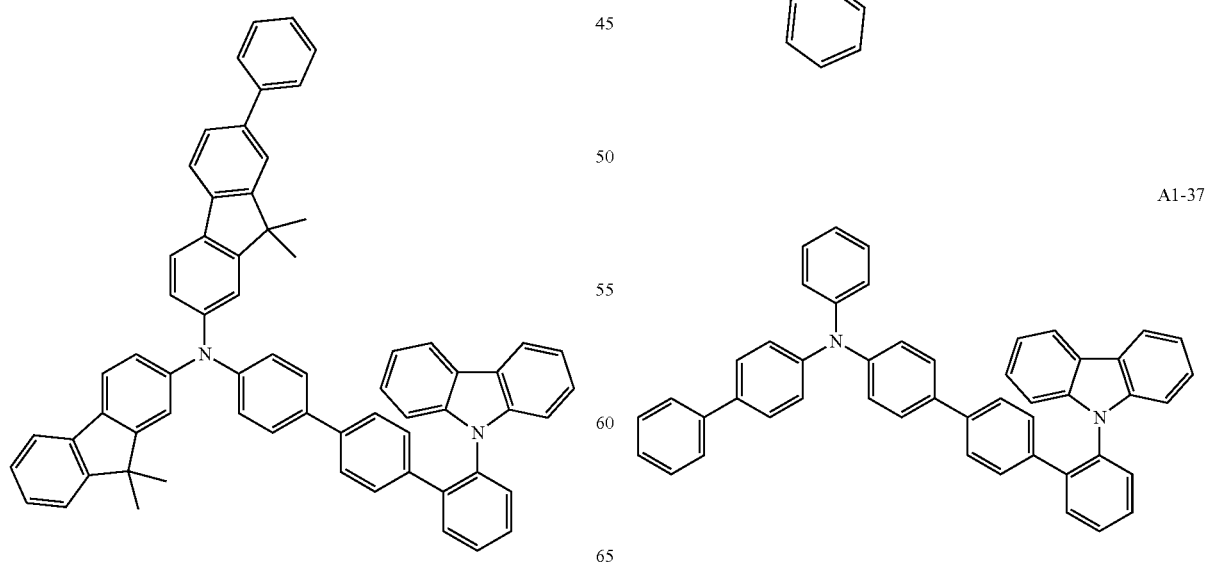

A1-38
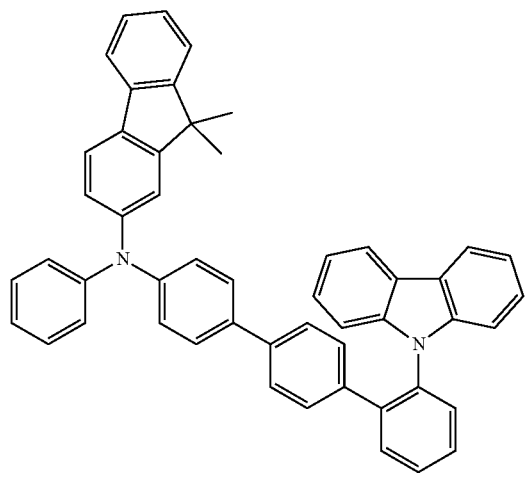
A1-39
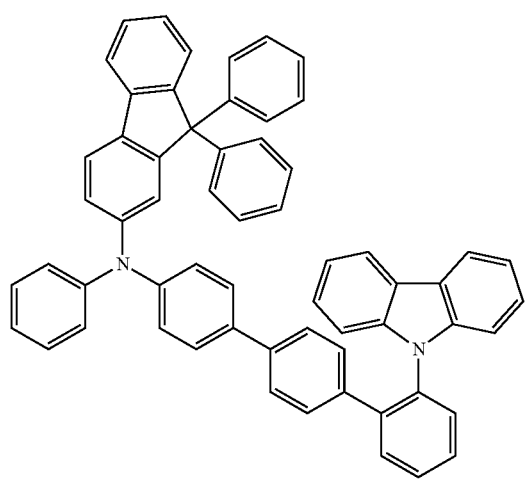
A1-40
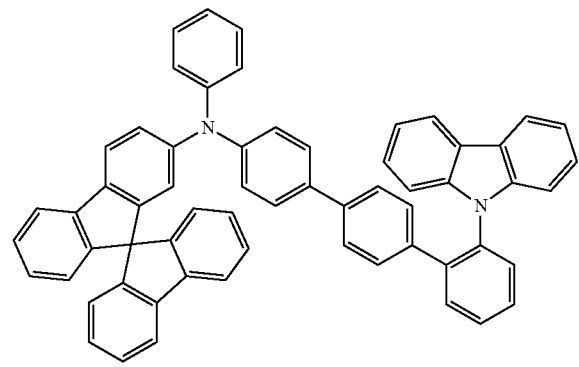
A1-41
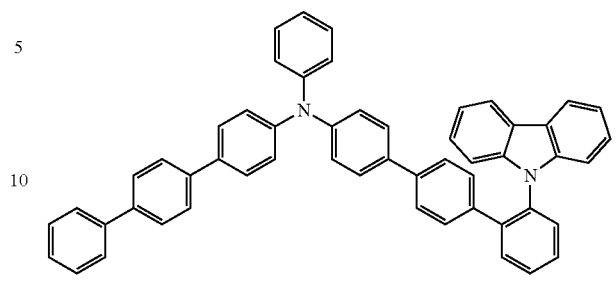
A1-42
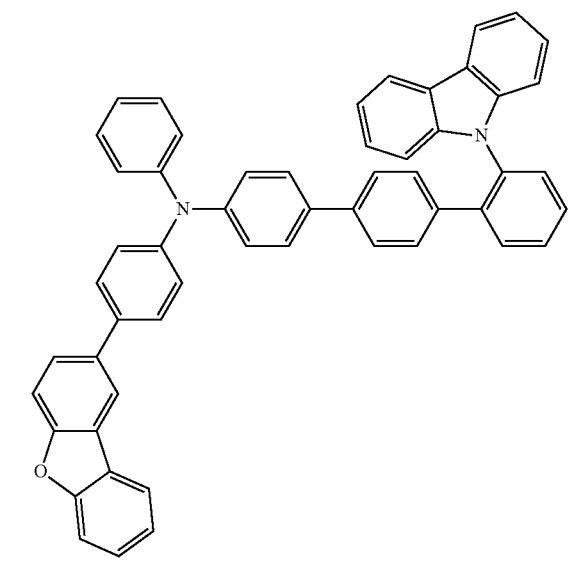
A1-43

A1-44
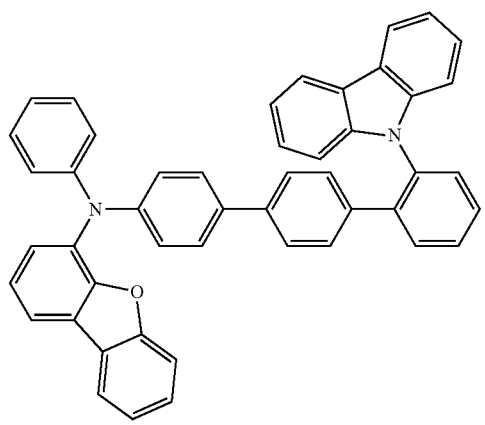
A1-45
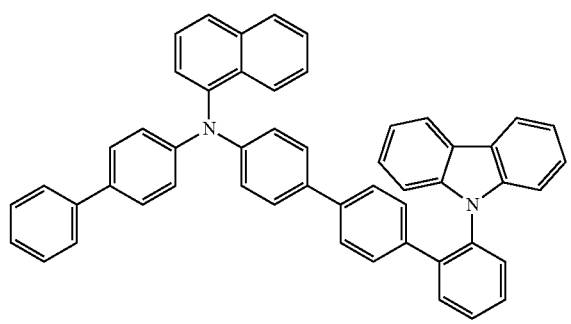
A1-46
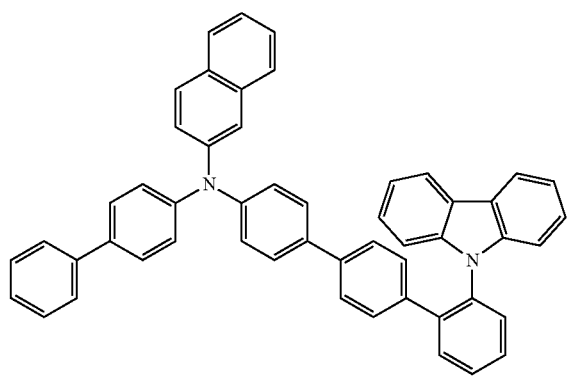
A1-47
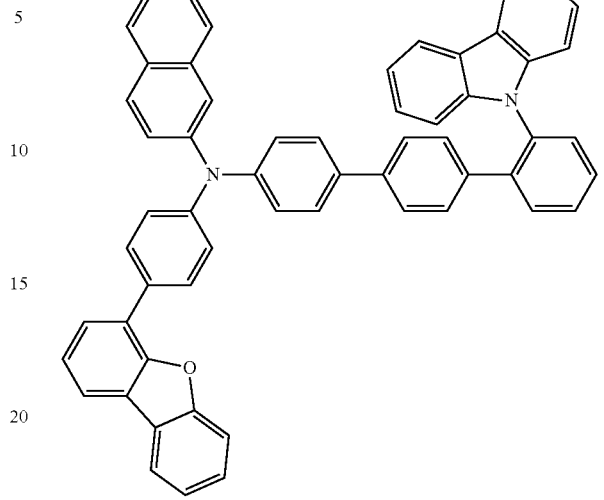
A1-48
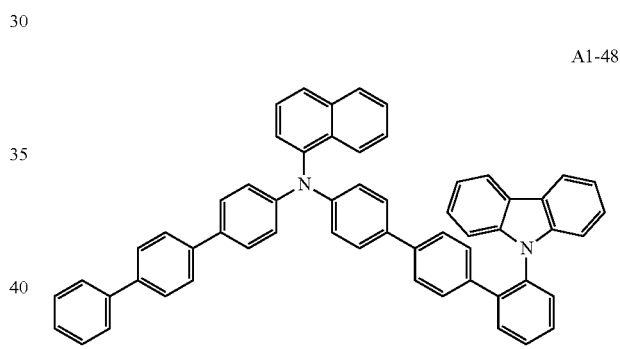
A2-1
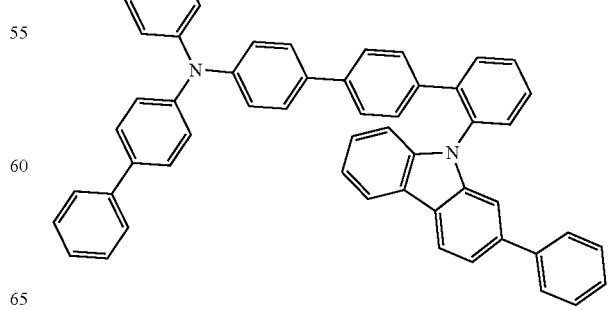

A2-2
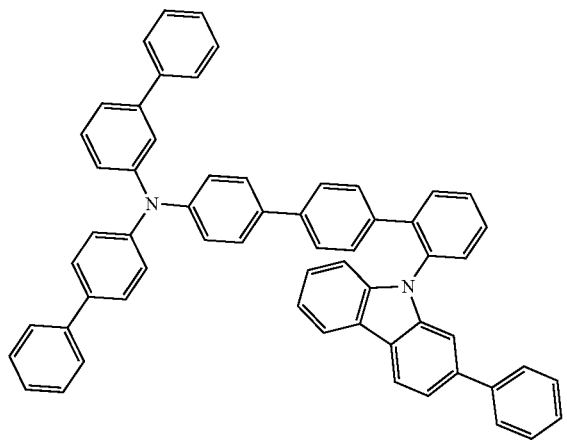
A2-5
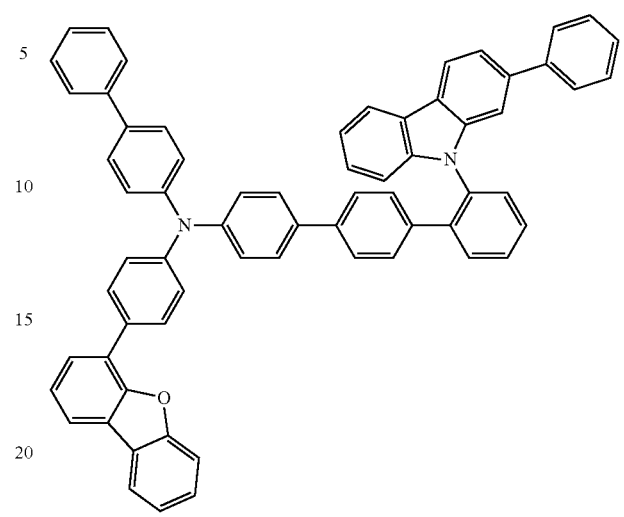
A2-3
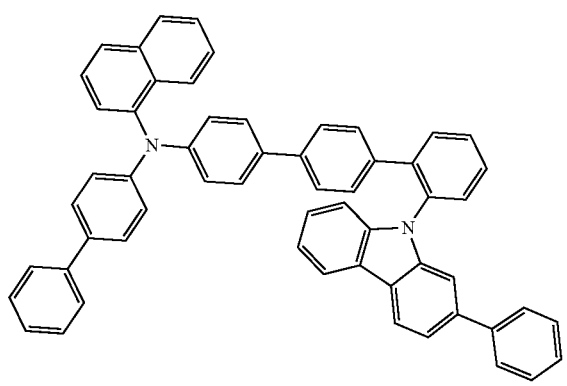
A2-6
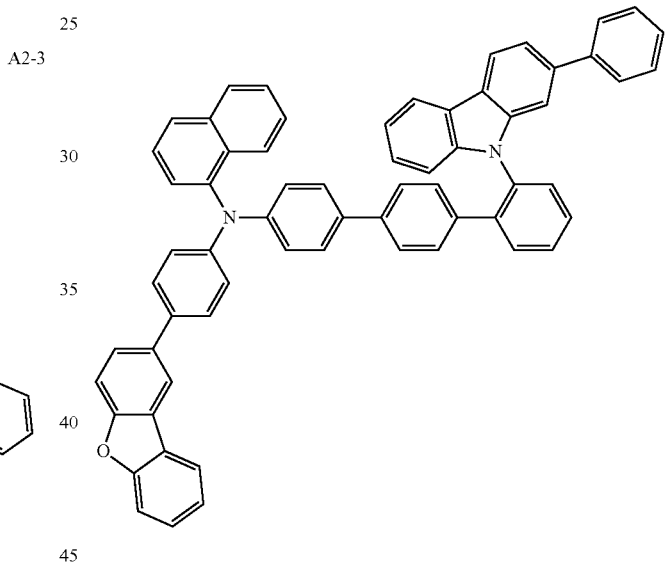
A2-4
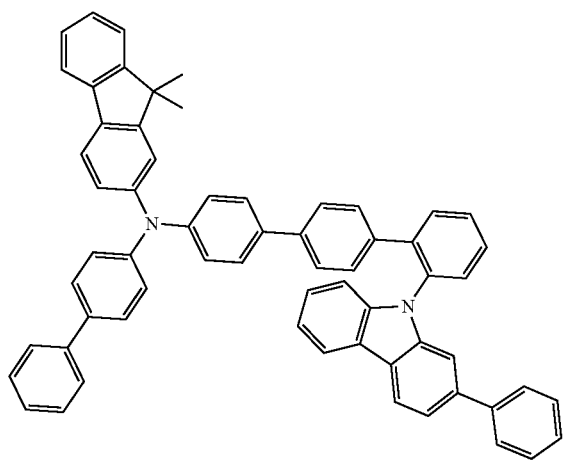
A2-7
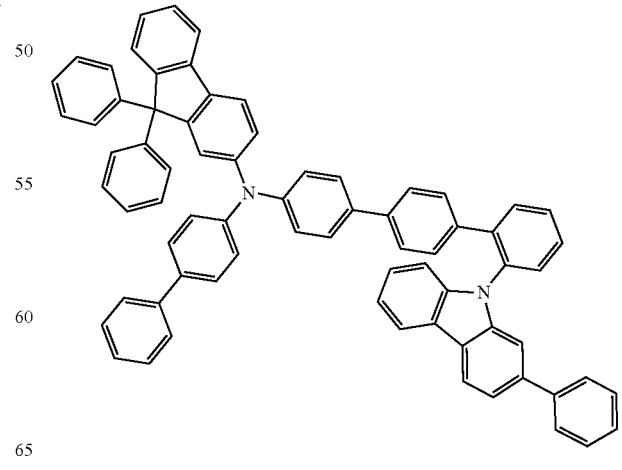

A2-8
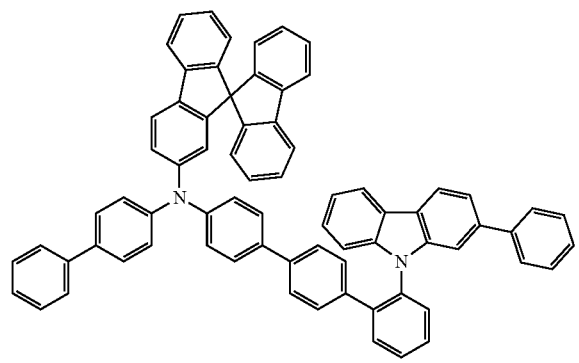
A2-9
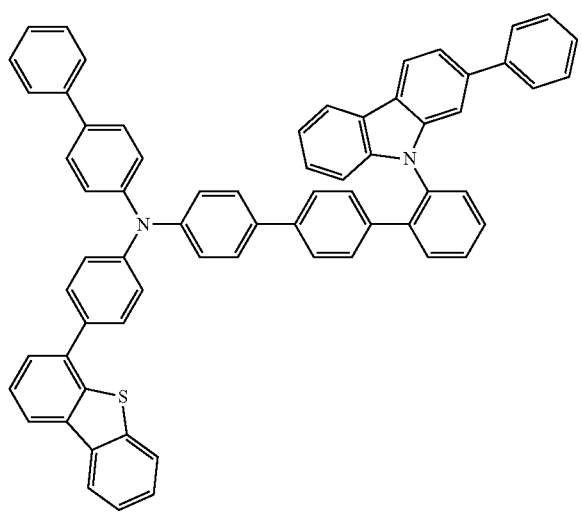
A2-10
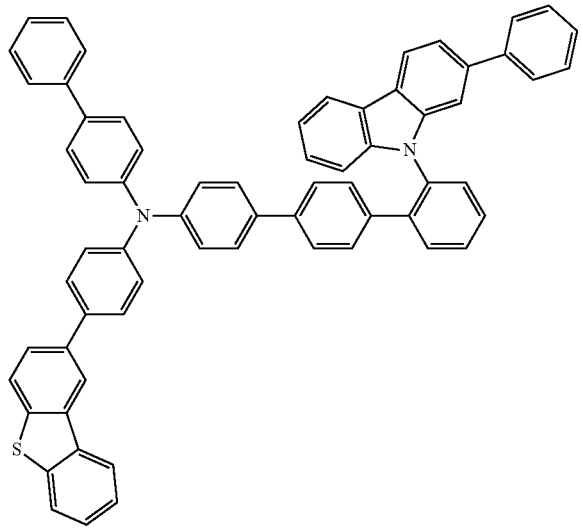
A2-11
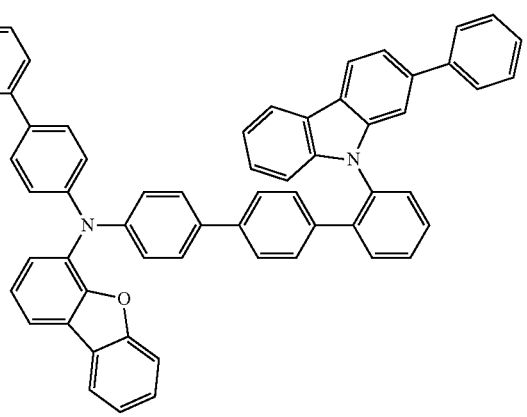
A2-12
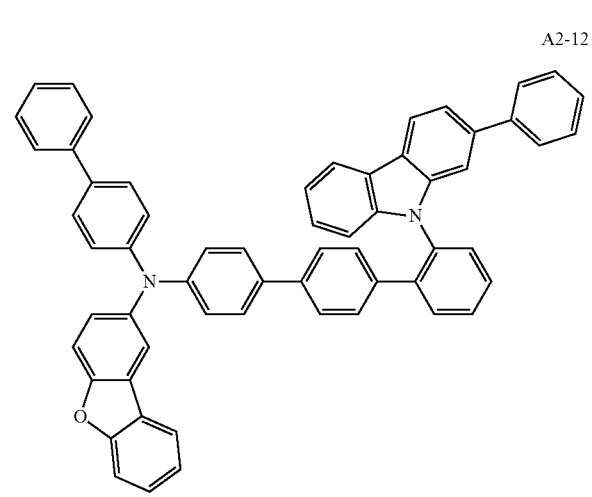
A2-13
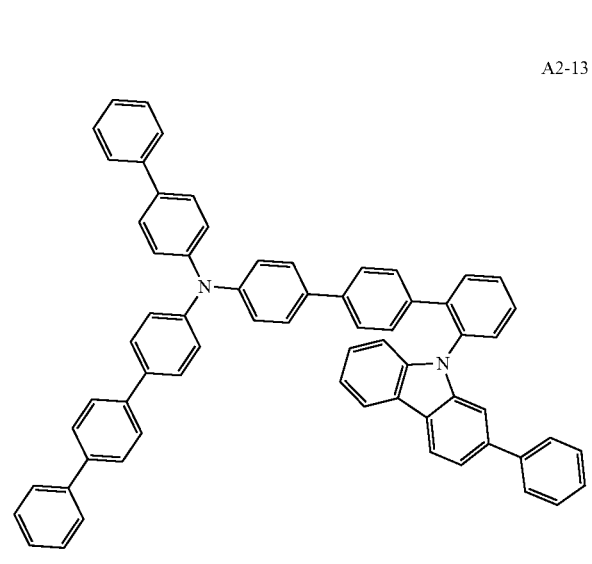

A2-14
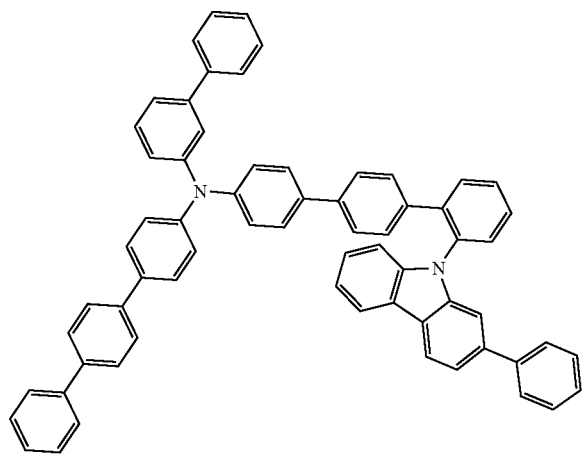
A2-15
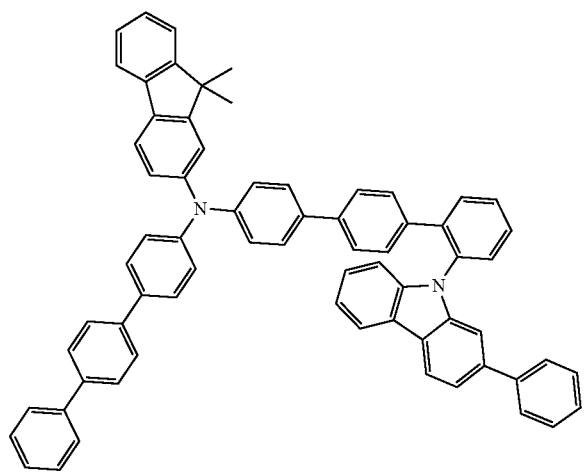
A2-16
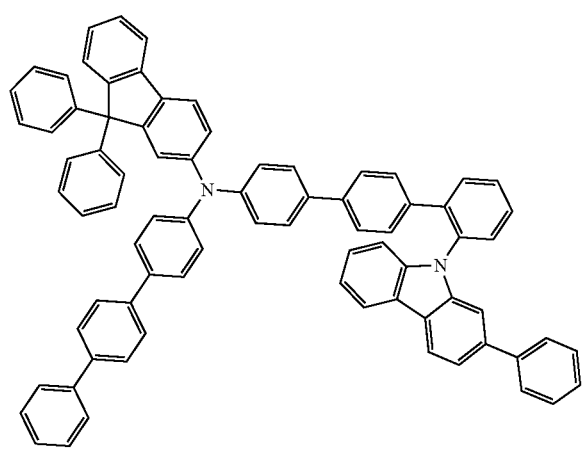
A2-17
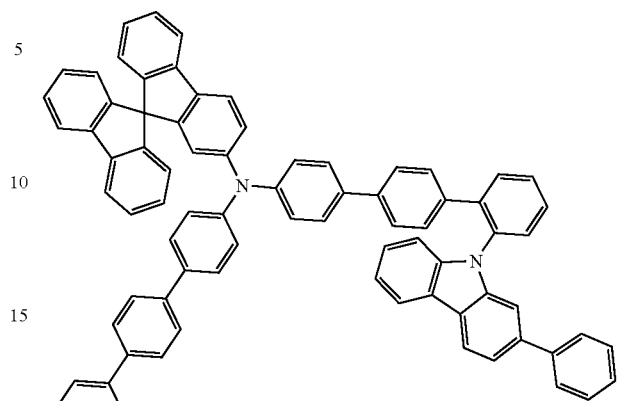
A2-18
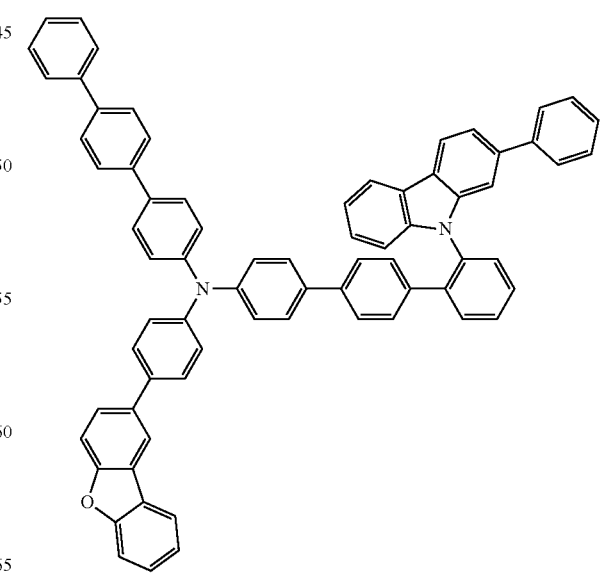
A2-19

A2-20
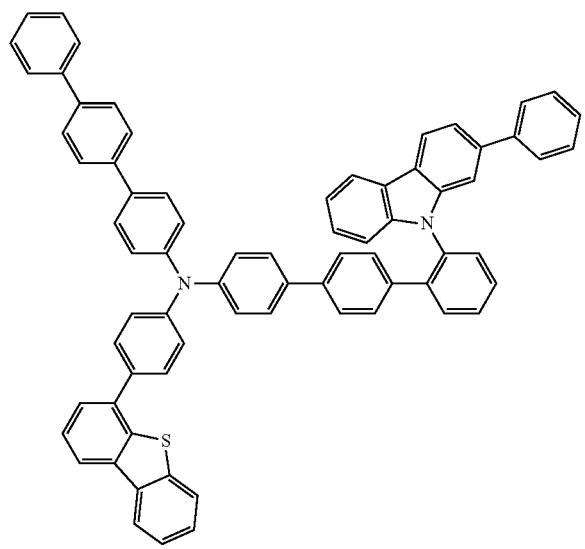
A2-21
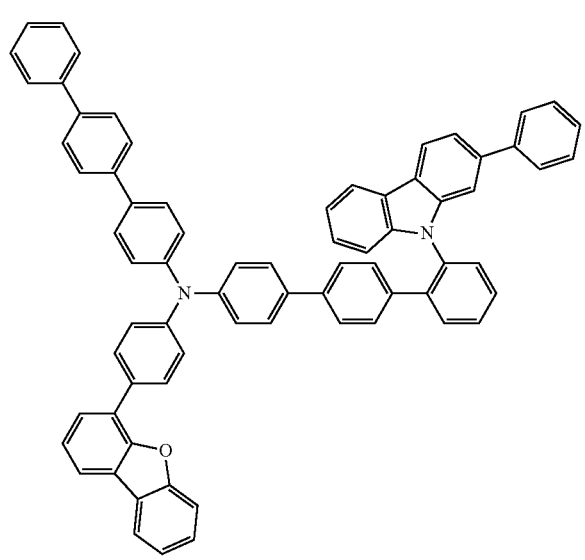
A2-22
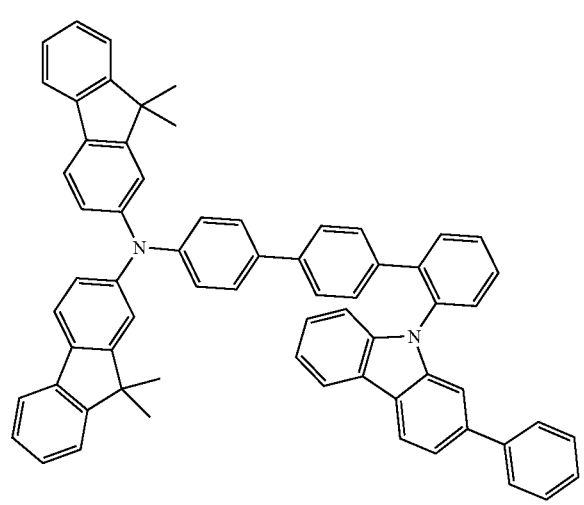
A2-23
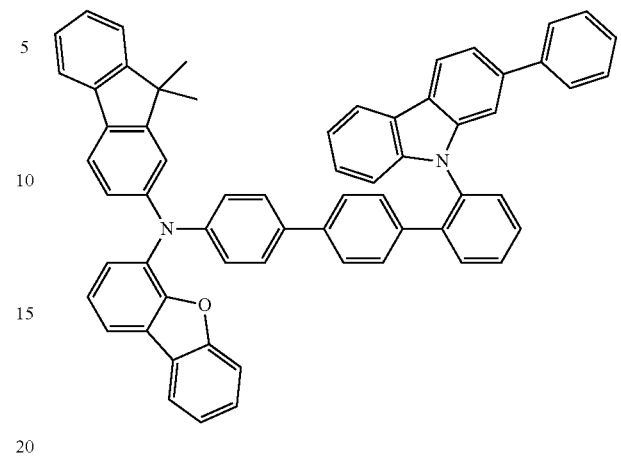
A2-24
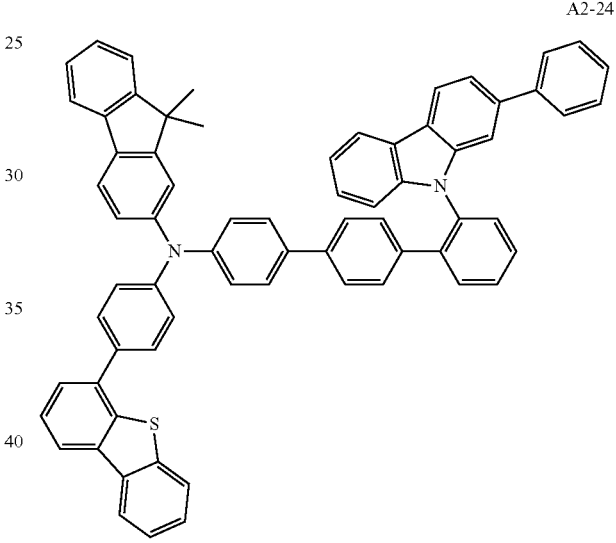
A2-25
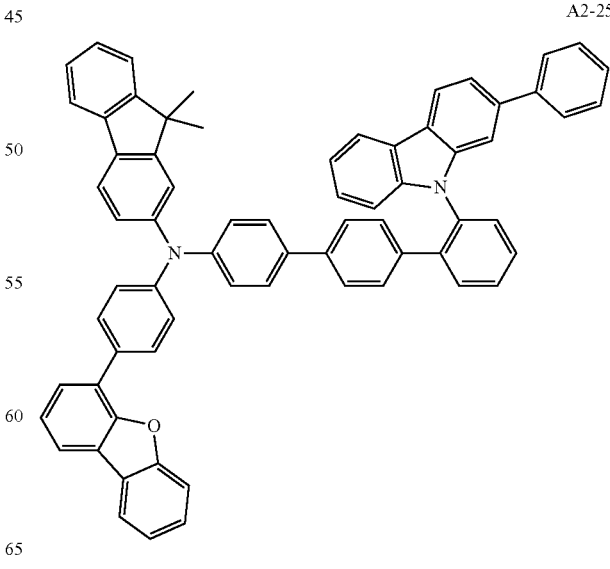

A2-26
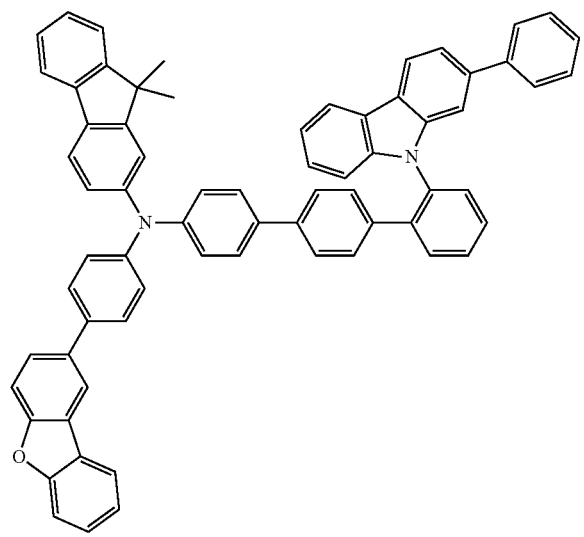
A2-27
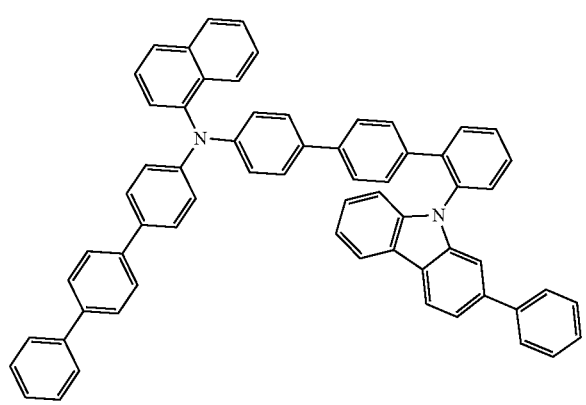
A2-28
A2-29
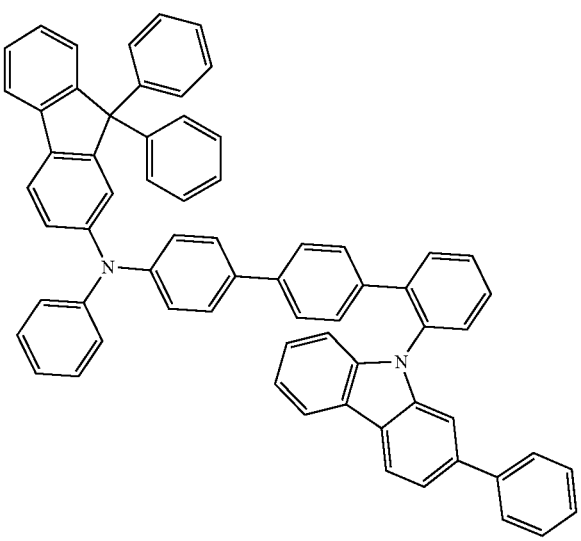
A2-30
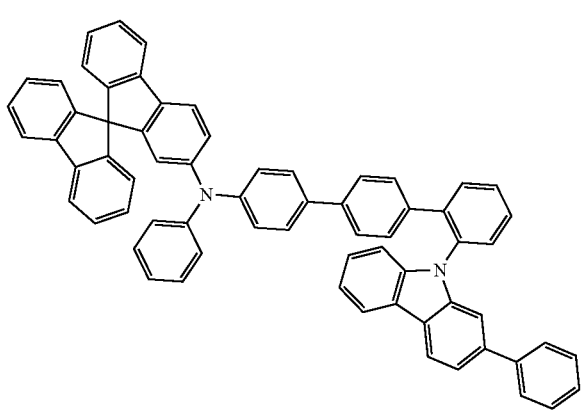
A2-31
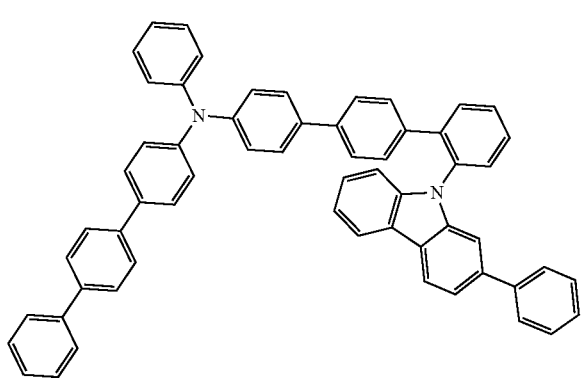

A2-32
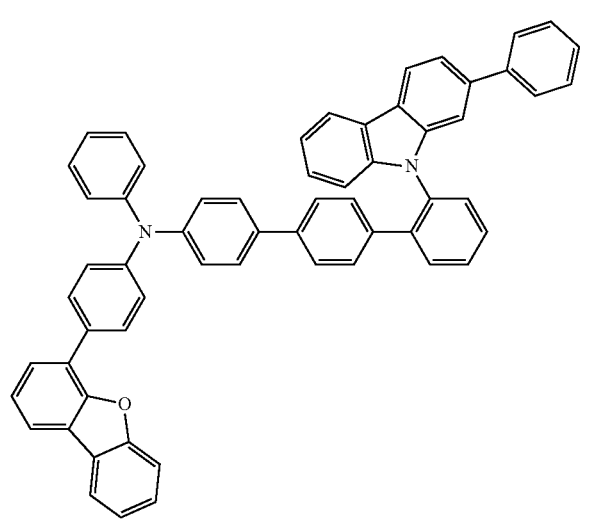
A2-35
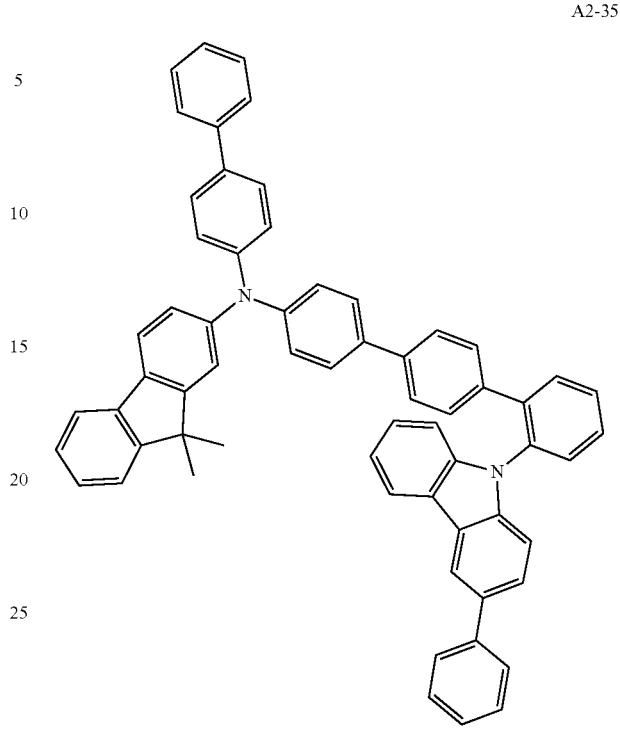
A2-33
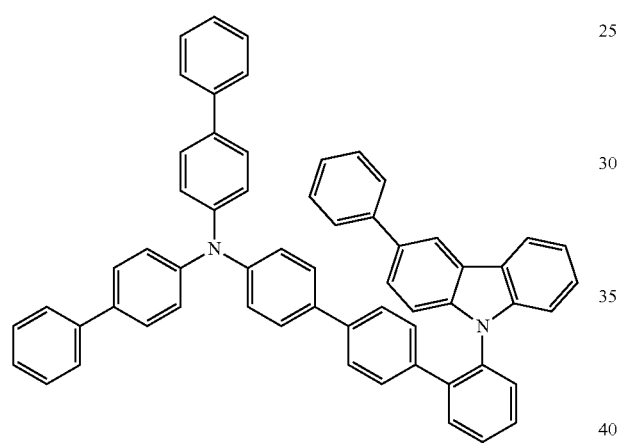
A2-34
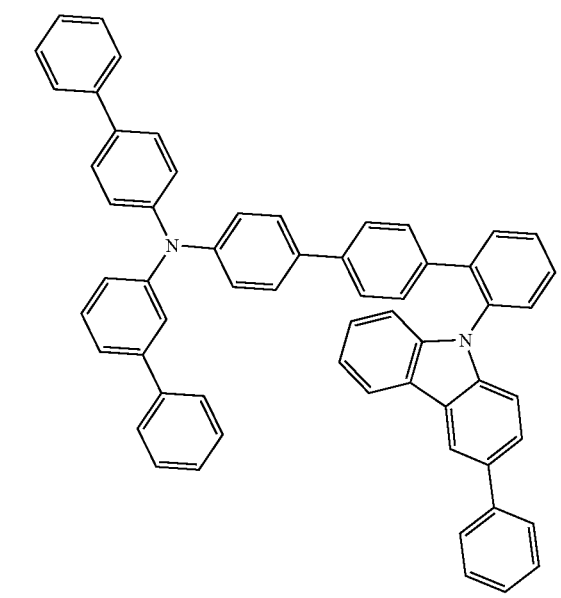
A2-36
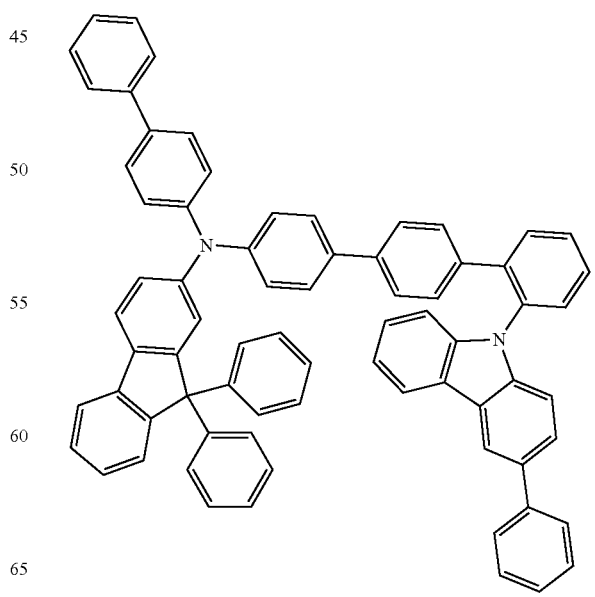

A2-37
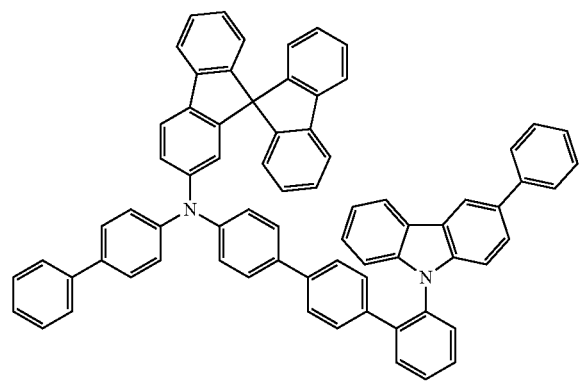
A2-38
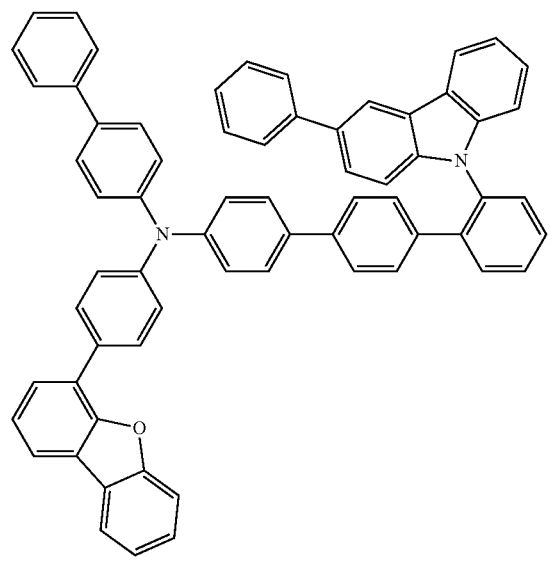
A2-39
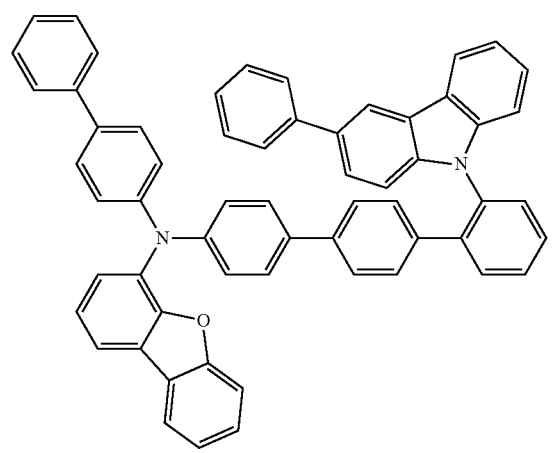
A2-40
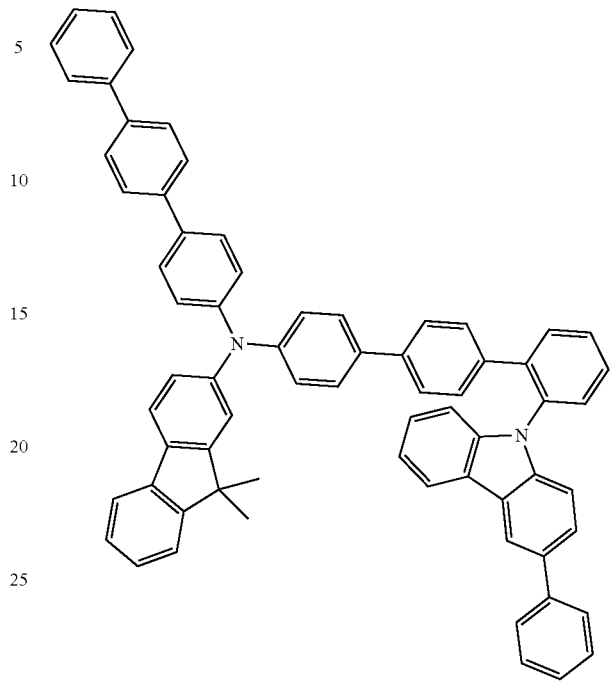
A2-41
A2-42
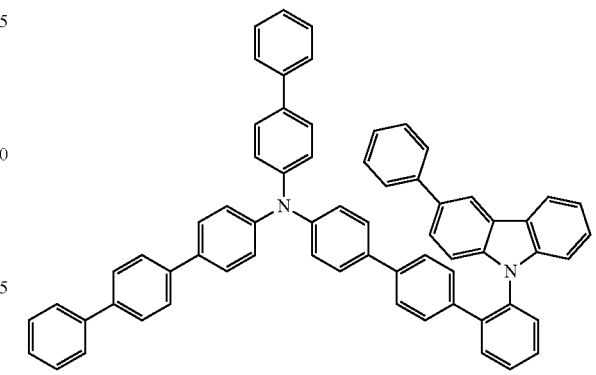

A2-43
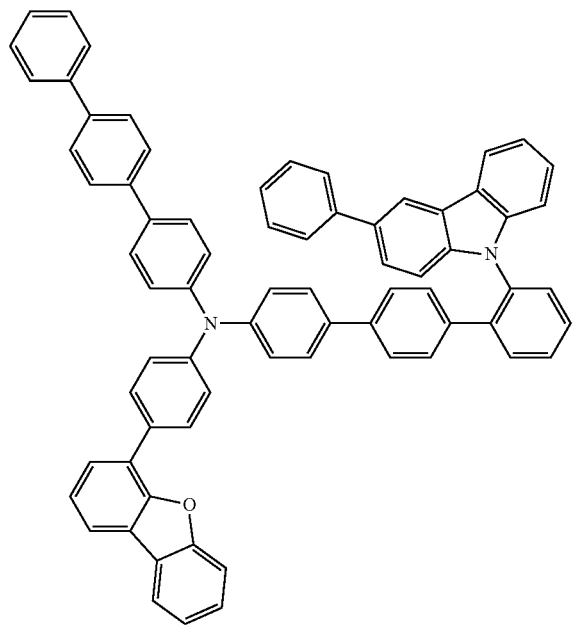
A2-45
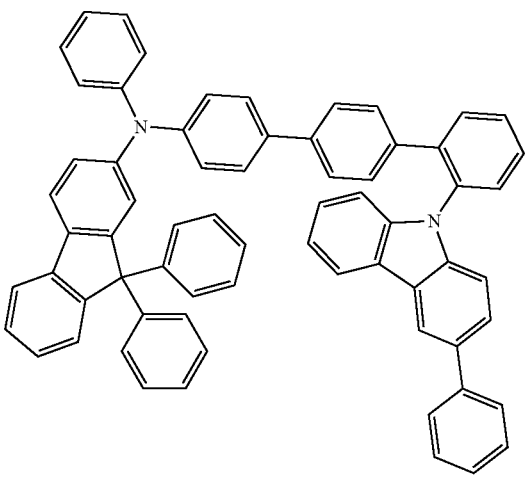
A2-46
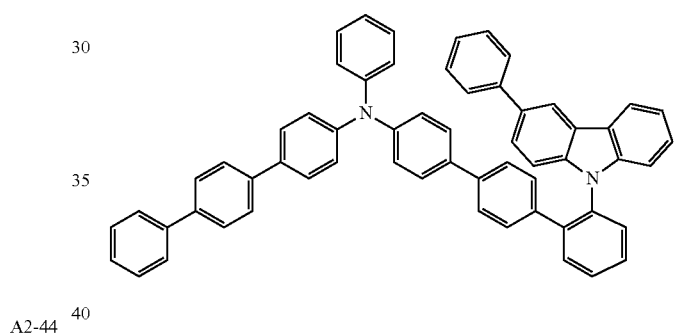
A2-44
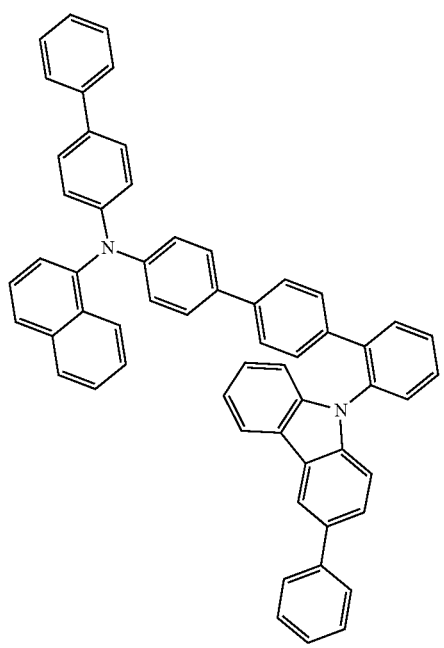
A2-47
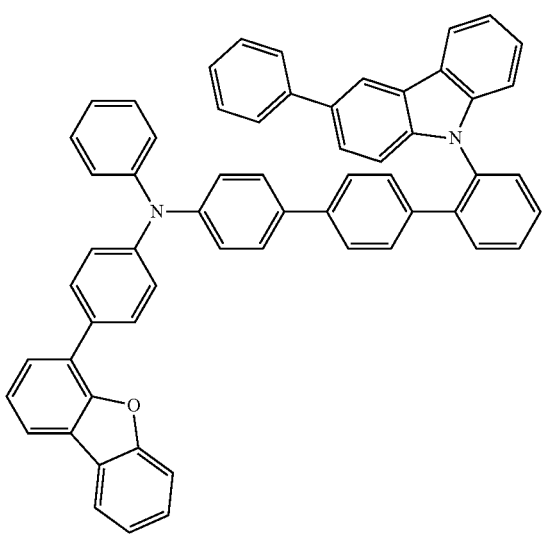

A2-48
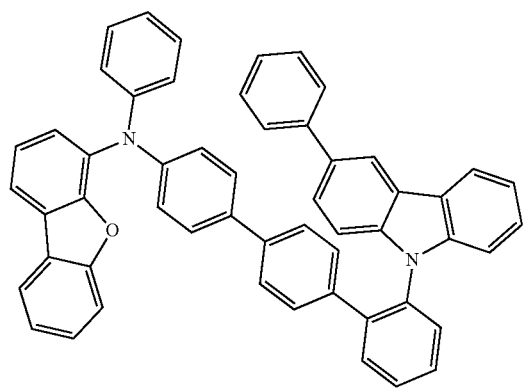
A2-51
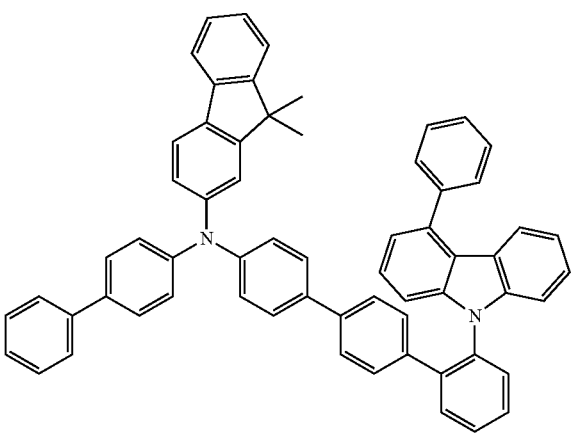
A2-49
A2-50
A2-52
A2-53
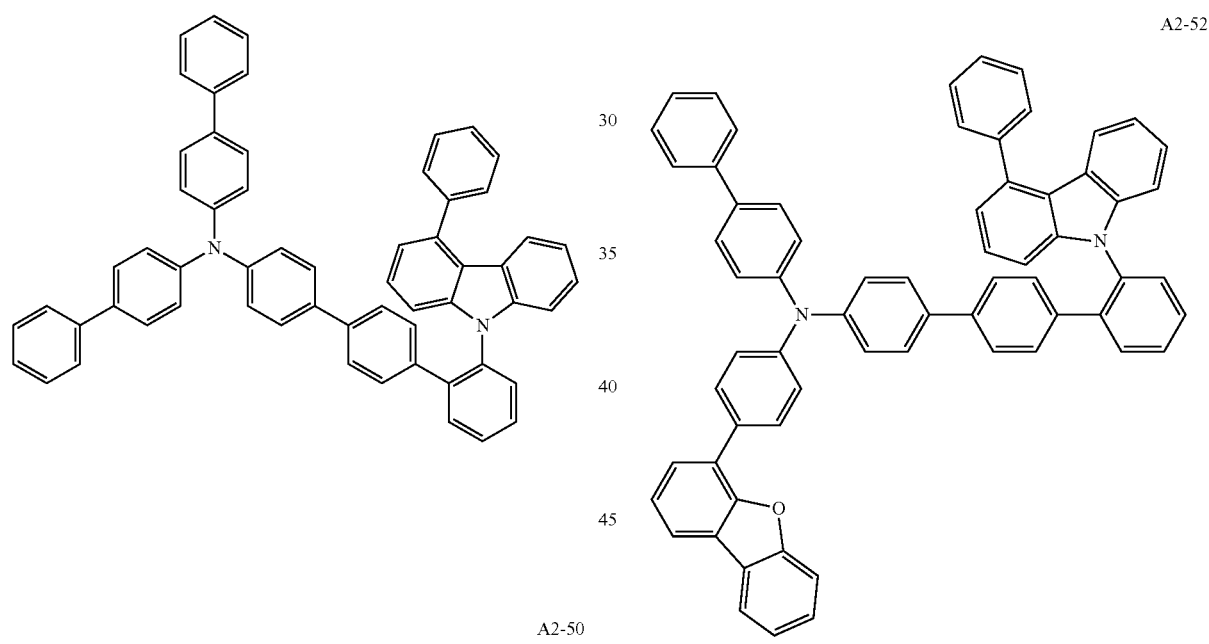
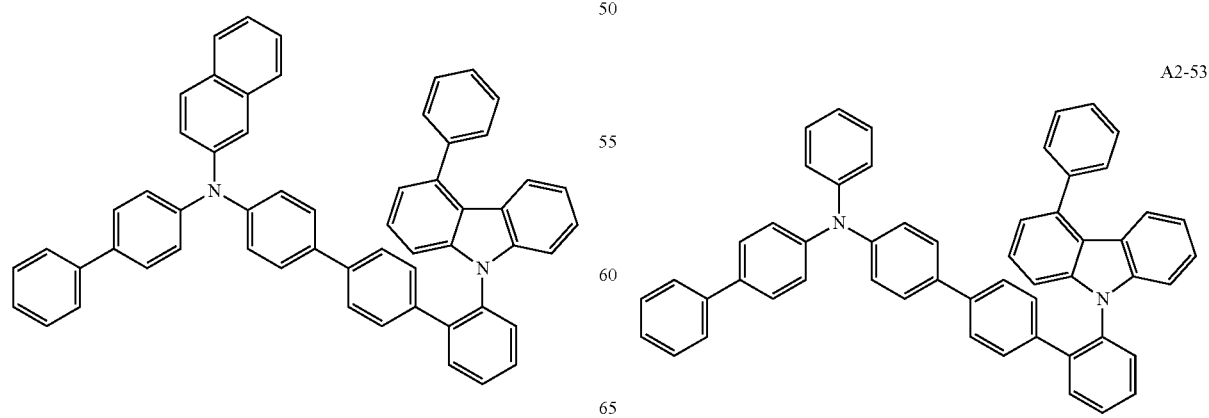

-continued
A2-54
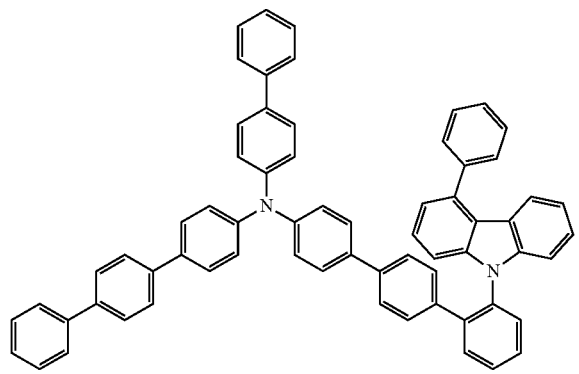
A2-55
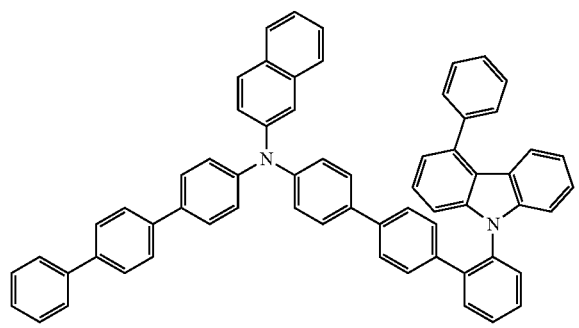
A2-56
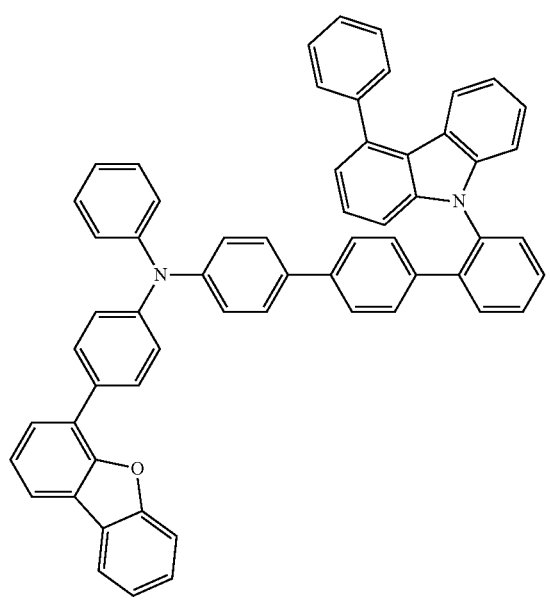
A2-57
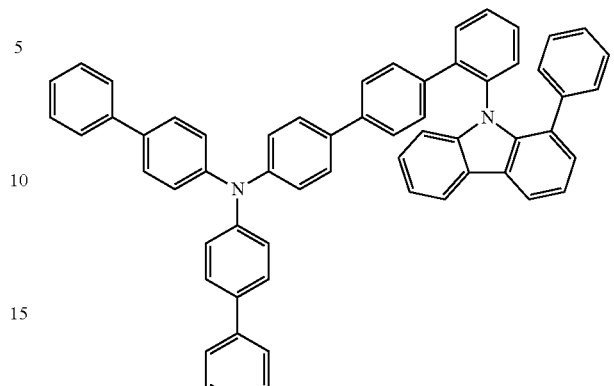
A2-58
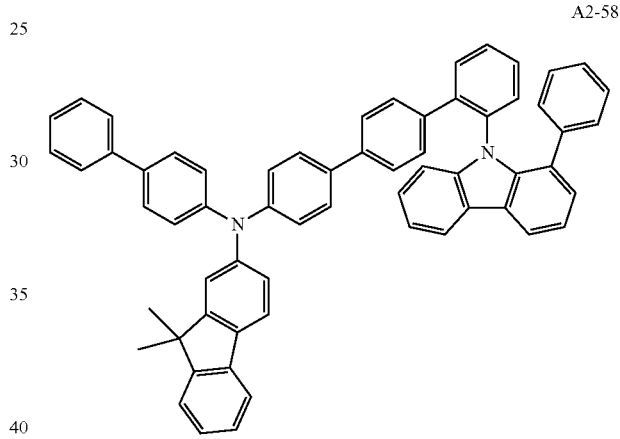
A2-59
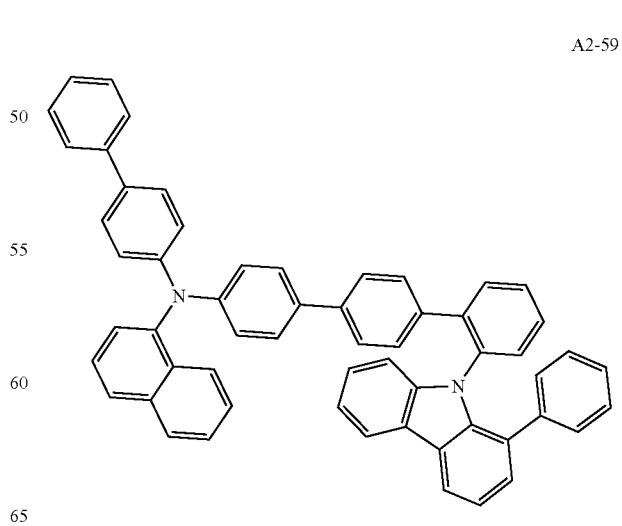

A2-60
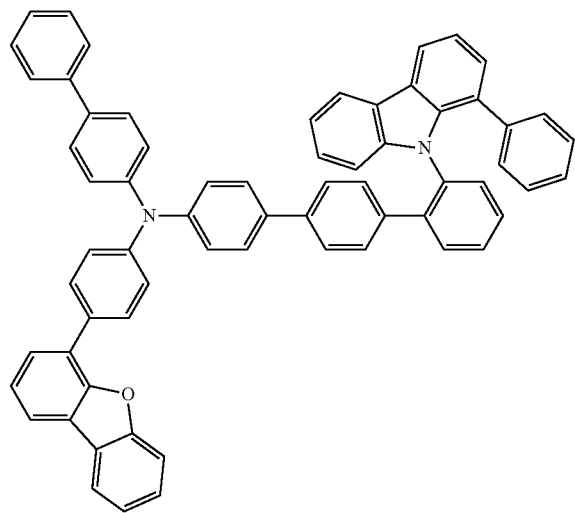
A2-61
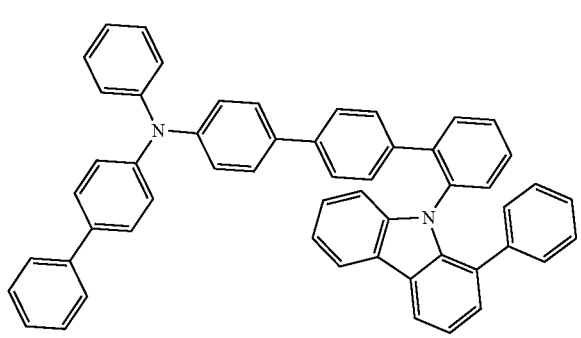
A2-62
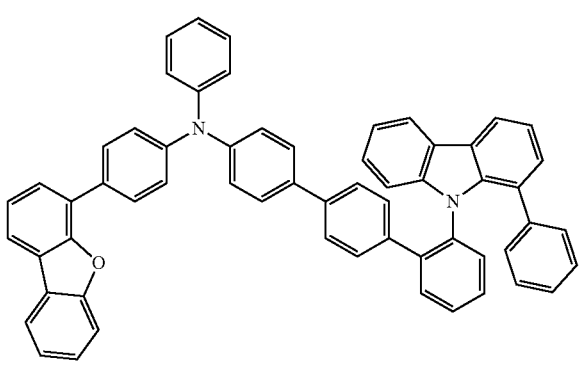
A3-1
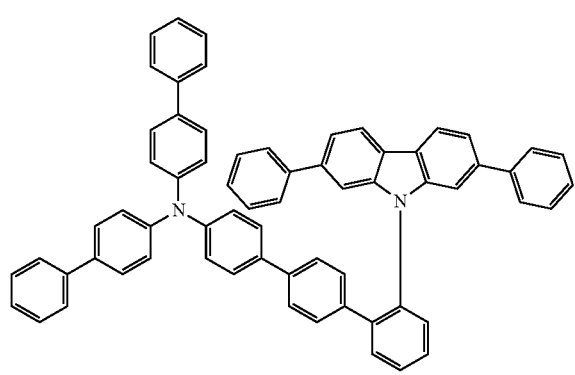
A3-2
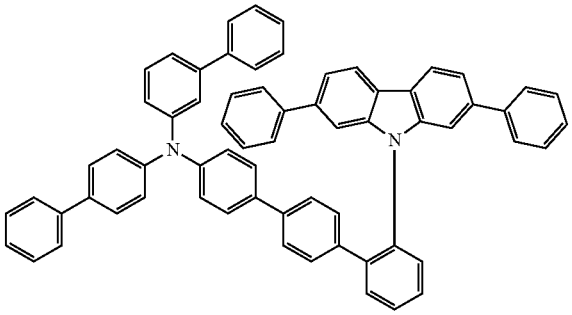
A3-3
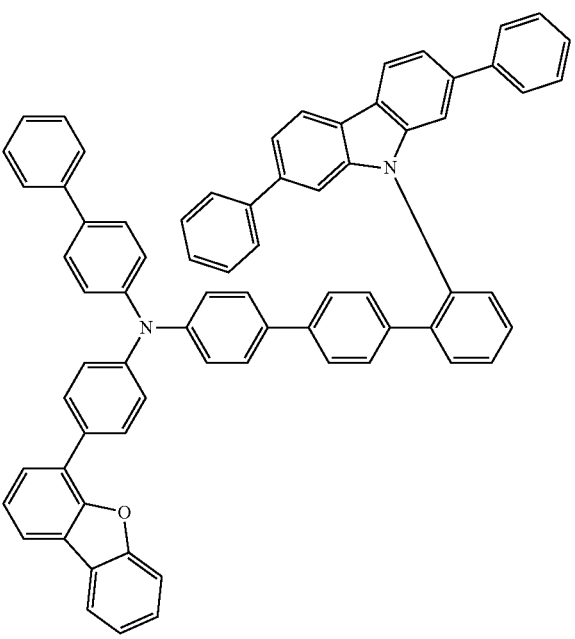
A3-4
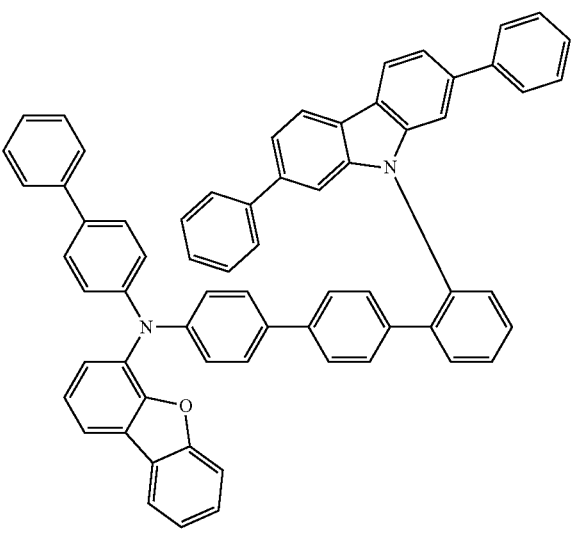

A3-5
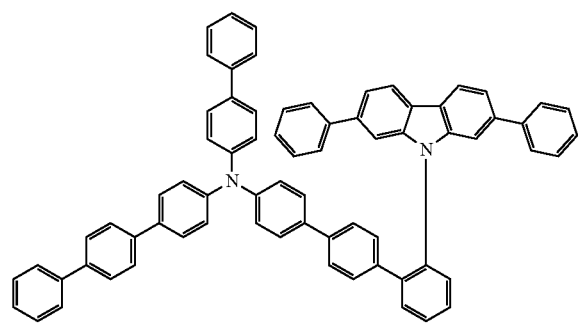
A3-6
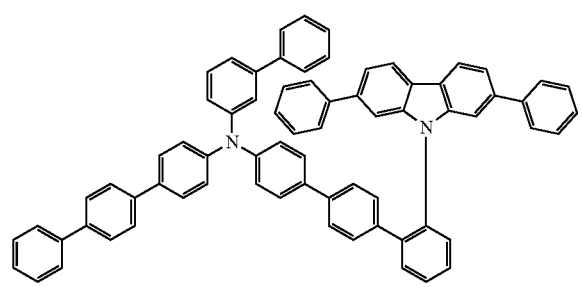
A3-7
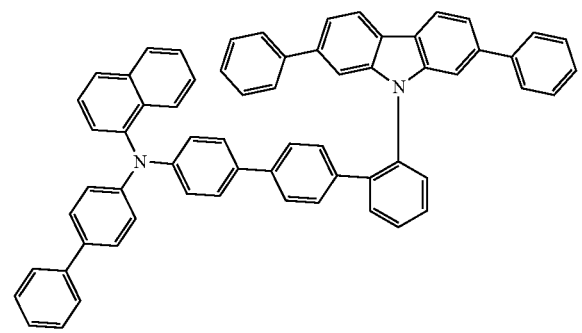
A3-8
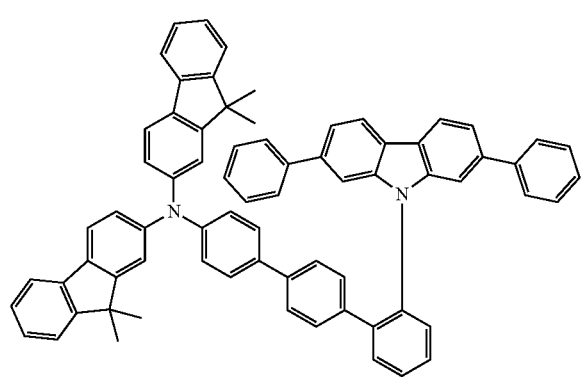
A3-9
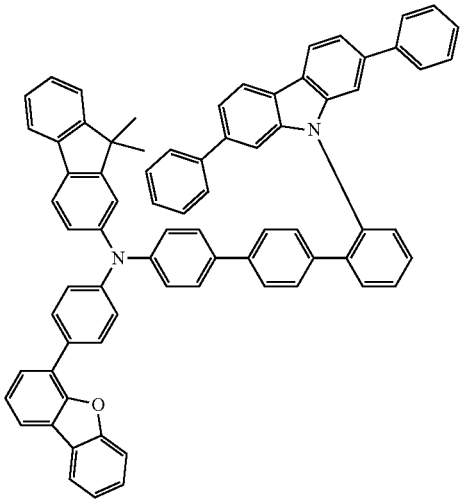
A3-10
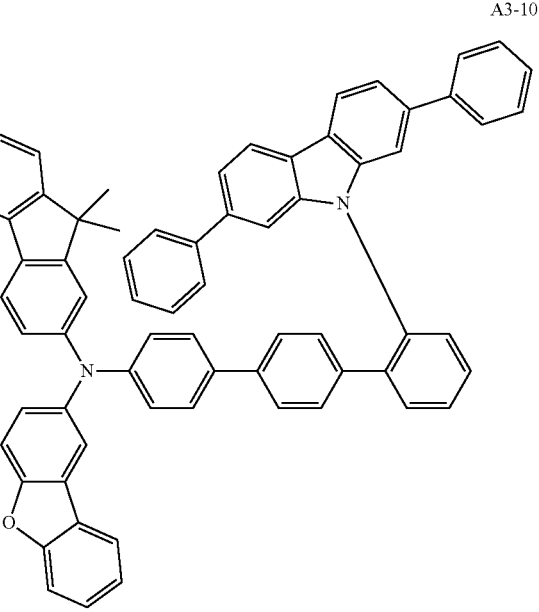
A3-11
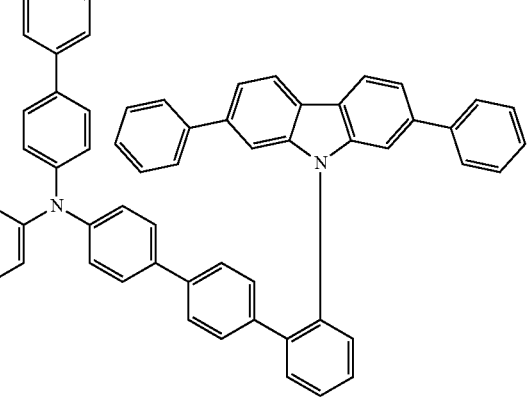

A3-12
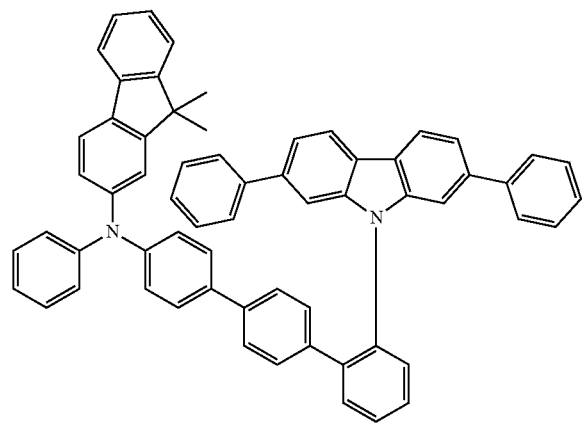
A3-13
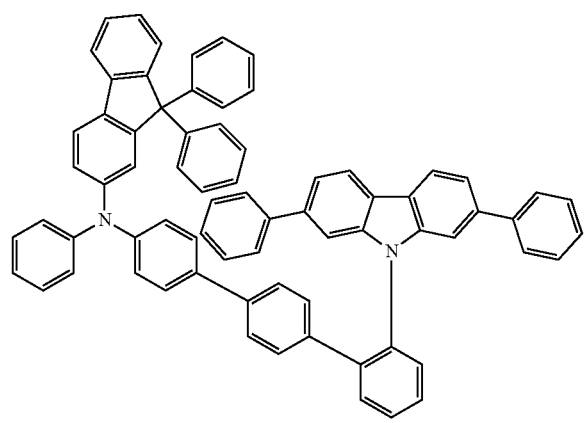
A3-14
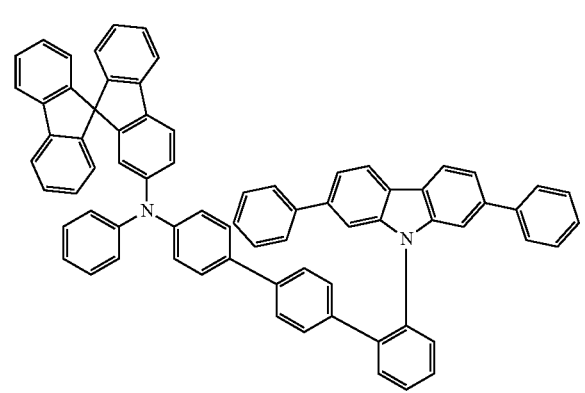
A3-15
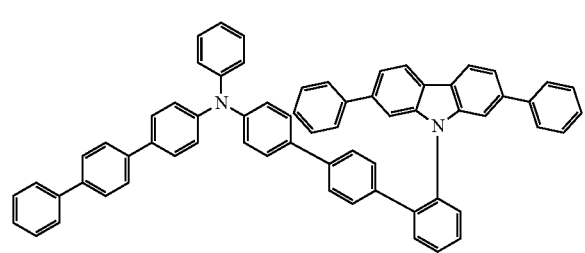
A3-16
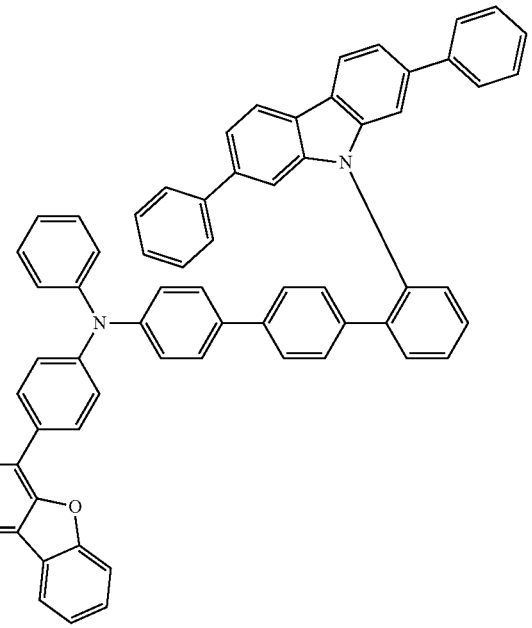
A3-17
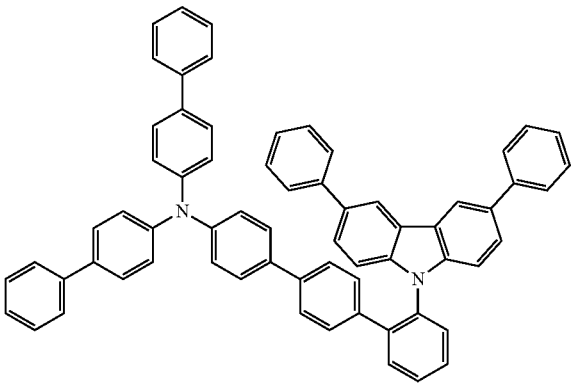
A3-18
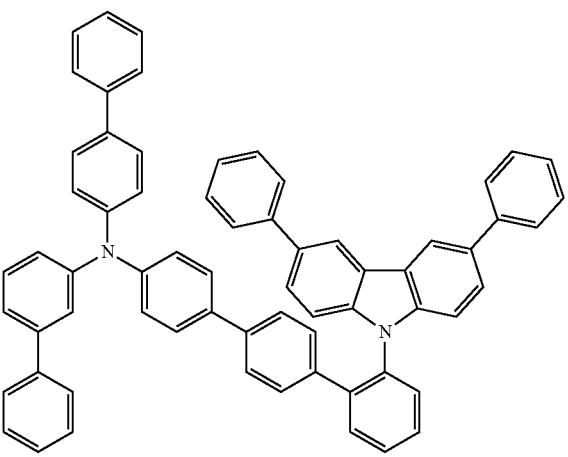

A3-19
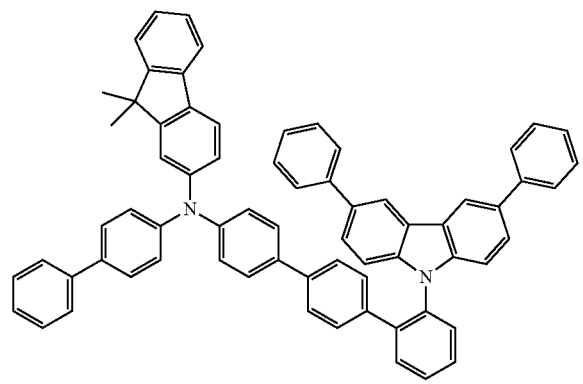
A3-22
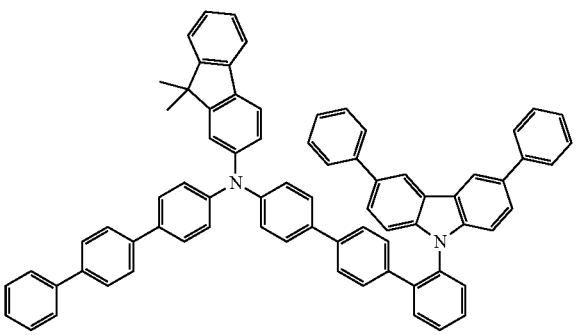
A3-20
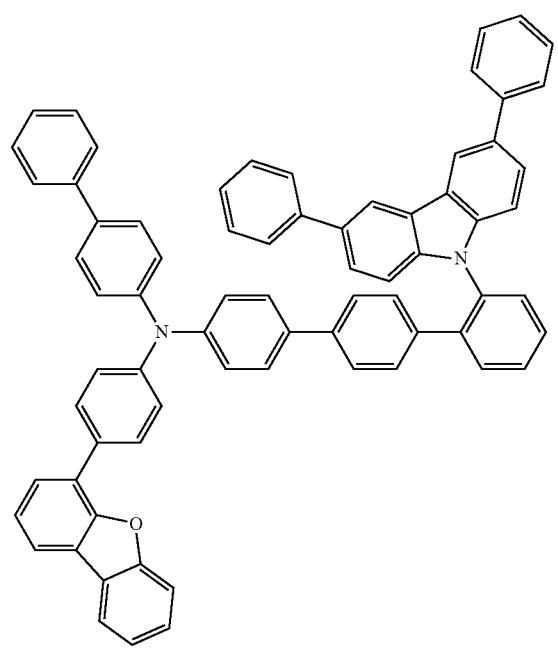
A3-23
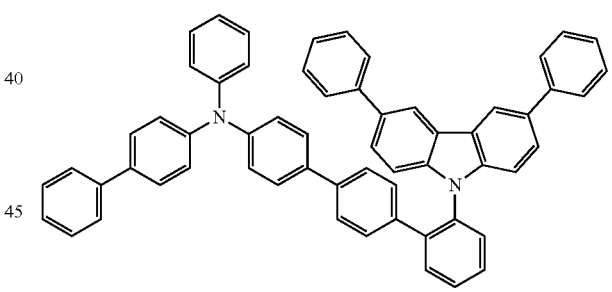
A3-24
A3-21
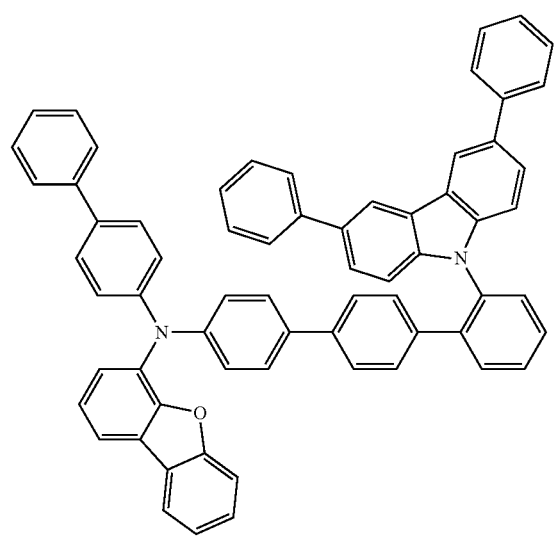
A3-25
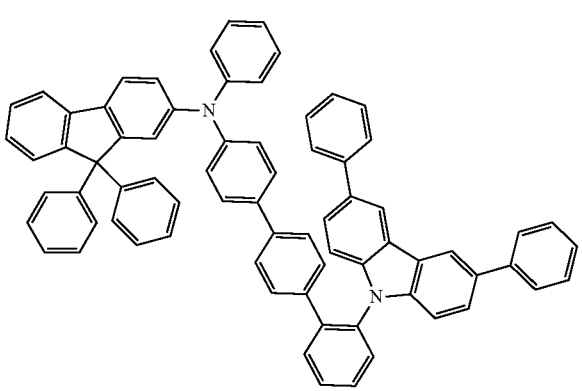

A3-26
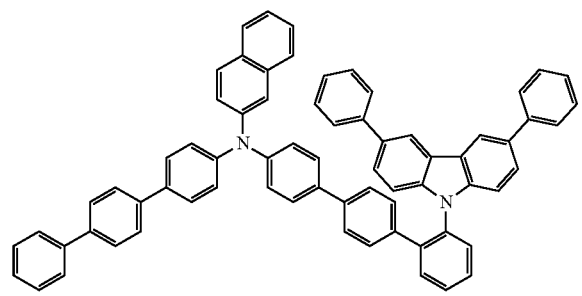
A3-27
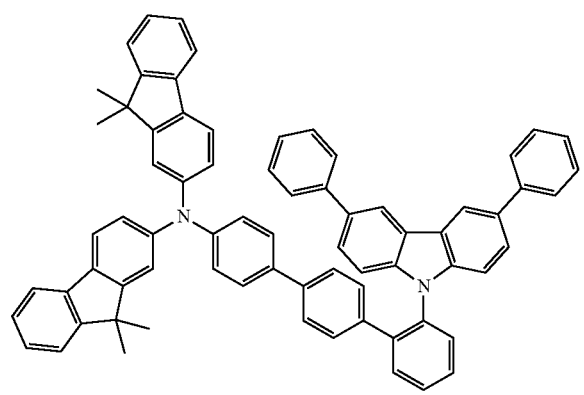
A3-28
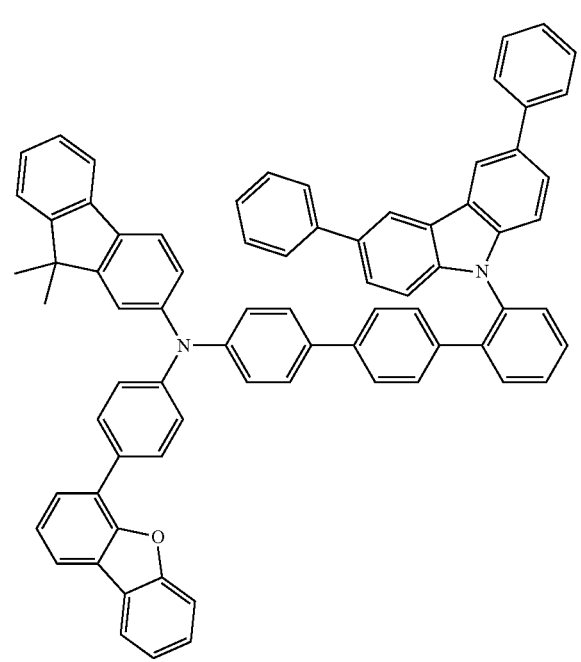
A3-29
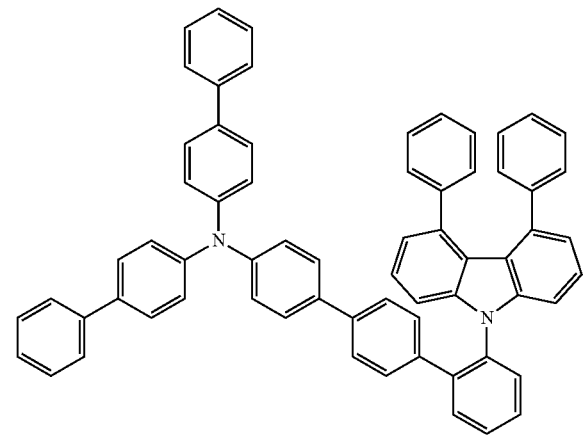
A3-30
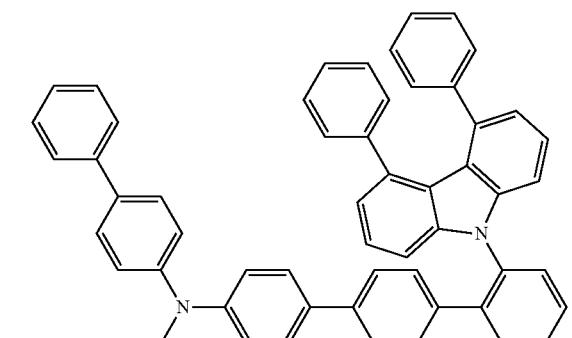
A3-31
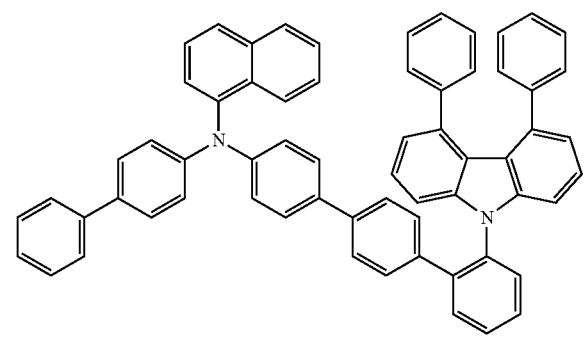

-continued
A3-32
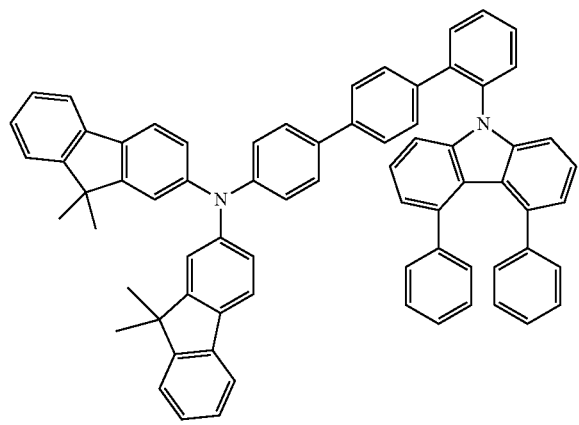
A3-33
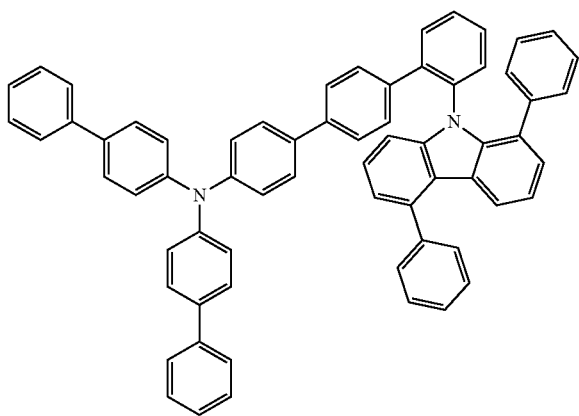
A3-34
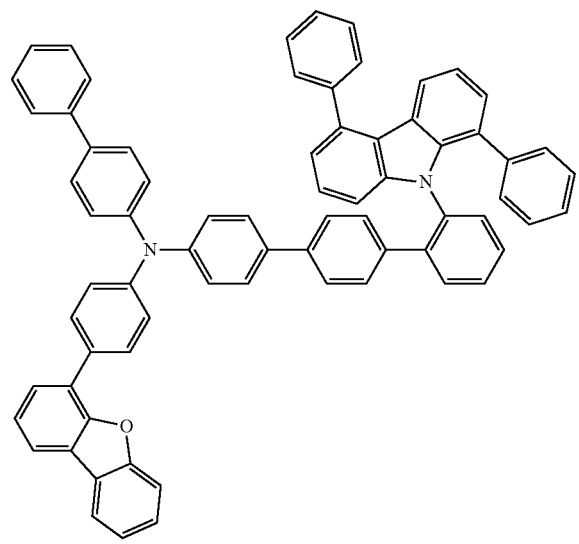
A3-35
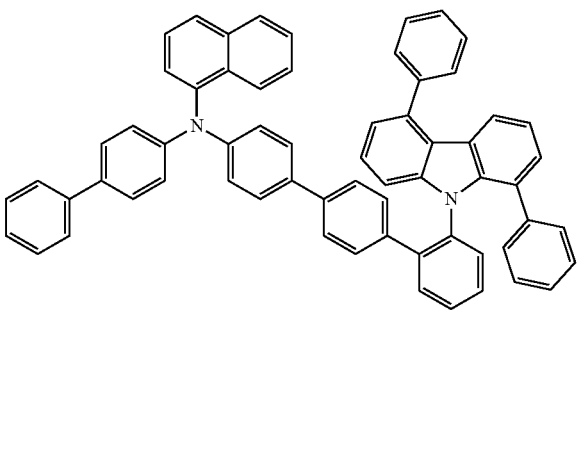
A3-36
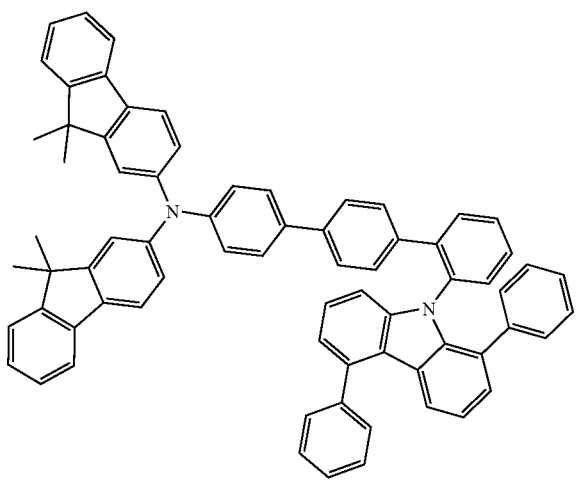
A3-37
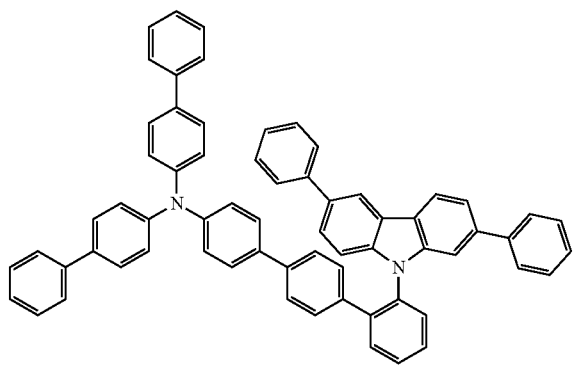

A3-38
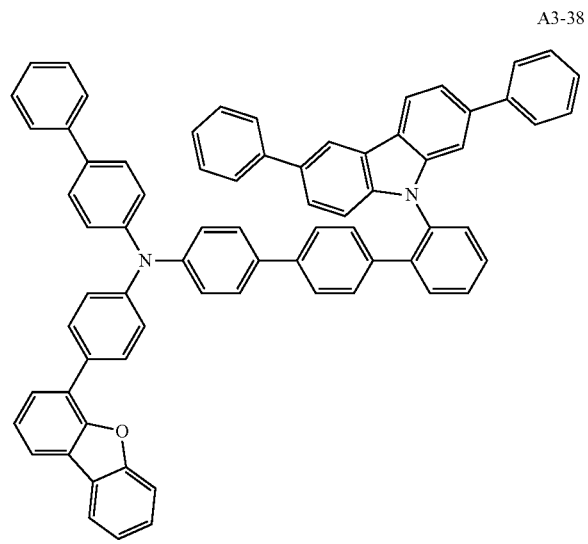
A4-1
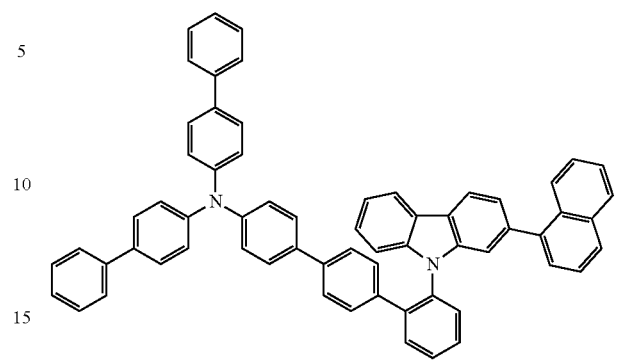
A3-39
A4-2
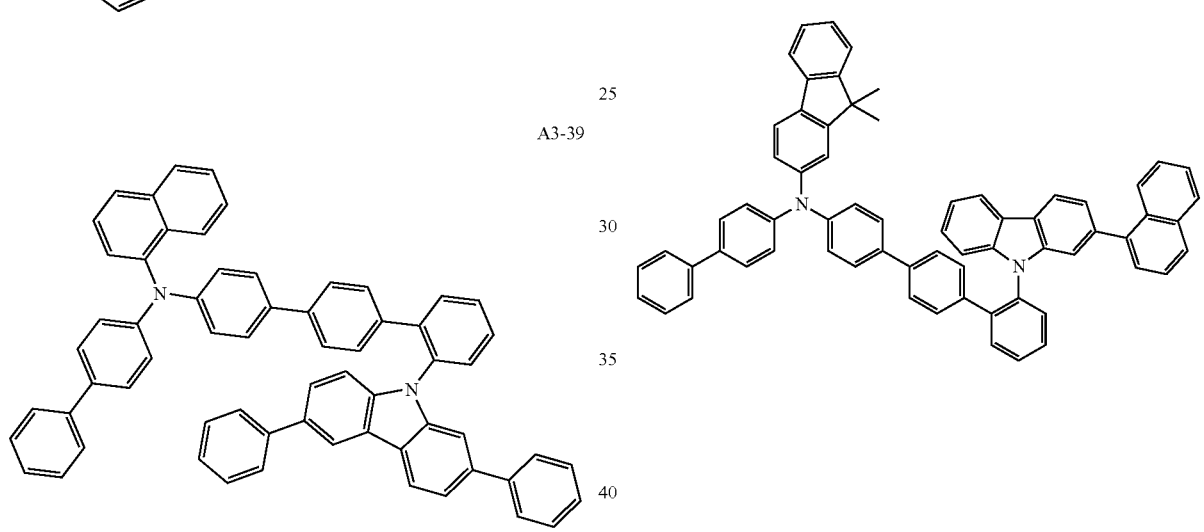
A3-40
A4-3
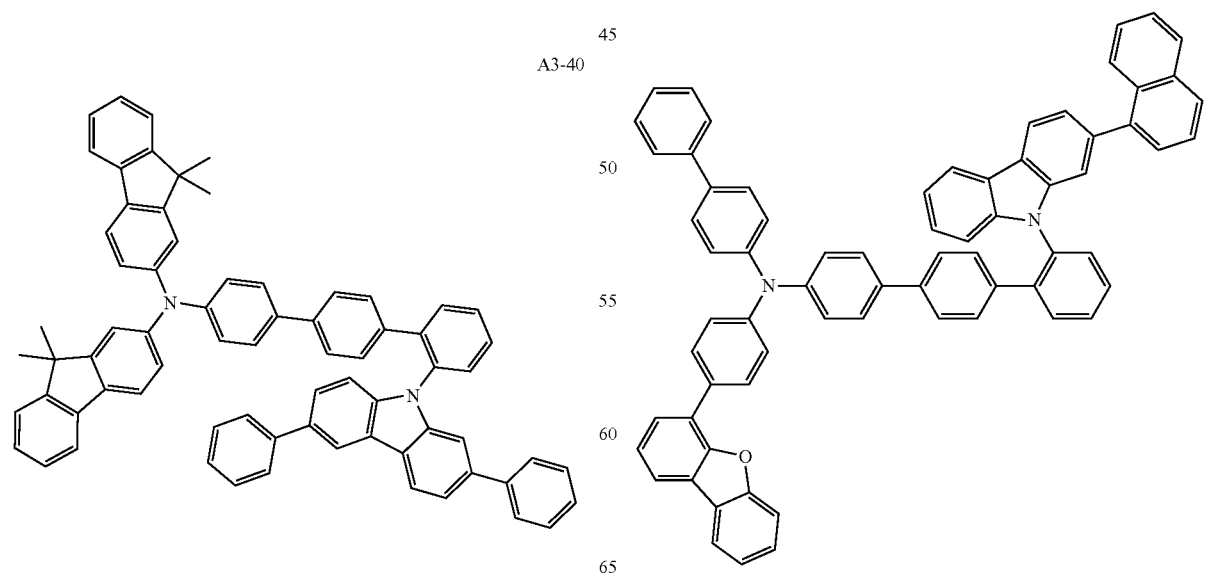

A4-4
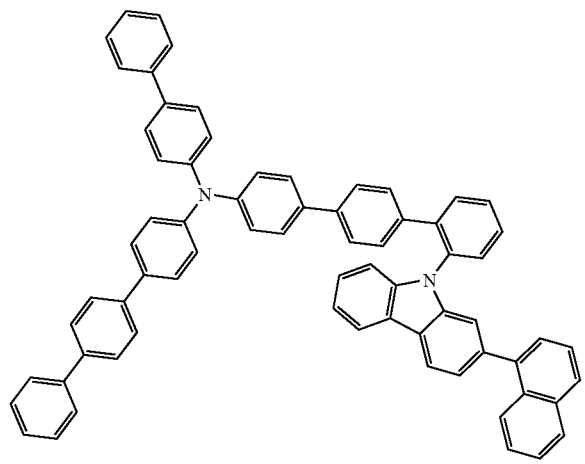
A4-5
A4-6
A4-7
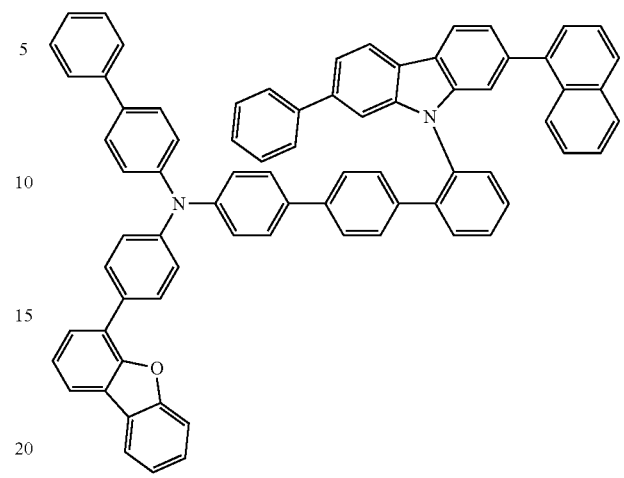
A4-8
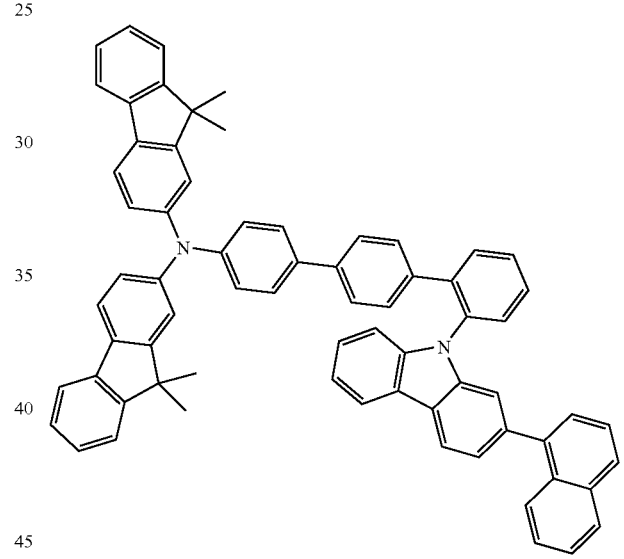
A4-9
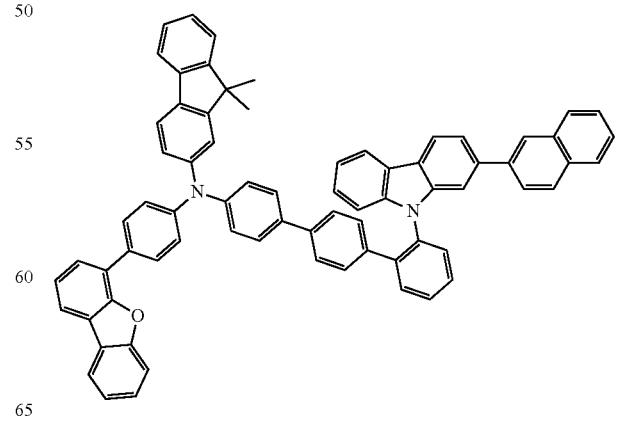

A4-10
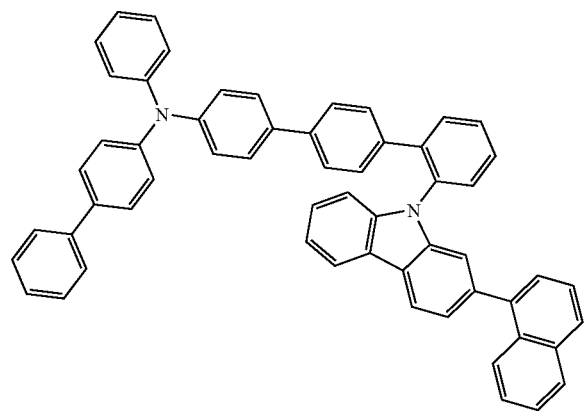
A4-13
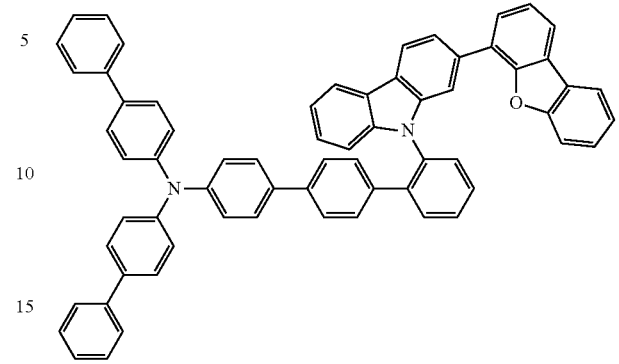
A4-11
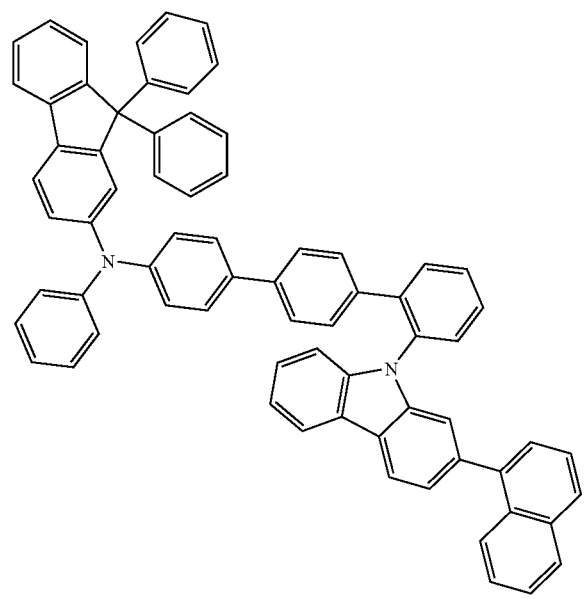
A4-14
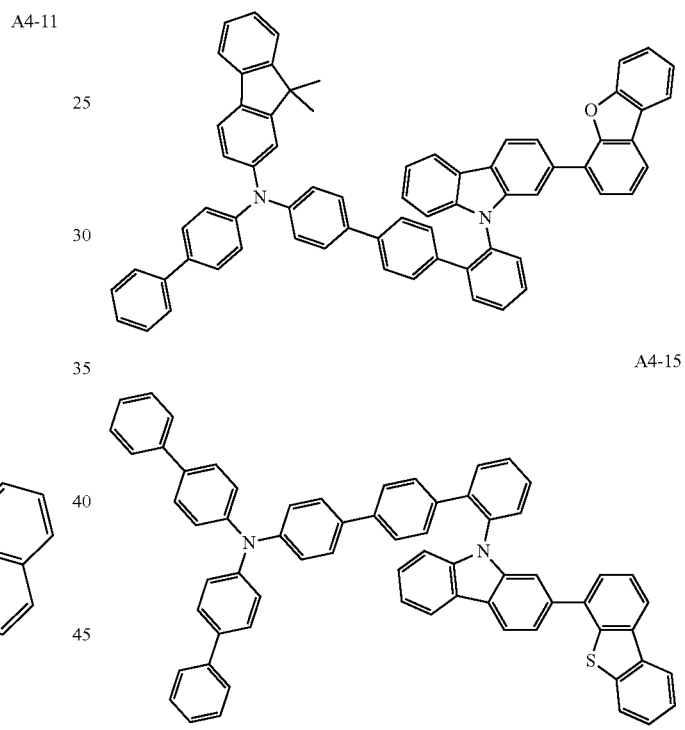
A4-15
A4-12
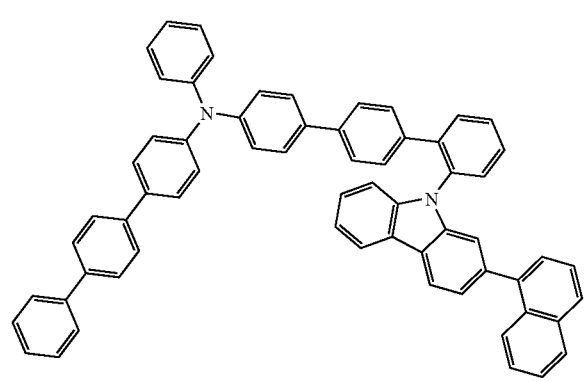
A4-16
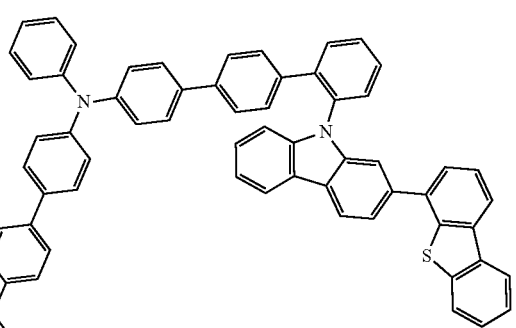

-continued
A4-17
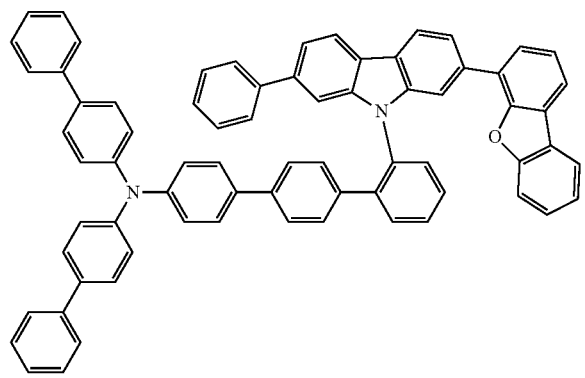
A4-18
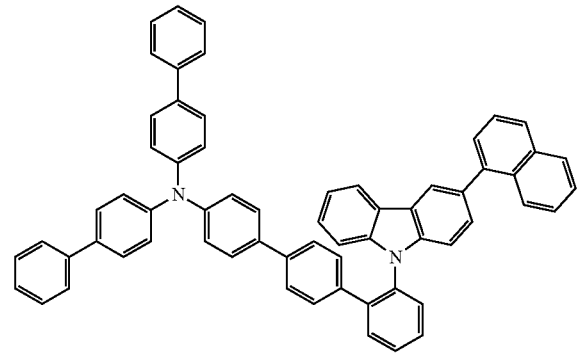
A4-19
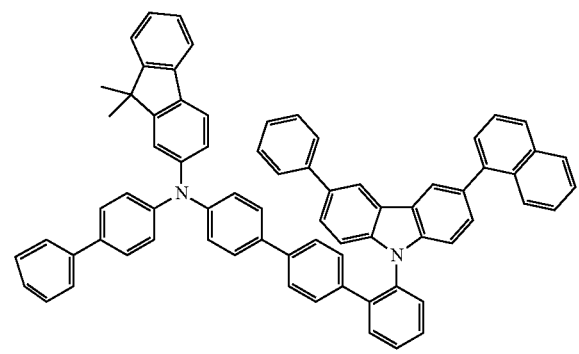
A-20
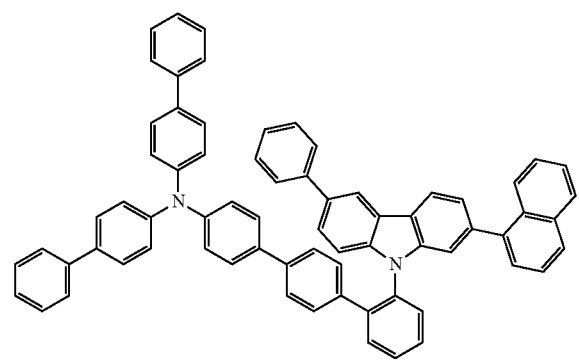
-continued
A4-21
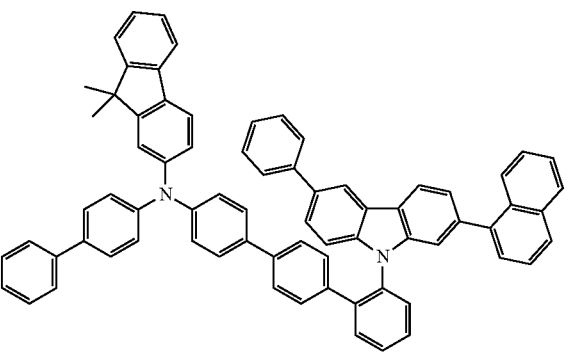
A4-22
A4-23
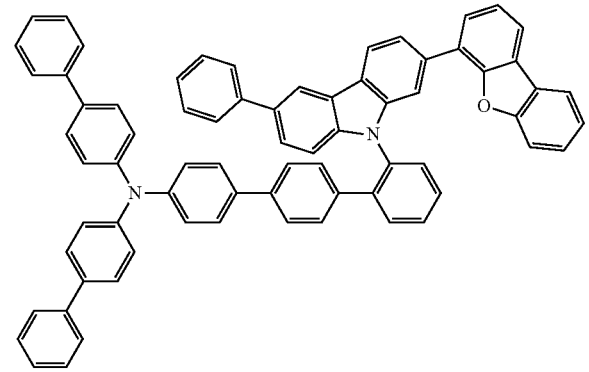

A4-24
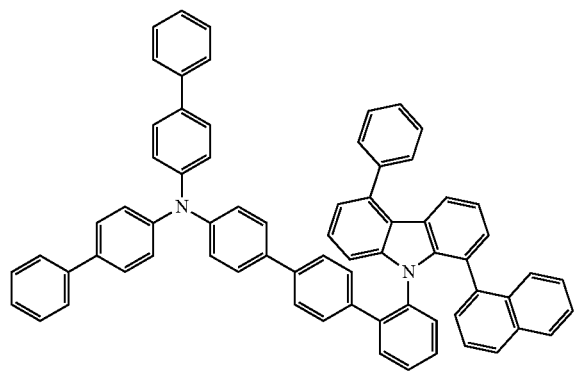
A4-27
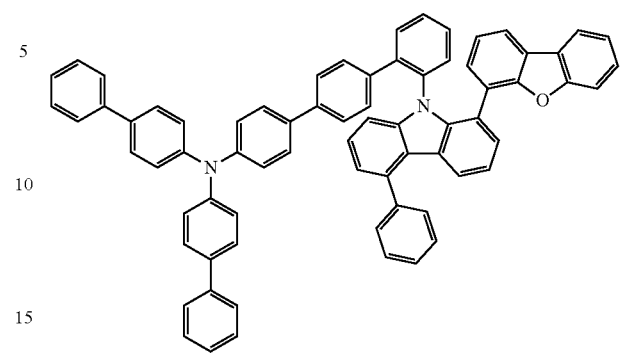
A4-25
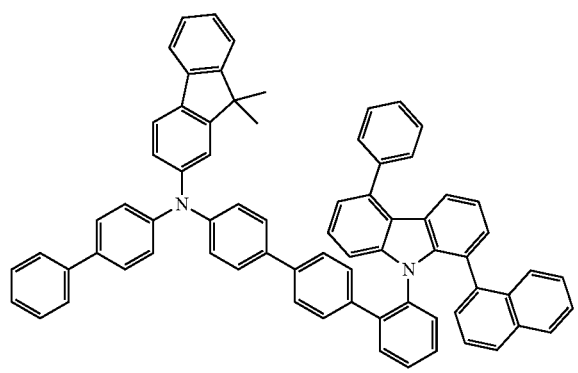
A4-28
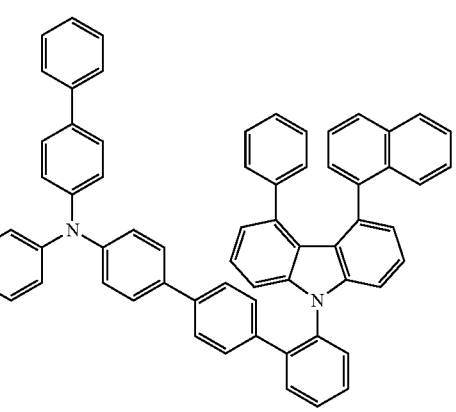
A4-26
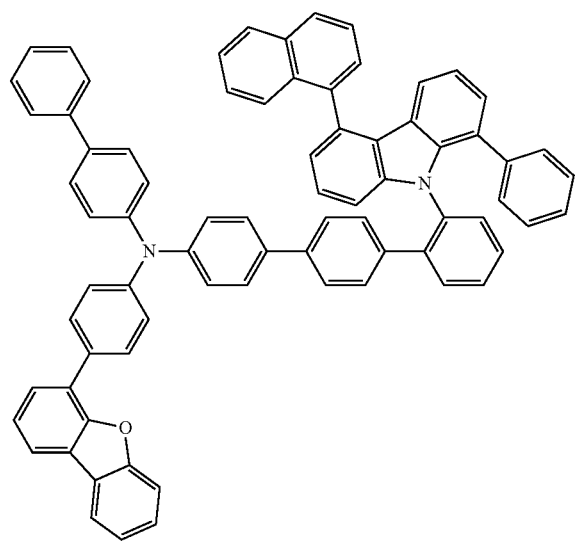
A4-29
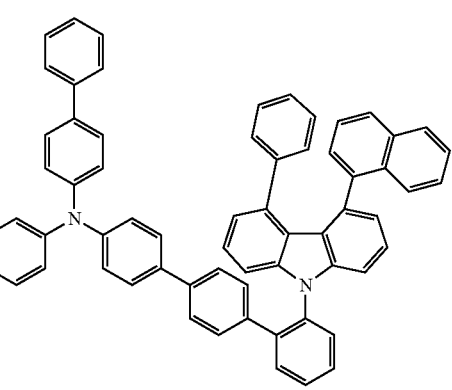

A4-30

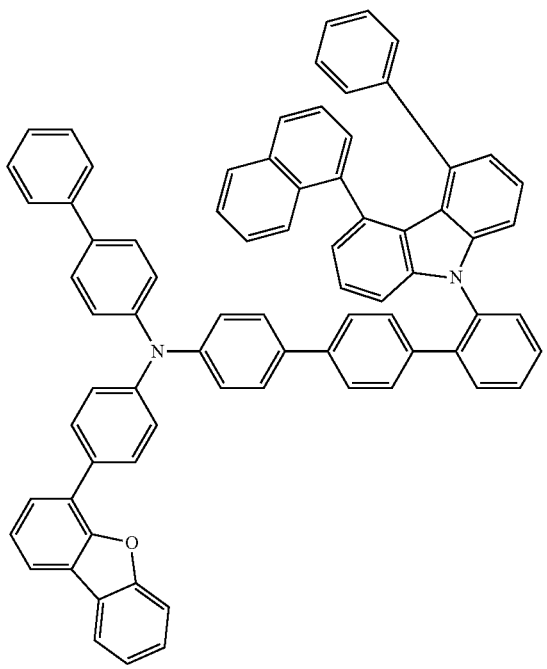

A4-31

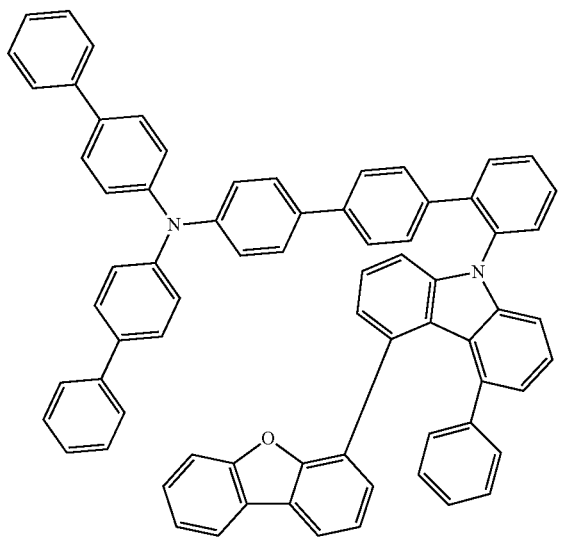

The compound or the composition described above may be for an organic optoelectronic diode, and the compound for an organic optoelectronic diode or the composition for an organic optoelectronic diode may be formed using a dry film-forming method such as chemical vapor deposition.

Hereinafter, an organic optoelectronic diode using the compound for an organic optoelectronic diode or the composition for an organic optoelectronic diode described above will be described.

The organic optoelectronic diode is not particularly limited as long as it is a device capable of interconverting electrical energy and light energy, and examples thereof may include an organic photoelectric diode, an organic light emitting diode, an organic solar cell, an organic photo conductor drum and the like.

Another embodiment of the present application provides an organic light emitting diode including a first electrode; a second electrode provided opposite to the first electrode; and one or more organic material layers provided between the first electrode and the second electrode, wherein one or more layers of the organic material layers include the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting diode may be a blue organic light emitting diode, and the heterocyclic compound according to Chemical Formula 1 may be used as a material of the blue organic light emitting diode.

In one embodiment of the present application, the organic light emitting diode may be a green organic light emitting diode, and the heterocyclic compound according to Chemical Formula 1 may be used as a material of the green organic light emitting diode.

In one embodiment of the present application, the organic light emitting diode may be a red organic light emitting diode, and the heterocyclic compound according to Chemical Formula 1 may be used as a material of the red organic light emitting diode.

The organic light emitting diode of the present disclosure may be manufactured using common organic light emitting diode manufacturing methods and materials except that one or more organic material layers are formed using the heterocyclic compound described above.

The heterocyclic compound may be formed into an organic material layer using a solution coating method as well as a vacuum deposition method when manufacturing the organic light emitting diode. Herein, the solution coating method means spin coating, dip coating, inkjet printing, screen printing, a spray method, roll coating and the like, but is not limited thereto.

Herein, another example of the organic light emitting diode, one example of the organic optoelectronic diode, will be described with reference to accompanying drawings.

FIGS. 1 to 3 illustrate a lamination order of electrodes and organic material layers of an organic light emitting diode according to one embodiment of the present application. However, the scope of the present application is not limited to these diagrams, and structures of organic optoelectronic diodes known in the art may also be used in the present application.

FIG. 1 illustrates an organic light emitting diode in which an anode (200), an organic material layer (300) and a cathode (400) are consecutively laminated on a substrate (100). However, the structure is not limited to such a structure, and as illustrated in FIG. 2, an organic light emitting diode in which a cathode, an organic material layer and an anode are consecutively laminated on a substrate may also be obtained.

FIG. 3 illustrates a case of the organic material layer being a multilayer. The organic light emitting diode according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further included.

In the organic light emitting diode, the compound represented by Chemical Formula 1 may be used as a material of an electron transfer layer, a hole transfer layer, a light emitting layer, and the like.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene](PEDT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among N-type host materials or P-type host materials may be selected, and used as a host material of a light emitting layer.

The organic light emitting diode according to one embodiment of the present application may be a top-emission type, a bottom-emission type or a dual-emission type depending on the materials used.

Hereinafter, the embodiments described above will be described in more detail through examples. However, the following examples are for illustrative purposes only and do not limit the scope of a right.

Starting materials and reaction materials used in the following examples and synthesis examples are, unless particularly mentioned otherwise, purchased from Sigma-Aldrich, TCI, Tokyo chemical industry or P&H tech, or synthesized using known methods.

Preparation of Compound for Organic Optoelectronic Diode

[Preparation Example A1-1] Synthesis of Intermediate A(1)

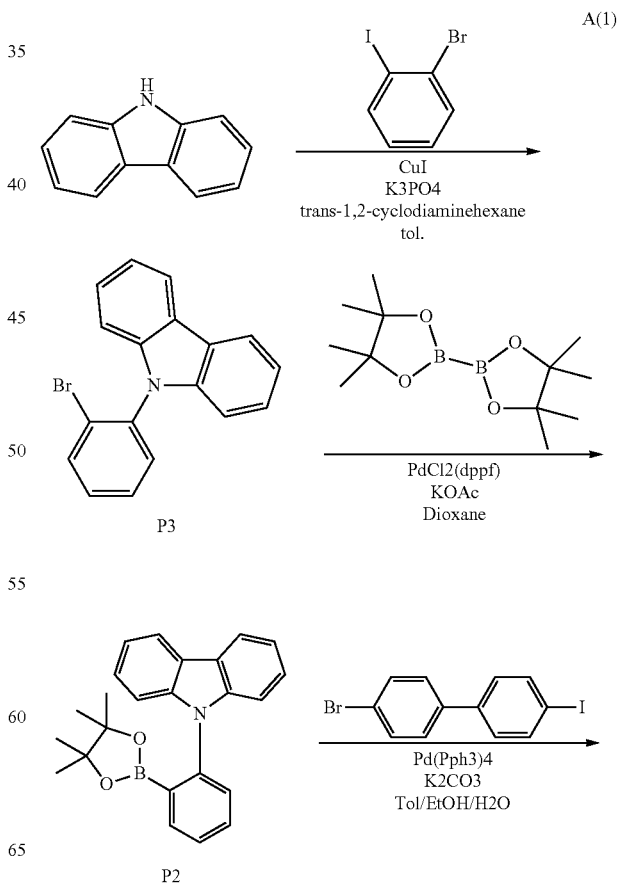

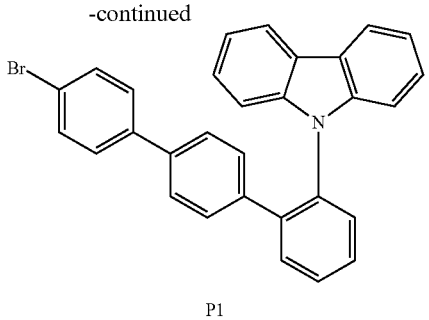

P1

Synthesis of Intermediate A(1)-P3

Carbazole (40 g, 1 eq.), 1-bromo-2-iodobenzene (70 g, 1.5 eq.), CuI (6.3 g, 0.2 eq.), $K_3PO_4$ (70 g, 2 eq.), trans-1,2-cyclohexanediamine (19 g, 1 eq.) and toluene (600 ml) were introduced to a 1-neck-round bottom flask (1-neck-r.b.f), and stirred for 4 hours.

The reaction solution completed with the stirring was filtered only with methylene chloride (MC), and then column separated to obtain P3 (approximately 65 g).

Step yield=96%

Synthesis of Intermediate A(1)-P2

P3 (65 g, 1 eq.), bis(pinacolato)diboron (65 g 1.5 eq.), $PdCl_2$(dppf) (11 g, 0.1 eq.), KOAc (50 g, 3 eq.) and dioxane (800 ml) were introduced to a 1-neck-round bottom flask (1-neck-r.b.f), and stirred for 6 hours.

The reaction solution completed with the stirring was filtered using silica/celite to obtain P2 (approximately 60 g).

Step yield=83%

Synthesis of Intermediate A(1)-P1

P2 (60 g, 1 eq.), 4-bromo-4'-iodo-1,1'-biphenyl (63 g, 1.3 eq.), Pd(PPh$_3$)$_4$ (7.8 g, 0.05 eq.), $K_2CO_3$ (28 g, 1.5 eq.), toluene (600 ml), ethanol (100 ml) and $H_2O$ (100 ml) were introduced to a 1-neck-round bottom flask (1-neck-r.b.f), and stirred for 4 hours.

The reaction solution completed with the stirring was hot filtered twice only with methylene chloride (MC) to obtain P1 (33 g).

Step yield=54%

[Preparation Example A1-2] Synthesis of Intermediate A(2)

Intermediate A(2) was synthesized in the same manner as in Synthesis of Intermediate A(1)-P3 in all steps except that 2-phenyl-carbazole was used instead of carbazole.

[Preparation Example A1-3] Synthesis of Intermediate A(3)

Intermediate A(3) was synthesized in the same manner as in Synthesis of Intermediate A(1)-P3 in all steps except that 3-phenyl-carbazole was used instead of carbazole.

[Preparation Example A1-4] Synthesis of Intermediate A(4)

Intermediate A(4) was synthesized in the same manner as in Synthesis of Intermediate A(1)-P3 in all steps except that 4-phenyl-carbazole was used instead of carbazole.

[Preparation Example A1-5] Synthesis of Intermediate A(5)

Intermediate A(5) was synthesized in the same manner as in Synthesis of Intermediate A(1)-P3 in all steps except that 1-phenyl-carbazole was used instead of carbazole.

[Preparation Example A1-6] Synthesis of Intermediate A(6)

Intermediate A(6) was synthesized in the same manner as in Synthesis of Intermediate A(1)-P3 in all steps except that 2,7-phenyl-carbazole was used instead of carbazole.

[Preparation Example A1-7] Synthesis of Intermediate A(7)

Intermediate A(7) was synthesized in the same manner as in Synthesis of Intermediate A(1)-P3 in all steps except that 3,6-phenyl-carbazole was used instead of carbazole.

[Preparation Example A1-8] Synthesis of Intermediate A(8)

Intermediate A(8) was synthesized in the same manner as in Synthesis of Intermediate A(1)-P3 in all steps except that 2-(naphthalen-1-yl)-9H-carbazole was used instead of carbazole.

[Preparation Example A1-9] Synthesis of Intermediate A(9)

Intermediate A(9) was synthesized in the same manner as in Synthesis of Intermediate A(1)-P3 in all steps except that 2-(dibenzo[b,d]furan-4-yl)-9H-carbazole was used instead of carbazole.

[Preparation Example A1-10] Synthesis of Intermediate A(10)

Intermediate A(10) was synthesized in the same manner as in Synthesis of Intermediate A(1)-P3 in all steps except that dibenzo[b,d]thiophen-4-yl)-9H-carbazole was used instead of carbazole.

[Preparation Example 1-a] Synthesis of Biphenylamine

4-Bromo-benzenamine (30 g, 1 eq.), phenylboronic acid (25.52 g, 1.5 eq.), Pd(PPh$_3$)$_4$ (10 g, 0.05 eq.), $K_2CO_3$ (36 g, 1.5 eq.), toluene (600 ml), EtOH (100 ml) and $H_2O$ (100 ml) were introduced to a 1-neck-round bottom flask (1-neck-r.b.f), and stirred for 3 hours.

The reaction solution completed with the stirring was silica filtered using methylene chloride (MC) and hexane (Hx) in a ratio of MC:Hx=1:5 to obtain biphenylamine (19 g).

Step yield=64%

[Preparation Example 1-b] Synthesis of N-[1,1'-biphenyl]-3-yl[1,1'-biphenyl]-4-amine Biphenylamine (15 g, 1 eq.), 3-bromobiphenyl (25 g, 1.2 eq.), Pd$_2$(dba)$_3$ (2.4 g, 0.03 eq.), t-BuONa (12.5 g, 1.5 eq.), t-Bu$_3$P (1.05 g, 0.06 eq.) and toluene (400 ml) were introduced to a 1-neck-round bottom flask (1-neck-r.b.f), and stirred for 4 hours.

The reaction solution completed with the stirring was column separated using methylene chloride (MC) and hexane (Hx) in a ratio of MC:Hx=1:5 to obtain N-[1,1'-biphenyl]-3-yl[1,1'-biphenyl]-4-amine (18 g). (Step yield=71%)

[Preparation Example 1-c] Synthesis of N-[4-(4-dibenzofuranyl)phenyl]-[1,1'-biphenyl]-4-amine Biphenylamine (19 g, 1.3 eq.), 4-(4-bromophenyl)-dibenzofuran (28 g, 1 eq.), Pd$_2$(dba)$_3$ (2.4 g, 0.03 eq.), t-BuONa (12.5 g, 1.5 eq.), t-Bu$_3$P (1.05 g, 0.06 eq.) and toluene (400 ml) were introduced to a 1-neck-round bottom flask (1-neck-r.b.f), and stirred for 4 hours.

The reaction solution completed with the stirring was filtered to obtain solids (28 g). The solids were hot filtered using toluene to obtain N-[4-(4-dibenzofuranyl)phenyl]-[1,1'-biphenyl]-4-amine (18 g). (Step yield=51%) [Preparation Example 1-d] Synthesis of N-[4-(3-dibenzofuranyl)phenyl]-[1,1'-biphenyl]-4-amine N-[4-(3-dibenzofuranyl)phenyl]-[1,1'-biphenyl]-4-amine was synthesized in the same manner as in the synthesis method of Preparation Example 1-c except that 4-(4-bromophenyl)-dibenzofuran was changed to 3-(4-bromophenyl)-dibenzofuran.

[Preparation Example 1-e] Synthesis of N-[4-(2-dibenzofuranyl)phenyl]-[1,1'-biphenyl]-4-amine N-[4-(2-dibenzofuranyl)phenyl]-[1,1'-biphenyl]-4-amine was synthesized in the same manner as in the synthesis method of Preparation Example 1-c except that 4-(4-bromophenyl)-dibenzofuran was changed to 2-(4-bromophenyl)-dibenzofuran.

[Preparation Example 1-f] Synthesis of N-([1,1'-biphenyl]-3-yl)dibenzo[b,d]furan-4-amine Dibenzo[b,d]furan-4-amine (13 g, 1 eq.), 3-bromobiphenyl (25 g, 1.2 eq.), Pd$_2$(dba)$_3$ (2.4 g, 0.03 eq.), t-BuONa (12.5 g, 1.5 eq.), t-Bu$_3$P (1.05 g, 0.06 eq.) and toluene (400 ml) were introduced to a 1-neck-round bottom flask (1-neck-r.b.f), and stirred for 3 hours.

The reaction solution completed with the stirring was column separated using methylene chloride (MC) and hexane (Hx) in a ratio of MC:Hx=1:5 to obtain N-([1,1'-biphenyl]-3-yl)dibenzo[b,d]furan-4-amine (16 g). (Step yield=73%)

[Preparation Example 1-g] Synthesis of N-(4-(dibenzo[b,d]furan-4-yl)phenyl)-9,9-dimethyl-9H-fluoren-2-amine 9,9-Dimethyl-9H-fluoren-2-amine (10 g, 1 eq.), 4-(4-bromophenyl)dibenzo[b,d]furan (28 g, 1.2 eq.), Pd$_2$(dba)$_3$ (2.4 g, 0.03 eq.), t-BuONa (12.5 g, 1.5 eq.), t-Bu$_3$P (1.05 g, 0.06 eq.) and toluene (400 ml) were introduced to a 1-neck-round bottom flask (1-neck-r.b.f), and stirred for 4 hours.

9,9-Dimethyl-9H-fluoren-2-amine (10 g, 1 eq.), 4-(4-bromophenyl)dibenzo[b,d]furan (28 g, 1.2 eq.), Pd$_2$ (dba)$_3$ (2.4 g, 0.03 eq.), t-BuONa (12.5 g, 1.5 eq.), t-Bu$_3$P (1.05 g, 0.06 eq.), and toluene (400 ml) were introduced to a 1-neck-round bottom flask (1-neck-r.b.f), and stirred for 4 hours.

[Preparation Example 1-h] Synthesis of 2-(Naphthalen-1-yl)-9H-carbazole

2-Bromo-9H-carbazole (7.5 g, 1 eq.), naphthalen-1-ylboronic acid (8.2 g, 1.65 eq.), Pd(PPh$_3$)$_4$ (2 g, 0.05 eq.), K$_2$CO$_3$ (13 g, 3 eq.), toluene (150 ml), EtOH (50 ml) and H$_2$O (50 ml) were introduced to a 1-neck-round bottom flask (1-neck-r.b.f), and stirred for 5 hours.

The reaction solution completed with the stirring was filtered to obtain solids. The solids were washed with MeOH, and 2-(naphthalen-1-yl)-9H-carbazole (8 g) was obtained. (Step yield=89%)

[Preparation Example 1-i] Synthesis of 2-(Dibenzo[b,d]furan-4-yl)-9H-carbazole 2-(Dibenzo[b,d]furan-4-yl)-9H-carbazole was synthesized in the same manner as in the synthesis method of Preparation Example 1-h except that naphthalen-1-ylboronic acid was changed to dibenzo[b,d]furan-4-ylboronic acid. (Step yield=95%)

[Preparation Example 1-j] Synthesis of 2-(Dibenzo[b,d]thiophen-4-yl)-9H-carbazole 2-(Dibenzo[b,d]thiophen-4-yl)-9H-carbazole was synthesized in the same manner as in the synthesis method of Preparation Example 1-h except that naphthalen-1-ylboronic acid was changed to dibenzo[b,d]thiophen-4-ylboronic acid. (Step yield=85%)

Synthesis of Compound A1-1

Intermediate A(1)-P1 (10 g, 1 eq.), bis(biphenyl)amine (8 g, 1.1 eq.), Pd(OAc)$_2$ (0.21 g, 0.05 eq.), t-BuONa (2.62 g, 1.5 eq.), t-Bu$_3$P (0.37 g, 0.1 eq.) and toluene (200 ml) were introduced to a 1-neck-round bottom flask (1-neck-r.b.f), and stirred for 1.5 hours.

The reaction solution completed with the stirring was filtered to obtain solids (approximately 11 g, step yield=75%). The solids were hot filtered using toluene to obtain a material of HPLC 99.96% (6 g).

The entire amount of the material was sublimation purified to obtain light yellow solid Compound A1-1 (3.1 g).

Compounds of the following Table 1 were synthesized in the same manner as in the method of Synthesis of Compound A1-1 except that alternative compounds of the following Table 1 were used instead of bis(biphenyl)amine.

TABLE 1
| Compound No. | Alternative compound | yield |
|---|---|---|
| A1-2 | 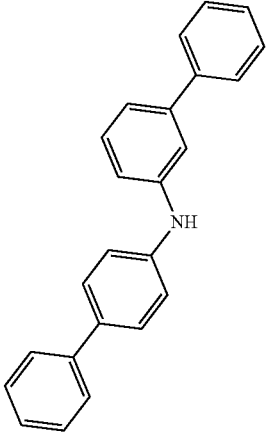 [SMILES: c1ccc(-c2ccc(Nc3cccc(-c4ccccc4)c3)cc2)cc1] | 64% |
| A1-6 | 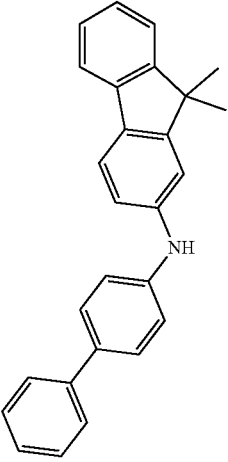 [SMILES: CC1(C)c2ccccc2-c2ccc(Nc3ccc(-c4ccccc4)cc3)cc21] | 65% |
| A1-7 | 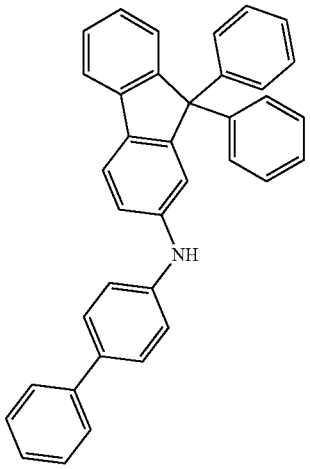 [SMILES: c1ccc(-c2ccc(Nc3ccc4c(c3)C(c3ccccc3)(c3ccccc3)c3ccccc3-4)cc2)cc1] | 62% |
TABLE 1-continued
| Compound No. | Alternative compound | yield |
|---|---|---|
| A1-9 | 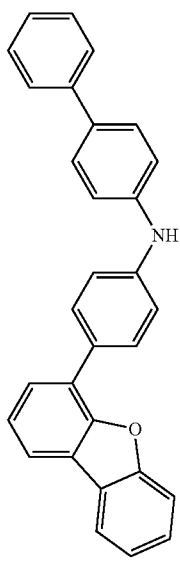 [SMILES: c1ccc(-c2ccc(Nc3ccc(-c4cccc5c4oc4ccccc45)cc3)cc2)cc1] | 75% |
| A1-10 | 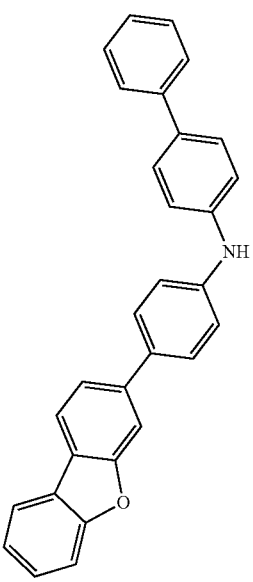 [SMILES: c1ccc(-c2ccc(Nc3ccc(-c4ccc5c(c4)oc4ccccc45)cc3)cc2)cc1] | 70% |

TABLE 1-continued

| Compound No. | Alternative compound | yield |
|---|---|---|
| A1-11 | | 77% |
| A1-15 | | 60% |
| A1-18 | | 47% |
| A1-29 | | 71% |
| A1-33 | | 58% |

TABLE 1-continued
| Compound No. | Alternative compound | yield |
|---|---|---|
| A1-34 | 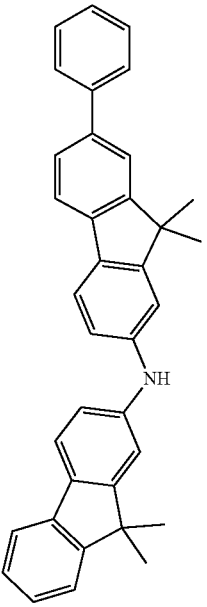 [SMILES: CC1(C)c2ccccc2-c2ccc(Nc3ccc4c(c3)C(C)(C)c3cc(-c5ccccc5)ccc3-4)cc21] | 59% |
| A1-41 | 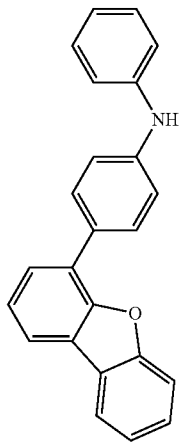 [SMILES: c1ccc(Nc2ccc(-c3cccc4c3oc3ccccc34)cc2)cc1] | 67% |
| A1-42 | 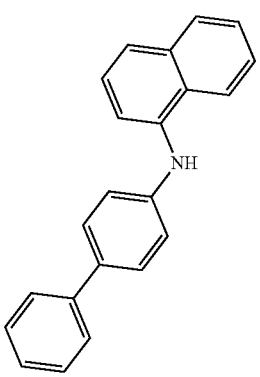 [SMILES: c1ccc(-c2ccc(Nc3cccc4ccccc34)cc2)cc1] | 60% |
| A1-45 | | 61% |
In addition, compounds of the following Table 2 were synthesized in the same manner as in the method of Synthesis of Compound A1-1 except that Intermediate I of the following Table 2 was used instead of Intermediate A(1)-P1, and Intermediate II of the following Table 2 was used instead of bis(biphenyl)amine.

TABLE 2
| Compound No. | Intermediate I | Intermediate II | yield |
|---|---|---|---|
| A2-1 | Intermediate A(2) | 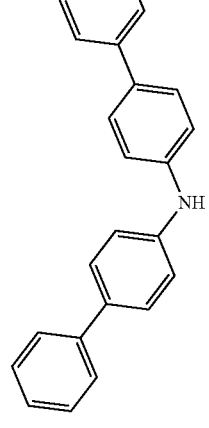 | 71% |
| A2-2 | Intermediate A(2) | 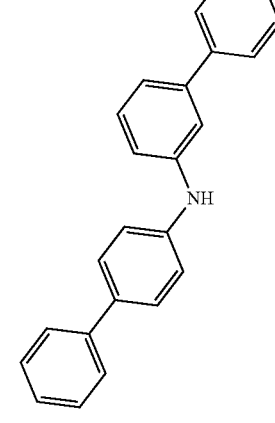 | 64% |
| A2-3 | Intermediate A(2) | 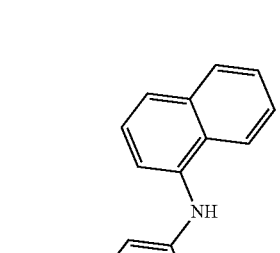 | 65% |

TABLE 2-continued

| Compound No. | Intermediate I | Intermediate II | yield |
|---|---|---|---|
| A2-4 | Intermediate A(2) | *(9,9-dimethylfluoren-2-yl)-N-(biphenyl-4-yl)amine structure* | 70% |
| A2-5 | Intermediate A(2) | *N-(biphenyl-4-yl)-4-(dibenzofuran-4-yl)aniline structure* | 70% |
| A2-7 | Intermediate A(2) | *(9,9-diphenylfluoren-2-yl)-N-(biphenyl-4-yl)amine structure* | 60% |

TABLE 2-continued

| Compound No. | Intermediate I | Intermediate II | yield |
| --- | --- | --- | --- |
| A2-11 | Intermediate A(2) | (4-phenylphenyl)-dibenzofuran-4-yl-amine structure | 60% |
| A2-13 | Intermediate A(2) | N-(4-([1,1':4',1''-terphenyl]-4-yl)phenyl)amine structure | 50% |
| A2-22 | Intermediate A(2) | bis(9,9-dimethyl-9H-fluoren-2-yl)amine structure | 60% |

TABLE 2-continued

| Compound No. | Intermediate I | Intermediate II | yield |
|---|---|---|---|
| A2-25 | Intermediate A(2) | | 71% |
| A2-27 | Intermediate A(2) | | 65% |
| A2-31 | Intermediate A(2) | | 57% |

TABLE 2-continued
| Compound No. | Intermediate I | Intermediate II | yield |
|---|---|---|---|
| A2-32 | Intermediate A(2) | 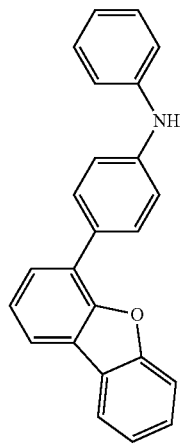 [SMILES: c1ccc(Nc2ccc(-c3cccc4c3oc3ccccc34)cc2)cc1] | 60% |
| A2-33 | Intermediate A(3) | 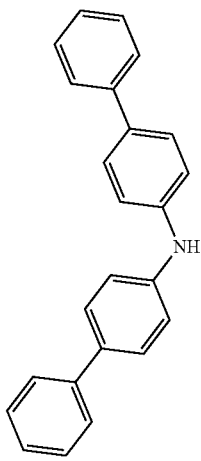 [SMILES: c1ccc(-c2ccc(Nc3ccc(-c4ccccc4)cc3)cc2)cc1] | 72% |
| A2-34 | Intermediate A(3) | 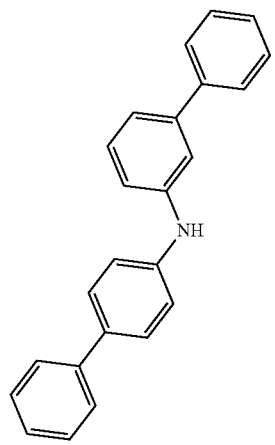 | 62% |

TABLE 2-continued

| Compound No. | Intermediate I | Intermediate II | yield |
| --- | --- | --- | --- |
| A2-35 | Intermediate A(3) | | 65% |
| A2-36 | Intermediate A(3) | | 60% |
| A2-38 | Intermediate A(3) | | 80% |

TABLE 2-continued

| Compound No. | Intermediate I | Intermediate II | yield |
|---|---|---|---|
| A2-39 | Intermediate A(3) | (N-([1,1'-biphenyl]-4-yl)dibenzofuran-4-amine structure) | 65% |
| A2-41 | Intermediate A(3) | (N-([1,1':4',1''-terphenyl]-4-yl)-[1,1'-biphenyl]-4-amine structure) | 53% |
| A2-44 | Intermediate A(3) | (N-([1,1'-biphenyl]-4-yl)naphthalen-1-amine structure) | 60% |

TABLE 2-continued

| Compound No. | Intermediate I | Intermediate II | yield |
|---|---|---|---|
| A2-46 | Intermediate A(3) | *(structure: N-phenyl-4'-phenyl-[1,1'-biphenyl]-4-amine)* | 60% |
| A2-49 | Intermediate A(4) | *(structure: bis(4-biphenyl)amine)* | 78% |
| A2-50 | Intermediate A(4) | *(structure: N-(4-biphenyl)naphthalen-1-amine)* | 67% |

TABLE 2-continued
| Compound No. | Intermediate I | Intermediate II | yield |
|---|---|---|---|
| A2-51 | Intermediate A(4) | 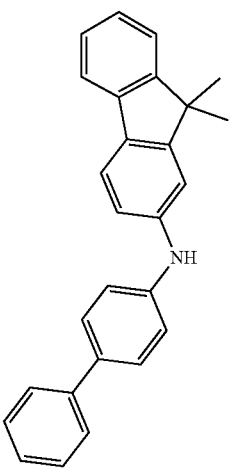 [SMILES: CC1(C)c2ccccc2-c2ccc(Nc3ccc(-c4ccccc4)cc3)cc21] | 65% |
| A2-52 | Intermediate A(4) | 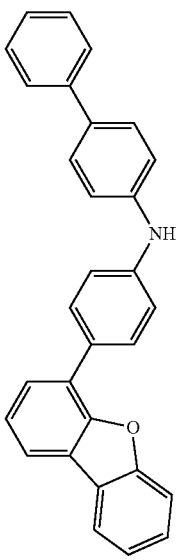 [SMILES: c1ccc(-c2ccc(Nc3ccc(-c4cccc5c4oc4ccccc45)cc3)cc2)cc1] | 77% |
| A2-54 | Intermediate A(4) | 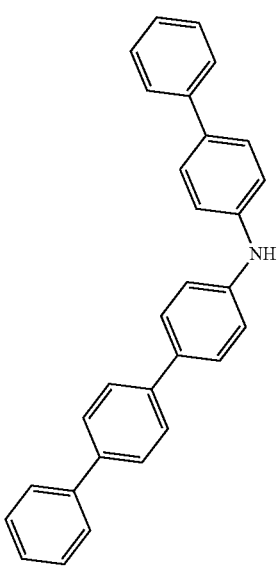 [SMILES: c1ccc(-c2ccc(Nc3ccc(-c4ccc(-c5ccccc5)cc4)cc3)cc2)cc1] | 44% |

TABLE 2-continued

| Compound No. | Intermediate I | Intermediate II | yield |
|---|---|---|---|
| A2-57 | Intermediate A(5) | *[structure: N-([1,1'-biphenyl]-4-yl)-[1,1'-biphenyl]-4-amine]* | 68% |
| A2-58 | Intermediate A(5) | *[structure: N-([1,1'-biphenyl]-4-yl)-9,9-dimethyl-9H-fluoren-2-amine]* | 71% |
| A2-59 | Intermediate A(5) | *[structure: N-([1,1'-biphenyl]-4-yl)naphthalen-1-amine]* | 65% |

TABLE 2-continued

| Compound No. | Intermediate I | Intermediate II | yield |
|---|---|---|---|
| A2-60 | Intermediate A(5) | | 80% |
| A2-62 | Intermediate A(5) | | 65% |
| A3-1 | Intermediate A(6) | | 70% |

TABLE 2-continued

| Compound No. | Intermediate I | Intermediate II | yield |
| --- | --- | --- | --- |
| A3-2 | Intermediate A(6) | (N-([1,1'-biphenyl]-4-yl)-[1,1'-biphenyl]-3-amine structure) | 65% |
| A3-3 | Intermediate A(6) | (N-([1,1'-biphenyl]-4-yl)-4-(dibenzofuran-4-yl)aniline structure) | 75% |
| A3-4 | Intermediate A(6) | (N-([1,1':4',1''-terphenyl]-4-yl)-[1,1'-biphenyl]-4-amine structure) | 54% |

TABLE 2-continued
| Compound No. | Intermediate I | Intermediate II | yield |
|---|---|---|---|
| A3-5 | Intermediate A(6) | 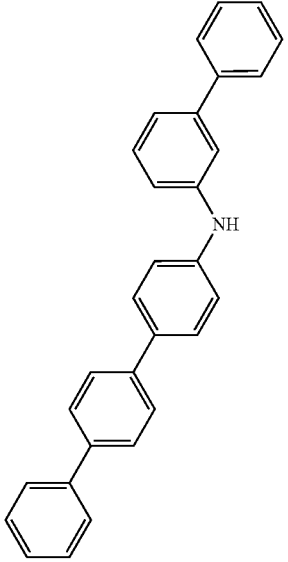 [SMILES: c1ccc(-c2ccc(-c3ccc(Nc4cccc(-c5ccccc5)c4)cc3)cc2)cc1] | 60% |
| A3-7 | Intermediate A(6) | 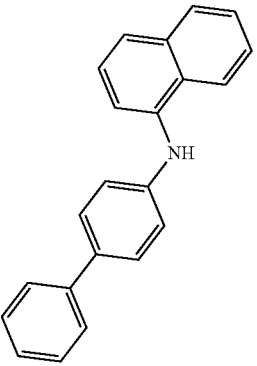 [SMILES: c1ccc(-c2ccc(Nc3cccc4ccccc34)cc2)cc1] | 59% |
| A3-8 | Intermediate A(6) | 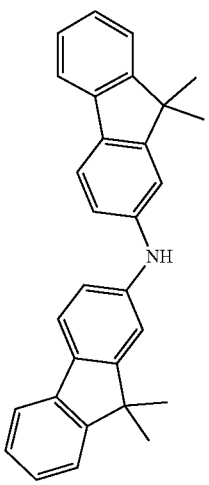 [SMILES: CC1(C)c2ccccc2-c2ccc(Nc3ccc4c(c3)C(C)(C)c3ccccc3-4)cc21] | 65% |

TABLE 2-continued
| Compound No. | Intermediate I | Intermediate II | yield |
|---|---|---|---|
| A3-9 | Intermediate A(6) | 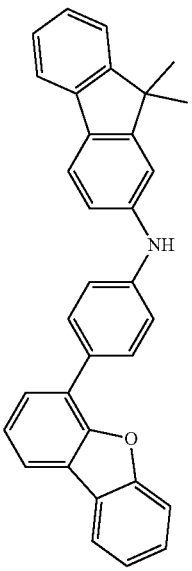 [SMILES: CC1(C)c2ccccc2-c2ccc(Nc3ccc(-c4cccc5c4oc4ccccc45)cc3)cc21] | 70% |
| A3-10 | Intermediate A(6) | 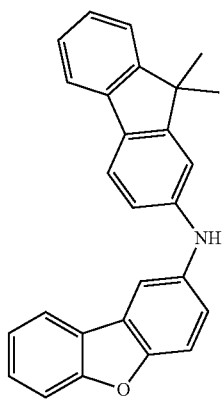 [SMILES: CC1(C)c2ccccc2-c2ccc(Nc3ccc4oc5ccccc5c4c3)cc21] | 62% |
| A3-15 | Intermediate A(6) | 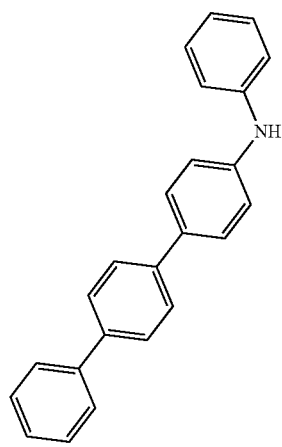 [SMILES: c1ccc(Nc2ccc(-c3ccc(-c4ccccc4)cc3)cc2)cc1] | 67% |

TABLE 2-continued
| Compound No. | Intermediate I | Intermediate II | yield |
|---|---|---|---|
| A3-16 | Intermediate A(6) | 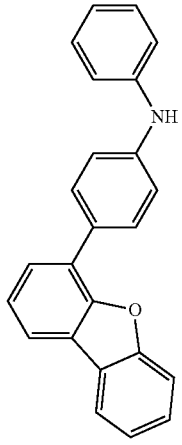 [SMILES: c1ccc(Nc2ccc(-c3cccc4c3oc3ccccc34)cc2)cc1] | 65% |
| A3-17 | Intermediate A(7) | 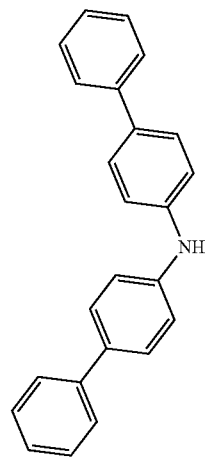 [SMILES: c1ccc(-c2ccc(Nc3ccc(-c4ccccc4)cc3)cc2)cc1] | 70% |
| A3-18 | Intermediate A(7) | 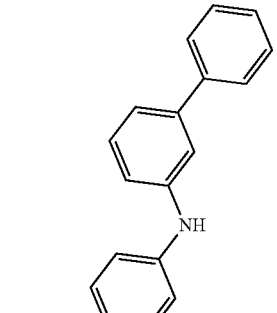 | 70% |

TABLE 2-continued

| Compound No. | Intermediate I | Intermediate II | yield |
|---|---|---|---|
| A3-19 | Intermediate A(7) | | 66% |
| A3-20 | Intermediate A(7) | | 70% |
| A3-21 | Intermediate A(7) | | 68% |

TABLE 2-continued
| Compound No. | Intermediate I | Intermediate II | yield |
|---|---|---|---|
| A3-23 | Intermediate A(7) | 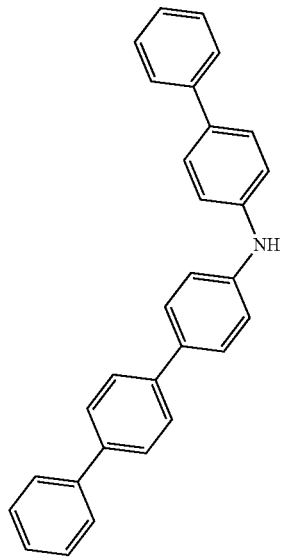 [SMILES: c1ccc(-c2ccc(Nc3ccc(-c4ccc(-c5ccccc5)cc4)cc3)cc2)cc1] | 60% |
| A3-27 | Intermediate A(7) | 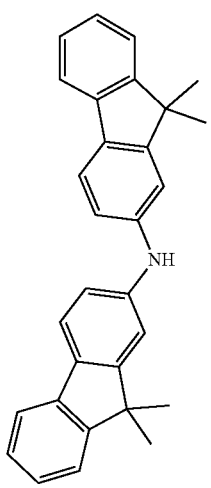 [SMILES: CC1(C)c2ccccc2-c2ccc(Nc3ccc4c(c3)C(C)(C)c3ccccc3-4)cc21] | 66% |
| A3-28 | Intermediate A(7) | 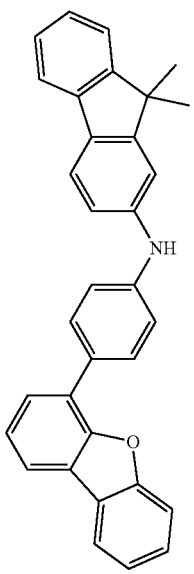 [SMILES: CC1(C)c2ccccc2-c2ccc(Nc3ccc(-c4cccc5c4oc4ccccc45)cc3)cc21] | 69% |

TABLE 2-continued

| Compound No. | Intermediate I | Intermediate II | yield |
|---|---|---|---|
| A4-1 | Intermediate A(8) | 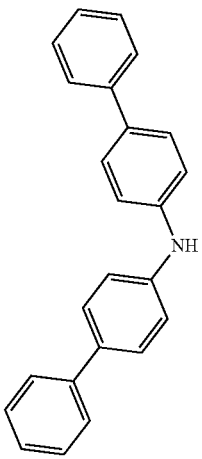 [SMILES: c1ccc(-c2ccc(Nc3ccc(-c4ccccc4)cc3)cc2)cc1] | 70% |
| A4-13 | Intermediate A(9) | 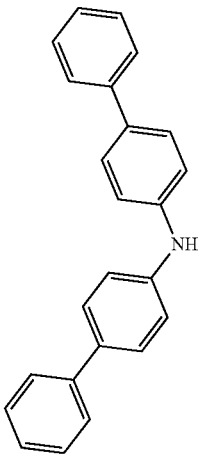 [SMILES: c1ccc(-c2ccc(Nc3ccc(-c4ccccc4)cc3)cc2)cc1] | 75% |
| A4-15 | Intermediate A(10) | 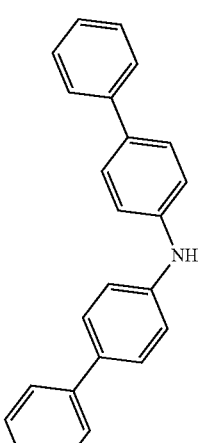 | 72% |

Compounds described in the present specification were prepared in the same manner as in the preparation examples, and in order to identify the synthesis results of the prepared compounds, FD-field desorption mass spectrometry (FD-MS) and 1H NMR (CDCl$_3$, 200 Mz) were measured, and the measured values are shown in the following Table 3 and Table 4. The following Table 3 shows measurement values of field desorption mass spectrometry (FD-MS) of the prepared compounds, and the following Table 4 shows measurement values of 1H NMR (CDCl$_3$, 200 Mz) of some of the prepared compounds.

TABLE 3

| Compound | FD-Mass | Compound | FD-Mass |
| --- | --- | --- | --- |
| A1-1 | m/z = 714.89(C54H38N2 = 714.30) | A1-2 | m/z = 714.89(C54H38N2 = 714.30) |
| A1-3 | m/z = 714.89(C54H38N2 = 714.30) | A1-4 | m/z = 714.89(C54H38N2 = 714.30) |
| A1-5 | m/z = 714.89(C54H38N2 = 714.30) | A1-6 | m/z = 754.96(C57H42N2 = 754.33) |
| A1-7 | m/z = 879.10(C67H46N2 = 878.37) | A1-8 | m/z = 877.08(C67H44N2 = 876.35) |
| A1-9 | m/z = 804.97(C60H40N2O = 804.31) | A1-10 | m/z = 804.97(C60H40N2O = 804.31) |
| A1-11 | m/z = 804.97(C60H40N2O = 804.31) | A1-12 | m/z = 821.04(C60H40N2S = 820.29) |
| A1-13 | m/z = 821.04(C60H40N2S = 820.29) | A1-14 | m/z = 821.04(C60H40N2S = 820.29) |
| A1-15 | m/z = 728.88(C54H36N2O = 728.28) | A1-16 | m/z = 728.88(C54H36N2O = 728.28) |
| A1-17 | m/z = 728.88(C54H36N2O = 728.28) | A1-18 | m/z = 790.99(C60H42N2 = 790.33) |
| A1-19 | m/z = 790.99(C60H42N2 = 790.33) | A1-20 | m/z = 831.05(C63H46N2 = 830.37) |
| A1-21 | m/z = 955.10(C73H50N2 = 954.40) | A1-22 | m/z = 953.18(C73H48N2 = 952.38) |
| A1-23 | m/z = 881.07(C66H44N2O = 880.35) | A1-24 | m/z = 881.07(C66H44N2O = 880.35) |
| A1-25 | m/z = 897.13(C66H44N2S = 896.32) | A1-26 | m/z = 897.13(C66H44N2S = 896.32) |
| A1-27 | m/z = 804.97(C60H40N2O = 804.31) | A1-28 | m/z = 804.97(C60H40N2O = 804.31) |
| A1-29 | m/z = 845.04(C63H44N2O = 844.35) | A1-30 | m/z = 845.04(C63H44N2O = 844.35) |
| A1-31 | m/z = 861.10(C63H44N2S = 860.32) | A1-32 | m/z = 861.10(C63H44N2S = 860.32) |
| A1-33 | m/z = 795.02(C60H46N2 = 794.37) | A1-34 | m/z = 871.12.99(C66H50N2 = 870.40) |
| A1-35 | m/z = 871.12.99(C66H50N2 = 870.40) | A1-36 | m/z = 768.94(C57H40N2O = 768.31) |
| A1-37 | m/z = 638.80(C48H34N2 = 638.27) | A1-38 | m/z = 678.86(C51H38N2 = 678.30) |
| A1-39 | m/z = 803.00(C61H42N2 = 802.33) | A1-40 | m/z = 800.98(C61H40N2 = 800.32) |
| A1-41 | m/z = 714.89(C54H38N2 = 714.30) | A1-42 | m/z = 728.88(C54H36N2O = 728.28) |
| A1-43 | m/z = 728.88(C54H36N2O = 728.28) | A1-44 | m/z = 652.78(C48H32N2O = 652.25) |
| A1-45 | m/z = 688.86(C52H36N2 = 688.29) | A1-46 | m/z = 688.86(C52H36N2 = 688.29) |
| A1-47 | m/z = 778.94(C58H38N2O = 778.30) | A1-48 | m/z = 764.95(C58H40N2 = 764.32) |
| A2-1 | m/z = 790.99(C60H42N2 = 790.33) | A2-2 | m/z = 790.99(C60H42N2 = 790.33) |
| A2-3 | m/z = 764.95(C58H40N2 = 764.32) | A2-4 | m/z = 831.05(C63H46N2 = 830.37) |
| A2-5 | m/z = 881.07(C66H44N2O = 880.35) | A2-6 | m/z = 855.03(C64H42N2 = 854.33) |
| A2-7 | m/z = 955.10(C73H50N2 = 954.40) | A2-8 | m/z = 953.18(C73H48N2 = 952.38) |
| A2-9 | m/z = 897.13(C66H44N2S = 896.32) | A2-10 | m/z = 897.13(C66H44N2S = 896.32) |
| A2-11 | m/z = 804.97(C60H40N2O = 804.31) | A2-12 | m/z = 804.97(C60H40N2O = 804.31) |
| A2-13 | m/z = 867.08(C66H46N2 = 866.37) | A2-14 | m/z = 867.08(C66H46N2 = 866.37) |
| A2-15 | m/z = 907.15(C69H50N2 = 906.40) | A2-16 | m/z = 1032.29(C79H54N2 = 1030.43) |
| A2-17 | m/z = 1029.27(C79H52N2 = 1028.41) | A2-18 | m/z = 957.16(C72H48N2O = 956.38) |
| A2-19 | m/z = 957.16(C72H48N2O = 956.38) | A2-20 | m/z = 973.23(C72H48N2S = 972.35) |
| A2-21 | m/z = 881.07(C66H44N2O = 880.35) | A2-22 | m/z = 871.12.99(C66H50N2 = 870.40) |
| A2-23 | m/z = 845.04(C63H44N2O = 844.35) | A2-24 | m/z = 881.07(C66H44N2O = 880.35) |
| A2-25 | m/z = 921.13(C69H48N2O = 920.38) | A2-26 | m/z = 921.13(C69H48N2O = 920.38) |
| A2-27 | m/z = 841.05(C64H44N2 = 840.35) | A2-28 | m/z = 754.96(C57H42N2 = 754.33) |
| A2-29 | m/z = 879.10(C67H46N2 = 878.37) | A2-30 | m/z = 877.08(C67H44N2 = 876.35) |
| A2-31 | m/z = 790.99(C60H42N2 = 790.33) | A2-32 | m/z = 804.97(C60H40N2O = 804.31) |
| A2-33 | m/z = 790.99(C60H42N2 = 790.33) | A2-34 | m/z = 790.99(C60H42N2 = 790.33) |
| A2-35 | m/z = 831.05(C63H46N2 = 830.37) | A2-36 | m/z = 955.10(C73H50N2 = 954.40) |
| A2-37 | m/z = 953.18(C73H48N2 = 952.38) | A2-38 | m/z = 881.07(C66H44N2O = 880.35) |
| A2-39 | m/z = 804.97(C60H40N2O = 804.31) | A2-40 | m/z = 907.15(C69H50N2 = 906.40) |
| A2-41 | m/z = 867.08(C66H46N2 = 866.37) | A2-42 | m/z = 841.05(C64H44N2 = 840.35) |
| A2-43 | m/z = 957.16(C72H48N2O = 956.38) | A2-44 | m/z = 764.95(C58H40N2 = 764.32) |
| A2-45 | m/z = 879.10(C67H46N2 = 878.37) | A2-46 | m/z = 790.99(C60H42N2 = 790.33) |
| A2-47 | m/z = 804.97(C60H40N2O = 804.31) | A2-48 | m/z = 728.88(C54H36N2O = 728.28) |
| A2-49 | m/z = 790.99(C60H42N2 = 790.33) | A2-50 | m/z = 764.95(C58H40N2 = 764.32) |
| A2-51 | m/z = 831.05(C63H46N2 = 830.37) | A2-52 | m/z = 881.07(C66H44N2O = 880.35) |
| A2-53 | m/z = 790.99(C60H42N2 = 790.33) | A2-54 | m/z = 867.08(C66H46N2 = 866.37) |
| A2-55 | m/z = 841.05(C64H44N2 = 840.35) | A2-56 | m/z = 804.97(C60H40N2O = 804.31) |
| A2-57 | m/z = 790.99(C60H42N2 = 790.33) | A2-58 | m/z = 831.05(C63H46N2 = 830.37) |
| A2-59 | m/z = 764.95(C58H40N2 = 764.32) | A2-60 | m/z = 881.07(C66H44N2O = 880.35) |
| A2-61 | m/z = 790.99(C60H42N2 = 790.33) | A2-62 | m/z = 804.97(C60H40N2O = 804.31) |
| A3-1 | m/z = 867.08(C66H46N2 = 866.37) | A3-2 | m/z = 867.08(C66H46N2 = 866.37) |
| A3-3 | m/z = 957.16(C72H48N2O = 956.38) | A3-4 | m/z = 881.07(C66H44N2O = 880.35) |
| A3-5 | m/z = 943.18(C75H50N2 = 942.40) | A3-6 | m/z = 943.18(C75H50N2 = 942.40) |
| A3-7 | m/z = 841.05(C64H44N2 = 840.35) | A3-8 | m/z = 947.21(C72H54N2 = 946.43) |
| A3-9 | m/z = 997.23(C75H52N2O = 996.41) | A3-10 | m/z = 921.13(C69H48N2O = 920.38) |
| A3-11 | m/z = 790.99(C60H42N2 = 790.33) | A3-12 | m/z = 831.05(C63H46N2 = 830.37) |
| A3-13 | m/z = 955.10(C73H50N2 = 954.40) | A3-14 | m/z = 953.18(C73H48N2 = 952.38) |
| A3-15 | m/z = 867.08(C66H46N2 = 866.37) | A3-16 | m/z = 881.07(C66H44N2O = 880.35) |
| A3-17 | m/z = 867.08(C66H46N2 = 866.37) | A3-18 | m/z = 867.08(C66H46N2 = 866.37) |
| A3-19 | m/z = 907.15(C69H50N2 = 906.40) | A3-20 | m/z = 957.16(C72H48N2O = 956.38) |
| A3-21 | m/z = 881.07(C66H44N2O = 880.35) | A3-22 | m/z = 983.24(C75H54N2 = 982.43) |
| A3-23 | m/z = 943.18(C75H50N2 = 942.40) | A3-24 | m/z = 790.99(C60H42N2 = 790.33) |
| A3-25 | m/z = 955.10(C73H50N2 = 954.40) | A3-26 | m/z = 917.14(C70H48N2 = 916.38) |
| A3-27 | m/z = 947.21(C72H54N2 = 946.43) | A3-28 | m/z = 997.23(C75H52N2O = 996.41) |
| A3-29 | m/z = 867.08(C66H46N2 = 866.37) | A3-30 | m/z = 957.16(C72H48N2O = 956.38) |
| A3-31 | m/z = 841.05(C64H44N2 = 840.35) | A3-32 | m/z = 947.21(C72H54N2 = 946.43) |
| A3-33 | m/z = 867.08(C66H46N2 = 866.37) | A3-34 | m/z = 957.16(C72H48N2O = 956.38) |
| A3-35 | m/z = 841.05(C64H44N2 = 840.35) | A3-36 | m/z = 947.21(C72H54N2 = 946.43) |
| A3-37 | m/z = 867.08(C66H46N2 = 866.37) | A3-38 | m/z = 957.16(C72H48N2O = 956.38) |
| A3-39 | m/z = 841.05(C64H44N2 = 840.35) | A3-40 | m/z = 947.21(C72H54N2 = 946.43) |
| A4-1 | m/z = 841.05(C64H44N2 = 840.35) | A4-2 | m/z = 881.11(C67H48N2 = 880.38) |
| A4-3 | m/z = 931.13(C70H46N2O = 930.36) | A4-4 | m/z = 917.14(C70H48N2 = 916.38) |
| A4-5 | m/z = 917.14(C70H48N2 = 916.38) | A4-6 | m/z = 957.21(C73H52N2 = 956.41) |

TABLE 3-continued

| Compound | FD-Mass | Compound | FD-Mass |
|---|---|---|---|
| A4-7 | m/z = 1007.22(C76H50N2O = 1006.39) | A4-8 | m/z = 921.18(C70H52N2 = 920.41) |
| A4-9 | m/z = 971.19(C73H50N2O = 970.39) | A4-10 | m/z = 764.95(C58H40N2 = 764.32) |
| A4-11 | m/z = 929.15(C71H48N2 = 928.38) | A4-12 | m/z = 841.05(C64H44N2 = 840.35) |
| A4-13 | m/z = 881.07(C66H44N2O = 880.35) | A4-14 | m/z = 921.13(C69H48N2O = 920.38) |
| A4-15 | m/z = 897.13(C66H44N2S = 896.32) | A4-16 | m/z = 897.13(C66H44N2S = 896.32) |
| A4-17 | m/z = 957.16(C72H48N2O = 956.38) | A4-18 | m/z = 841.05(C64H44N2 = 840.35) |
| A4-19 | m/z = 957.21(C73H52N2 = 956.41) | A4-20 | m/z = 917.14(C70H48N2 = 916.38) |
| A4-21 | m/z = 957.21(C73H52N2 = 956.41) | A4-22 | m/z = 1007.22(C76H50N2O = 1006.39) |
| A4-23 | m/z = 957.16(C72H48N2O = 956.38) | A4-24 | m/z = 917.14(C70H48N2 = 916.38) |
| A4-25 | m/z = 957.21(C73H52N2 = 956.41) | A4-26 | m/z = 1007.22(C76H50N2O = 1006.39) |
| A4-27 | m/z = 957.16(C72H48N2O = 956.38) | A4-28 | m/z = 917.14(C70H48N2 = 916.38) |
| A4-29 | m/z = 957.21(C73H52N2 = 956.41) | A4-30 | m/z = 1007.22(C76H50N2O = 1006.39) |
| A4-31 | m/z = 957.16(C72H48N2O = 956.38) | | |

TABLE 4

| Compound | $^1$H NMR(CDCl$_3$, 200 Mz) |
|---|---|
| A1-1 | δ = 8.55 (1H, d), 8.12 (1H, d), 7.94 (1H, d), 7.79 (1H, q), 7.68 (1H, q), 7.54~7.25 (27H, m), 6.69 (6H, d) |
| A1-6 | δ = 8.55 (1H, d), 8.12 (1H, d), 7.94~7.87 (2H, q), 7.79 (1H, d), 7.68~7.25 (25H, m), 6.75 (1H, s), 6.69 (4H, d), 6.58 (1H, d), 1.72 (6H, s) |
| A1-9 | δ = 8.55 (1H, d), 8.12 (1H, d), 7.94~7.79 (5H, m), 7.68~7.63 (3H, m), 7.54~7.25 (24H, m), 6.69 (6H, d) |
| A1-15 | δ = 8.55 (1H, d), 8.12 (1H, d), 7.94~7.89 (2H, q), 7.79 (1H, d), 7.68~7.63 (3H, q), 7.54-7.25 (22H, m), 7.07 (1H, t), 6.69 (4H, d), 6.39(1H, d) |
| A1-18 | δ = 8.55 (1H, d), 8.12 (1H, d), 7.94 (1H, d), 7.79 (1H, d), 7.68~7.63 (2H, m), 7.54~7.25 (30H, m), 6.69 (6H, d) |
| A1-33 | δ = 8.55 (1H, d), 8.12(1H, d), 7.94 (1H, d), 7.87 (2H, d), 7.79 (1H, d), 7.68~7.50 (11H, m), 7.38~7.25 (11H, m), 6.75 (1H, s), 6.69 (3H, d), 6.58 (2H, d), 1.72 (12H, s) |
| A2-1 | δ = 8.49 (1H, d), 8.12~8.10 (2H, t), 7.79 (1H, d), 7.68~7.62 (3H, m), 7.54~7.41 (24H, m), 7.29~7.25 (5H, m), 6.69 (6H, d) |
| A2-3 | δ = 8.49 (1H, d), 8.12~8.02 (4H, m), 7.79 (1H, d), 7.68~7.41 (24H, m), 7.29~7.25 (5H, m), 6.98 (1H, d), 6.69 (4H, d) |
| A2-4 | δ = 8.49 (1H, d), 8.12~8.10 (2H, t), 7.87 (1H, d), 7.79 (1H, d), 7.63~7.38 (23H, m), 7.29~7.25 (6H, m), 6.75 (1H, s), 6.69 (4H, d), 6.58 (1H, d), 1.72 (6H, s) |
| A2-5 | δ = 8.49 (1H, d), 8.12~8.10 (2H, t), 7.89~7.79 (4H, m), 7.68~7.62 (4H, m), 7.54~7.25 (27H, m), 6.69 (6H, d) |
| A2-13 | δ = 8.49 (1H, d), 8.12~8.10 (2H, t), 7.79 (1H, d), 7.68~7.62 (3H, m), 7.54~7.41 (24H, m), 7.29~7.25 (9H, m), 6.69 (6H, d) |
| A2-33 | δ = 8.18~8.12 (2H, q), 8.00 (1H, d), 7.79~7.77 (2H, m), 7.68~7.63 (2H, m), 7.54~7.41 (24H, m), 7.29~7.25 (5H, m), 6.69 (6H, d) |
| A2-35 | δ = 8.18~8.12 (2H, q), 8.00 (1H, d), 7.87 (1H, d), 7.79~7.77(2H, m), 7.68~7.38 (22H, m), 7.29~7.25 (6H, m), 6.75 (1H, s), 6.69 (4H, d), 6.58 (1H, d), 1.72 (6H, s) |
| A2-38 | δ = 8.18~8.12 (2H, q), 8.00 (1H, d), 7.89~7.77 (5H, m), 7.68~7.63 (3H, m), 7.54~7.25 (27H, m), 6.69 (6H, d) |
| A3-1 | δ = 8.49 (1H, d), 8.18 (1H, d), 8.10 (1H, d), 7.79(2H, d), 7.68 (1H, d), 7.62 (2H, d), 7.54~7.41 (28H, m), 7.25 (4H, s), 6.69 (6H, d) |
| A3-3 | δ = 8.49 (1H, d), 8.18 (1H, d), 8.10 (1H, d), 7.89~7.79 (5H, m), 7.68~7.62 (4H, m), 7.54~7.32 (26H, m), 7.25 (4H, s), 6.69 (6H, d) |
| A3-7 | δ = 8.49 (1H, d), 8.18 (1H, d), 8.10~8.02 (3H, m), 7.79 (2H, d), 7.68 (1H, d), 7.62~7.38 (27H, m), 7.25 (4H, s), 6.98 (1H, d), 6.69 (4H, d) |
| A4-1 | δ = 8.55 (2H, m), 8.42 (1H, d), 8.18 (1H, d), 8.08~8.04 (2H, m), 7.94 (1H, d), 7.79 (2H, d), 7.68~7.25 (29H, m), 6.69 (6H, d) |
| A4-5 | δ = 8.55~8.49 (2H, m), 8.42 (1H, d), 8.18 (1H, d), 8.10~8.04 (3H, m), 7.79 (2H, d), 7.68~7.41 (29H, m), 7.25 (4H, s), 6.69 (6H, d) |
| A4-13 | δ = 8.55 (1H, d), 8.18 (1H, d), 7.94~7.79 (6H, m), 7.68~7.62 (3H, m), 7.54~7.25 (27H, m) 6.69 (6H, d) |

(Manufacture of Organic Light Emitting Diode)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer, a common layer, was formed using 4,4',4"-tris[2-naphthyl(phenyl)amino]triphenylamine (2-TNATA).

On the hole injection layer, a hole transfer layer was formed using each of compounds described in the following Table 5.

Materials included in the examples were used, and as a comparative material, six materials were formed.

Compounds used in Comparative Examples 1 to 6 described in the following Table 5 are as follows.

Comparative Example [1] Comparative Example [2] Comparative Example [3]
Comparative Example [4] Comparative Example [5] Comparative Example [6]
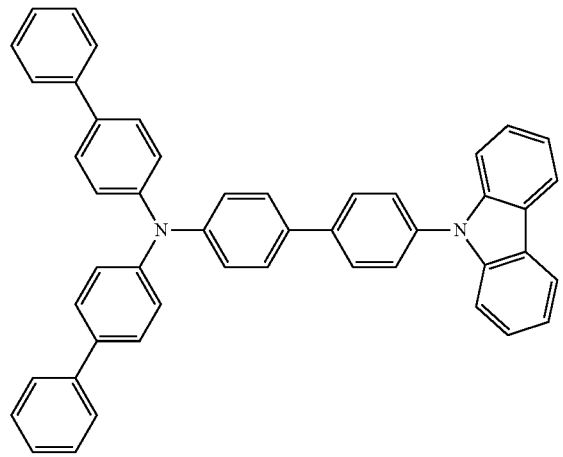
Molecular Weight: 638.80
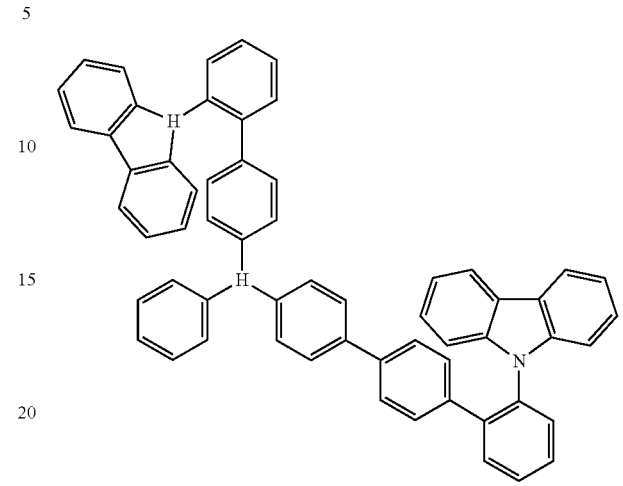
Molecular Weight: 803.99
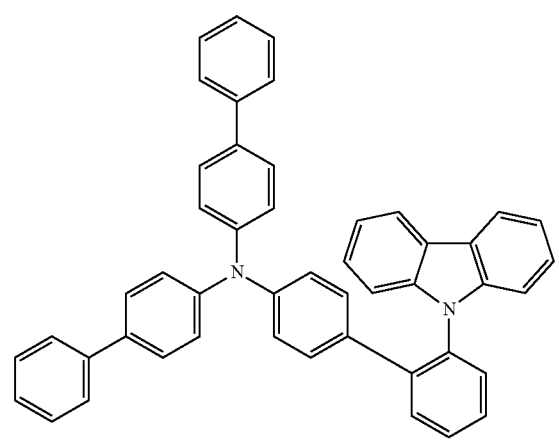
Molecular Weight: 638.80
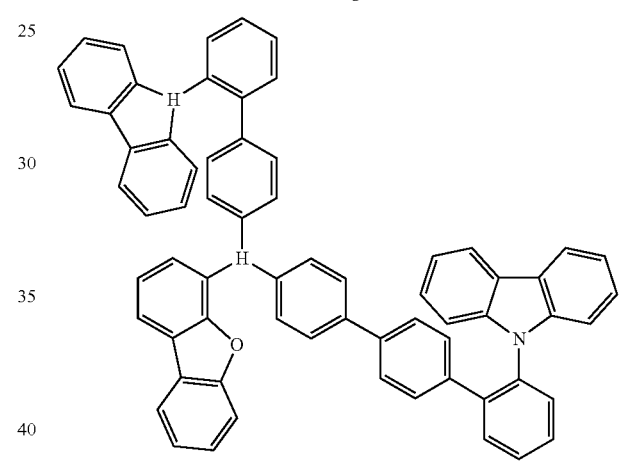
Molecular Weight: 894.07
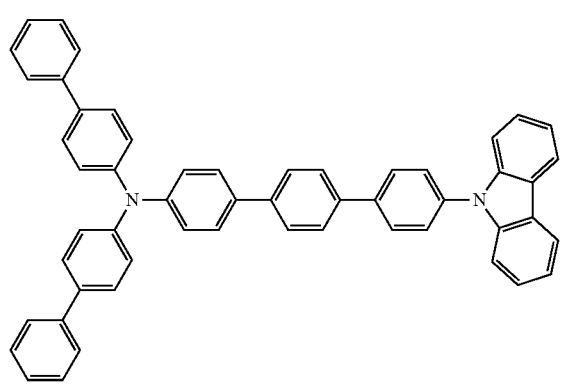
Molecular Weight: 714.89
Molecular Weight: 880.08

A light emitting layer was thermal vacuum deposited thereon as follows. As the light emitting layer, a compound of 9-[4-4,6-diphenyl-1,3,5-triazin-2-yl)phenyl]-9'-phenyl-3,3'-bi-9H-carbazole was deposited to 400 Å as a host, and Ir(ppy)$_3$, a green phosphorescent dopant, was 7% doped and deposited. After that, BCP was deposited to 60 Å as a hole blocking layer, and Alq$_3$ was deposited thereon to 200 Å as an electron transfer layer. Lastly, lithium fluoride (LiF) was deposited on the electron transfer layer to a thickness of 10 Å to form an electron injection layer, and then an aluminum (Al) cathode was deposited on the electron injection layer to a thickness of 1,200 Å to form a cathode, and as a result, an organic electroluminescent diode was manufactured.

Meanwhile, all the organic compounds required to manufacture the OLED were vacuum sublimation purified under $10^{-6}$ torr to $10^{-8}$ torr for each material to be used in the OLED manufacture.

Evaluation: Identification of Effects of Improvement in Driving Voltage, and Increases in Light Emission Efficiency and Lifetime For the organic light emitting diodes according to the examples and the comparative examples, driving voltage and lifetime properties were evaluated. Specific measurement methods are as follows, and the results are as follows.

(1) Measurement of Change in Current Density Depending on Change in Voltage

For the manufactured organic light emitting diodes, a value of a current flowing to the unit device was measured using a current-voltmeter (Keithley 2400) while increasing a voltage from 0 V to 10 V, and the measured current value was divided by the area to obtain results.

(2) Measurement of Change in Luminance Depending on Change in Voltage

For the manufactured organic light emitting diodes, a voltage was increased from 0 V to 10 V, and luminance at the time was measured using a luminance meter (Minolta Cs-1000A) to obtain results.

(3) Measurement of Light Emission Efficiency

Using the luminance, the current density and the voltage measured from (1) and (2), current efficiency (cd/A) of the same current density (10 mA/cm$^2$) was calculated.

(4) Measurement of Lifetime

Using a Polaronics Lifetime Measurement System for the manufactured organic light emitting diodes, each of the devices of the examples and the comparative examples of the following Table 5 was emitted with initial luminance (cd/m$^2$) of 24000 cd/m$^2$. A decrease in the luminance over time was measured, and the time when the luminance decreased to 90% with respect to initial luminance was measured as a T90 lifetime.

(5) Measurement of Driving Voltage

A driving voltage of each of the devices was measured at mA/cm$^2$ using a current-voltmeter (Keithley 2400) to obtain results.

TABLE 5

| | Hole Transfer Compound | Driving Voltage (V) | Efficiency (cd/A) | Lifetime (T$_{90}$) |
|---|---|---|---|---|
| Comparative Example 1 | I | 4.18 | 116.76 | 164 |
| Comparative Example 2 | II | 4.15 | 118.80 | 166 |
| Comparative Example 3 | III | 4.19 | 120.12 | 170 |
| Comparative Example 4 | IV | 4.37 | 106.71 | 162 |
| Comparative Example 5 | V | 4.25 | 120.76 | 147 |
| Comparative Example 6 | VI | 4.41 | 112.13 | 134 |
| Example A1 | A1-1 | 3.87 | 138.65 | 230 |
| Example A2 | A1-2 | 3.80 | 130.31 | 234 |
| Example A3 | A1-6 | 3.83 | 132.22 | 240 |
| Example A4 | A1-7 | 3.88 | 140.00 | 268 |
| Example A5 | A1-9 | 3.92 | 138.82 | 260 |
| Example A6 | A1-10 | 3.92 | 144.01 | 260 |
| Example A7 | A1-11 | 3.90 | 143.87 | 260 |
| Example A8 | A1-15 | 3.84 | 139.91 | 254 |
| Example A9 | A1-29 | 3.88 | 139.95 | 272 |
| Example A10 | A1-33 | 3.84 | 134.45 | 270 |
| Example A11 | A1-34 | 3.84 | 136.46 | 272 |
| Example A12 | A1-41 | 3.87 | 138.88 | 230 |
| Example A13 | A1-42 | 3.84 | 138.35 | 254 |
| Example A14 | A1-45 | 3.80 | 140.44 | 240 |
| Example A15 | A2-1 | 3.78 | 148.81 | 320 |
| Example A16 | A2-2 | 3.74 | 148.45 | 322 |
| Example A17 | A2-3 | 3.76 | 149.75 | 324 |
| Example A18 | A2-4 | 3.75 | 149.11 | 325 |
| Example A19 | A2-5 | 3.79 | 150.85 | 320 |
| Example A20 | A2-7 | 3.77 | 149.15 | 327 |
| Example A21 | A2-11 | 3.79 | 148.97 | 317 |
| Example A22 | A2-13 | 3.76 | 147.89 | 324 |
| Example A23 | A2-22 | 3.78 | 149.99 | 321 |
| Example A24 | A2-25 | 3.80 | 152.25 | 326 |
| Example A25 | A2-27 | 3.81 | 150.67 | 322 |
| Example A26 | A2-31 | 3.79 | 150.69 | 318 |
| Example A27 | A2-32 | 3.77 | 149.71 | 317 |
| Example A28 | A2-33 | 3.75 | 150.89 | 320 |
| Example A29 | A2-34 | 3.78 | 151.31 | 322 |
| Example A30 | A2-35 | 3.80 | 149.99 | 324 |
| Example A31 | A2-38 | 3.79 | 147.95 | 325 |
| Example A32 | A2-39 | 3.77 | 148.99 | 321 |
| Example A33 | A2-41 | 3.78 | 150.25 | 324 |
| Example A34 | A2-44 | 3.82 | 151.74 | 322 |
| Example A35 | A2-46 | 3.80 | 149.86 | 329 |
| Example A36 | A2-49 | 3.76 | 148.88 | 330 |
| Example A37 | A2-50 | 3.77 | 150.11 | 332 |
| Example A38 | A2-51 | 3.79 | 151.67 | 327 |
| Example A39 | A2-52 | 3.75 | 150.11 | 325 |
| Example A40 | A2-54 | 3.77 | 149.13 | 327 |
| Example A41 | A2-57 | 3.73 | 150.71 | 323 |
| Example A42 | A2-58 | 3.77 | 149.61 | 326 |
| Example A43 | A2-59 | 3.79 | 148.65 | 329 |
| Example A44 | A2-60 | 3.74 | 150.36 | 327 |
| Example A45 | A2-62 | 3.75 | 151.77 | 322 |
| Example A46 | A3-1 | 3.81 | 150.44 | 324 |
| Example A47 | A3-2 | 3.82 | 151.12 | 322 |
| Example A48 | A3-3 | 3.80 | 154.41 | 327 |
| Example A49 | A3-4 | 3.83 | 149.99 | 318 |
| Example A50 | A3-5 | 3.81 | 150.07 | 330 |
| Example A51 | A3-7 | 3.82 | 150.00 | 328 |
| Example A52 | A3-8 | 3.81 | 151.32 | 324 |
| Example A53 | A3-9 | 3.84 | 152.72 | 325 |
| Example A54 | A3-15 | 3.85 | 151.99 | 324 |
| Example A55 | A3-16 | 3.85 | 153.12 | 322 |
| Example A56 | A3-17 | 3.83 | 151.25 | 325 |
| Example A57 | A3-18 | 3.80 | 150.03 | 320 |
| Example A58 | A3-19 | 3.81 | 149.79 | 322 |
| Example A59 | A3-20 | 3.84 | 149.71 | 328 |
| Example A60 | A3-21 | 3.83 | 152.11 | 322 |
| Example A61 | A3-23 | 3.80 | 148.01 | 325 |
| Example A62 | A3-27 | 3.85 | 150.36 | 324 |
| Example A63 | A3-28 | 3.85 | 150.11 | 323 |
| Example A64 | A4-1 | 3.82 | 148.89 | 307 |
| Example A65 | A4-13 | 3.82 | 147.90 | 330 |
| Example A66 | A4-15 | 3.85 | 149.05 | 324 |

When referring to Table 5, it was identified that the compound according to the present disclosure had lower driving voltage and enhanced lifetime and light emission efficiency compared to the compounds of the comparative examples. Particularly, when two or more carbazole groups substituted, TS and deposition temperature increased resulting in a decrease in the lifetime, and high driving voltage and low efficiency were obtained.

This means that the compound of the present application having a structure in which any one of substituents of the amine group is a terphenylene group, and a substituted or unsubstituted heteroaryl group bonds to an ortho position based on the phenyl group farthest from the position of the terphenylene group at which the amine group bonds has expanded HOMO electron cloud and increases a HOMO energy level therethrough, and as a result, hole injection and hole transfer abilities are further strengthened, and therefore, a driving voltage of a diode using the same may be lowered, and high efficiency and long lifetime may be expected.

Moreover, when compared to a compound including a substituted or unsubstituted heteroaryl group bonding to a para position based on the phenyl group farthest from the position of the terphenylene group at which the amine group bonds, intermolecular interactions are reduced by increasing a steric size, which enhances thin film stability by suppressing material crystallization.

Hereinbefore, preferred examples of the present disclosure have been described in detail, however, the scope of a right of the present disclosure is not limited thereto, and various modifications and improvements made by those skilled in the art using the basic concept of the present disclosure defined in the attached claims also fall within the scope of a right of the present disclosure.

The invention claimed is:

1. A compound represented by the following Chemical Formula 1:

[Chemical Formula 1]

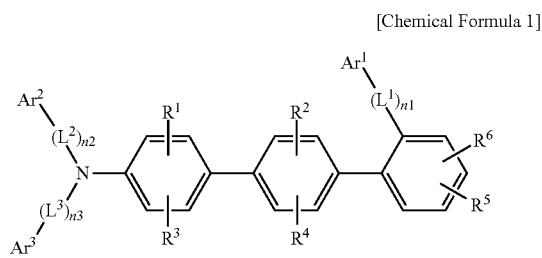

wherein, in Chemical Formula 1, $Ar^1$ is a substituted or unsubstituted C2 to C60 heteroaryl group;

$Ar^2$ and $Ar^3$ are each independently a substituted or unsubstituted C6 to C60 aryl group, or any one of the following Chemical Formulae 3-1 to 3-4;

$L^1$ to $L^3$ are each independently a single bond, a substituted or unsubstituted C6 to C60 arylene group, or a substituted or unsubstituted C2 to C60 heteroarylene group;

n1 to n3 are each independently one of integers of 0 to 2; and $R^1$ to $R^6$ are each independently hydrogen, deuterium, a cyano group, a substituted or unsubstituted C1 to C60 alkyl group, or a substituted or unsubstituted C6 to C60 aryl group,

[Chemical Formula 3-1]

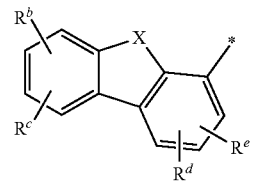

[Chemical Formula 3-2]

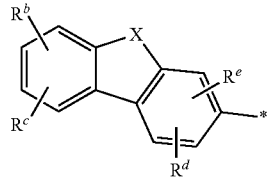

[Chemical Formula 3-3]

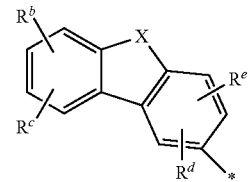

[Chemical Formula 3-4]

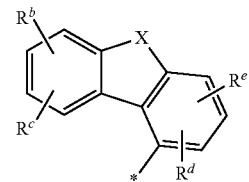

in Chemical Formula 3-1 to Chemical Formula 3-4,

X is —O—, —S— or —$CR^xR^y$—;

$R^x$ and $R^y$ are each independently hydrogen, deuterium, a cyano group, a substituted or unsubstituted C1 to C60 alkyl group or a C6 to C60 aryl group, or fused to each other to form a ring; and $R^b$ to $R^e$ are each independently hydrogen, deuterium, a cyano group, a substituted or unsubstituted C1 to C60 alkyl group, or a C6 to C60 aryl group.

2. The compound of claim 1, wherein $Ar^1$ is any one of the following Chemical Formulae 2-1 to 2-5:

[Chemical Formula 2-1]

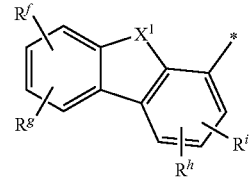

[Chemical Formula 2-2]

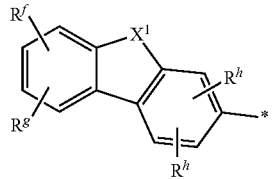

135
-continued

[Chemical Formula 2-3]

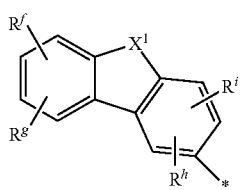

[Chemical Formula [2-4]]

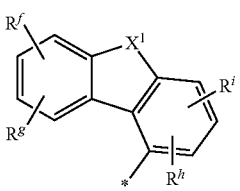

[Chemical Formula [2-5]]

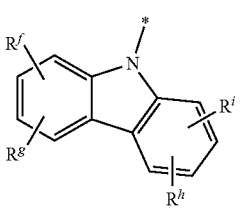

in Chemical Formula 2-1 to Chemical Formula 2-5,
$X^1$ is —$NR^x$—, —O— or —S—; and
$R^f$ to $R^i$ are each independently hydrogen, deuterium, a cyano group, a substituted or unsubstituted C1 to C60 alkyl group, a substituted or unsubstituted C6 to C60 aryl group, or a substituted or unsubstituted C2 to C60 heteroaryl group.

3. The compound of claim 1, wherein $Ar^1$ is a substituted or unsubstituted carbazolyl group.

4. The compound of claim 1, wherein $Ar^1$ is a substituted or unsubstituted dibenzofuranyl group.

5. The compound of claim 1, wherein $Ar^1$ is a substituted or unsubstituted dibenzothiophenyl group.

6. The compound of claim 1, wherein $Ar^2$ and $Ar^3$ are each independently any one of substituents of the following Group I:

[Group I]

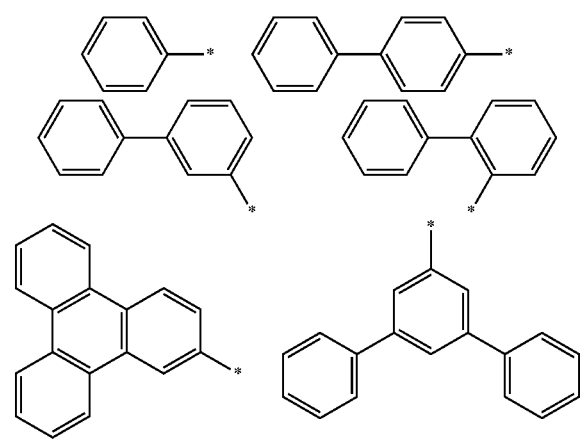

136
-continued

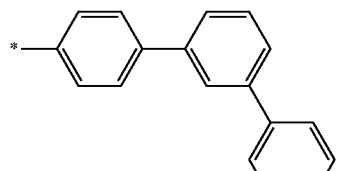

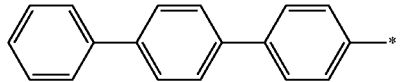

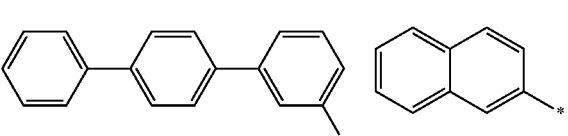

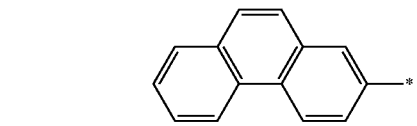

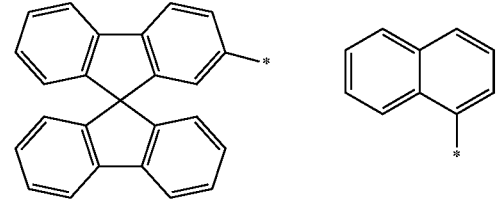

in Group I,
* means a bonding position.

7. The compound of claim 1, wherein the compound represented by Chemical Formula 1 is any one of compounds of the following Group II:

[Group II]

[Group II]

A1-1

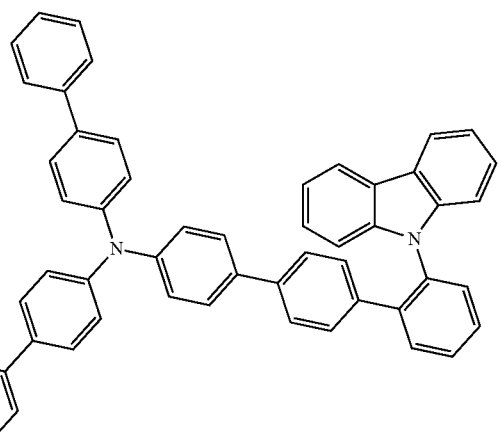

A1-2
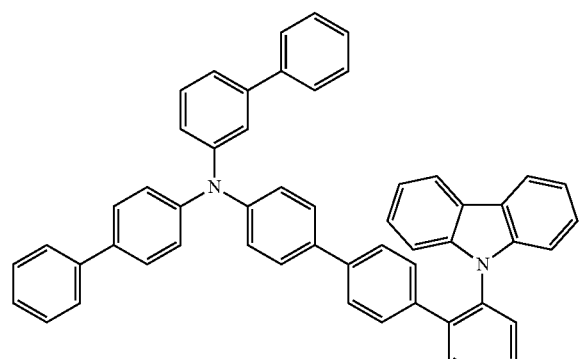
A1-3
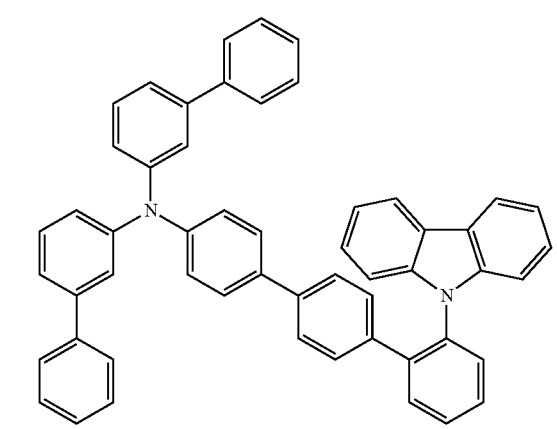
A1-4
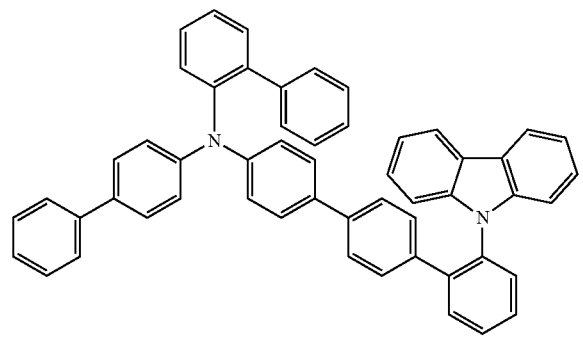
A1-5
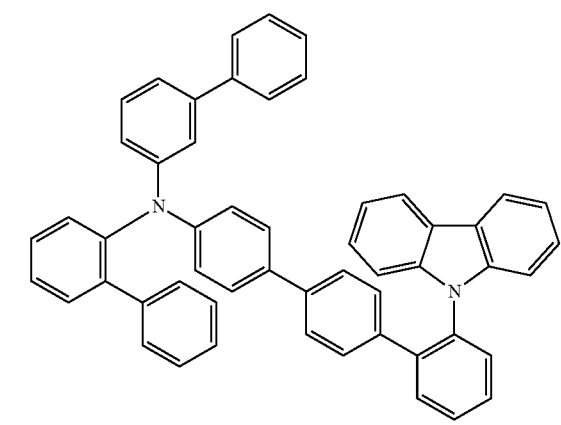
A1-6
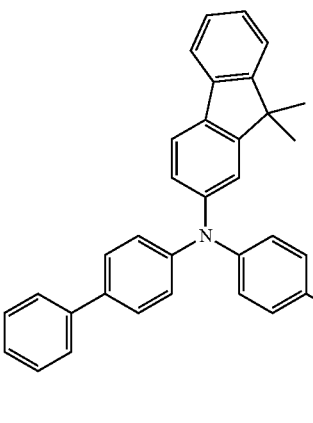
A1-7
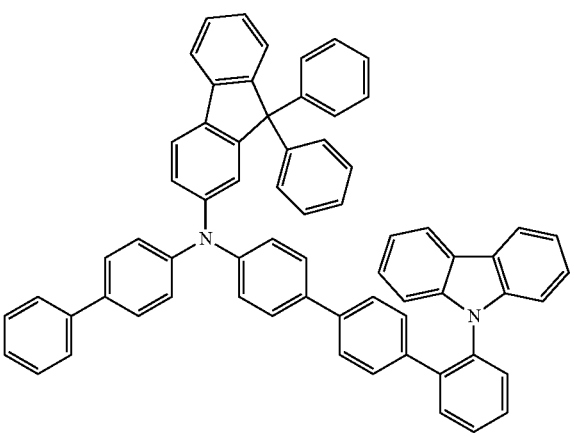
A1-8
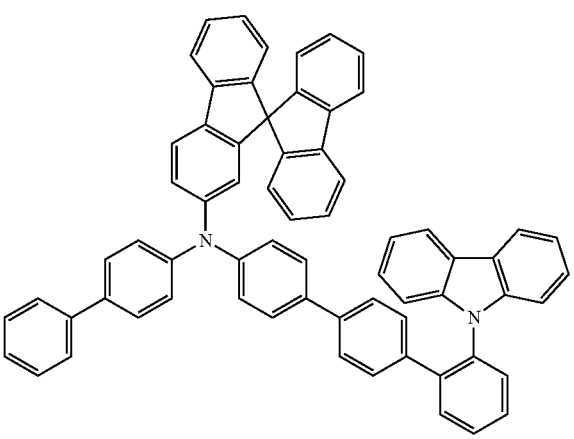

A1-9
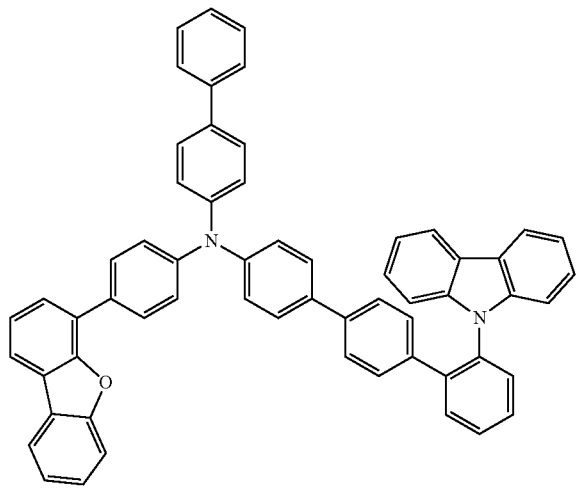
A1-10
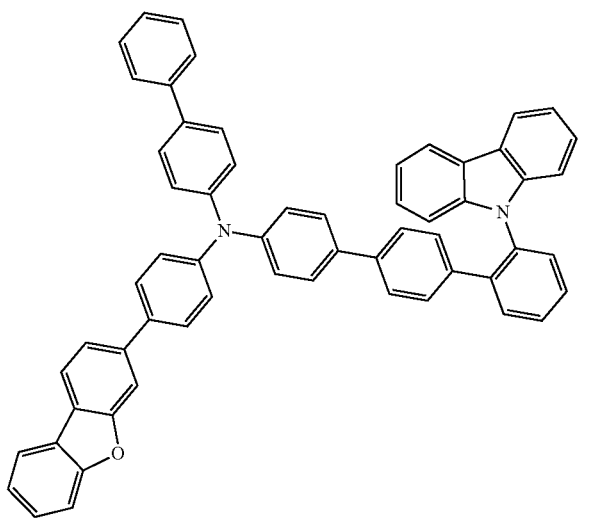
A1-11
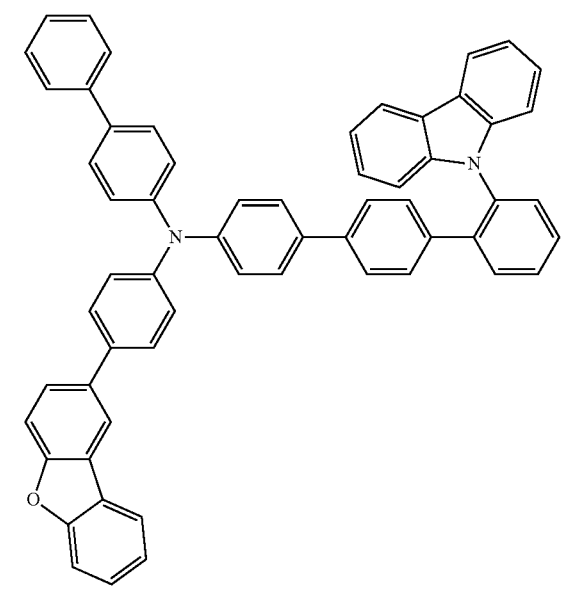
A1-12
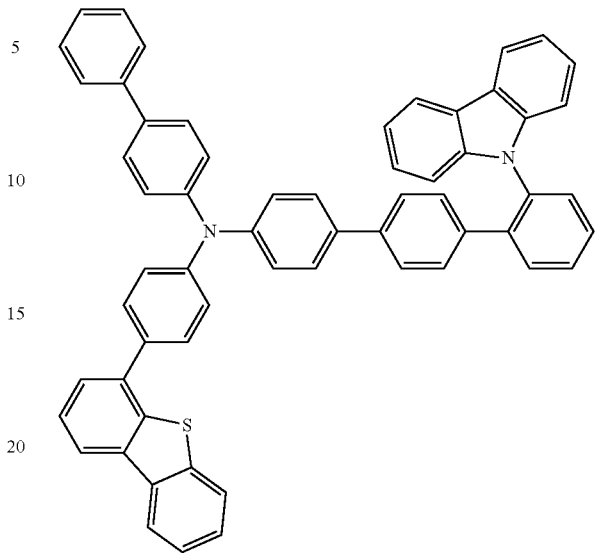
A1-13
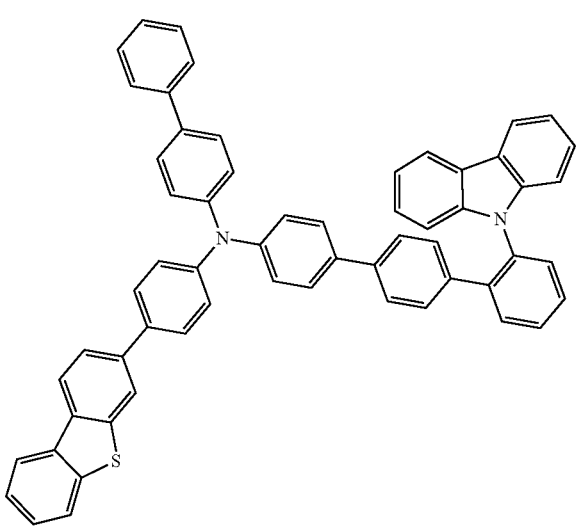

A1-14
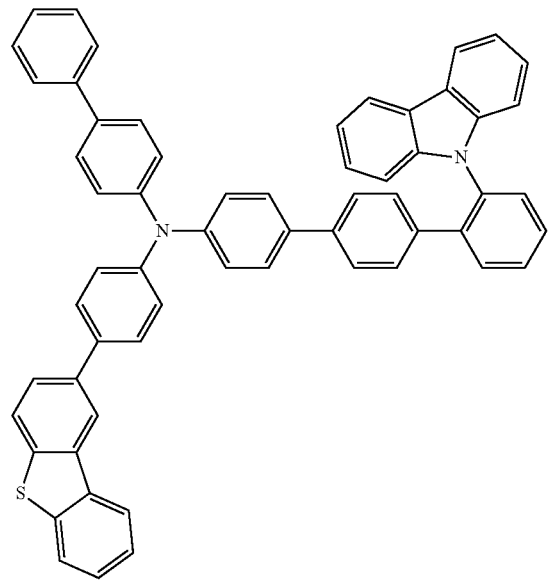
A1-15
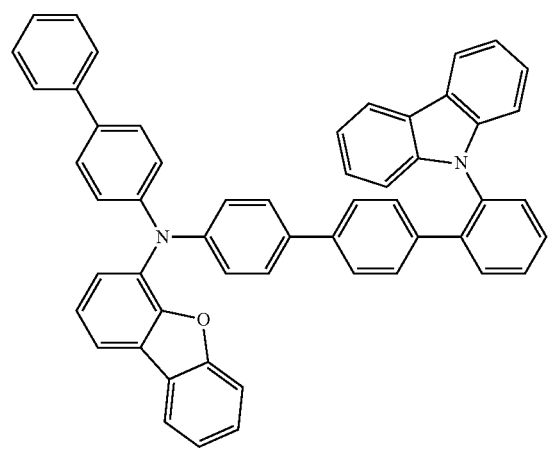
A1-16
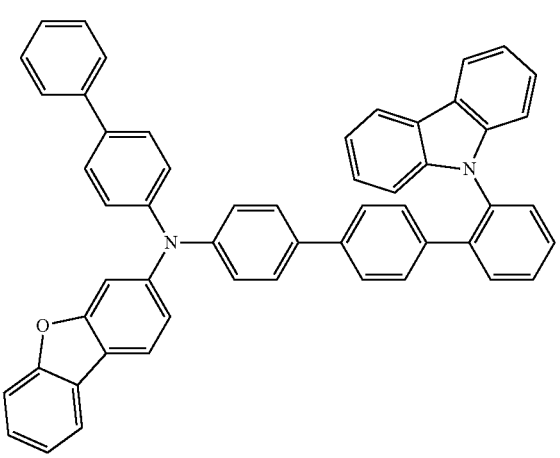
A1-17
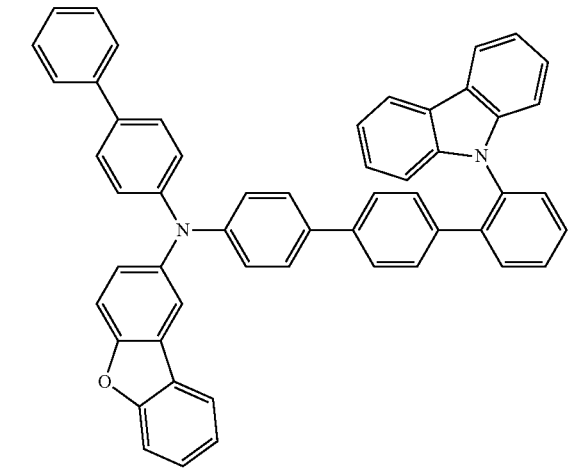
A1-18
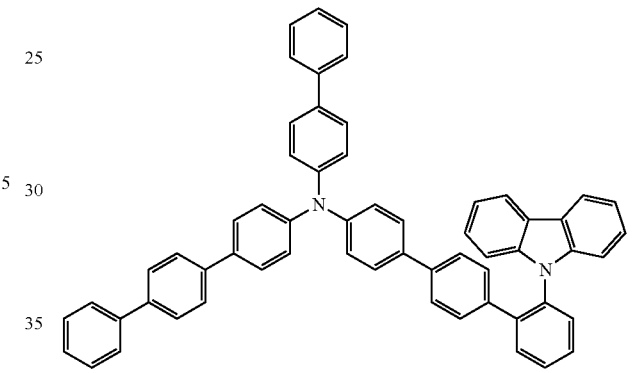
A1-19
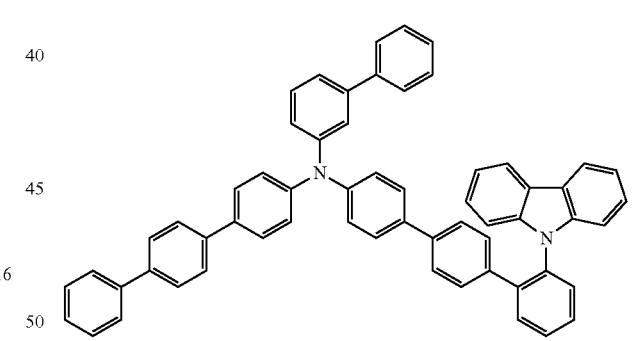
A1-20
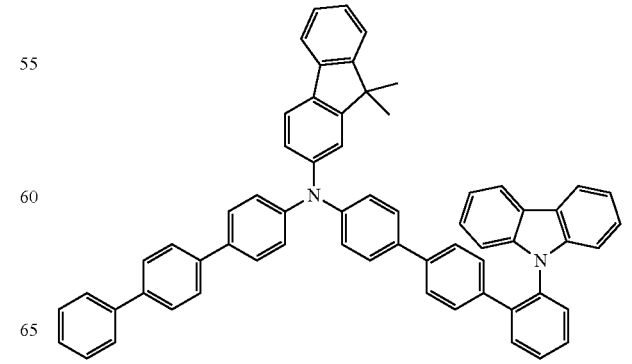

A1-21
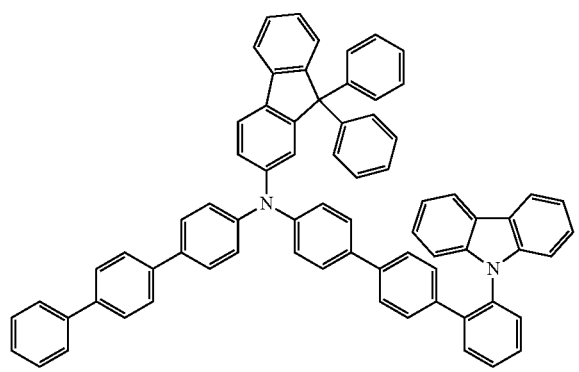
A1-22
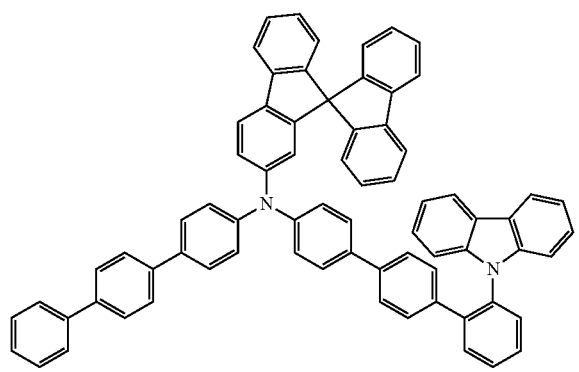
A1-23
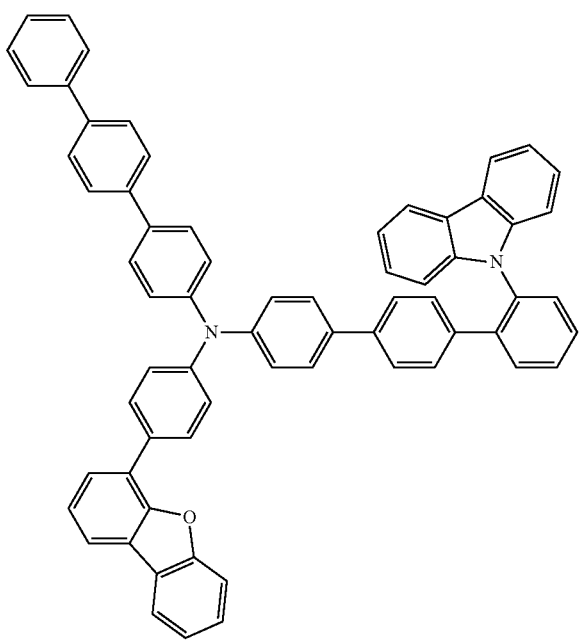
A1-24
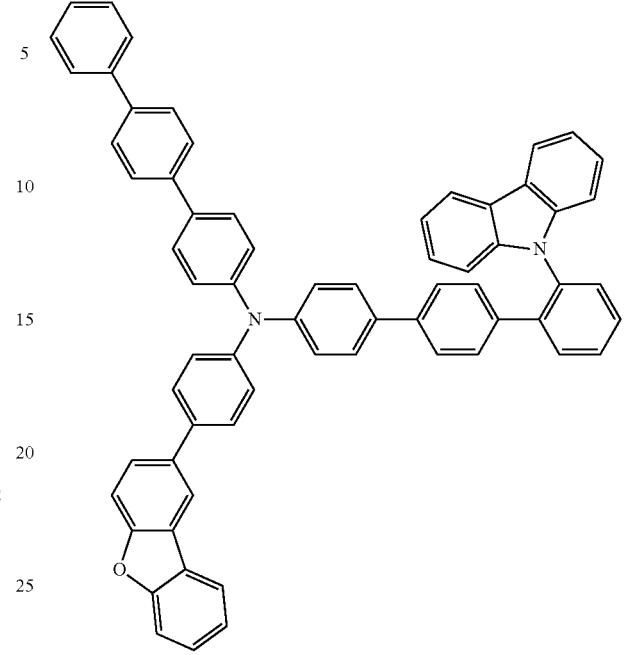
A1-25
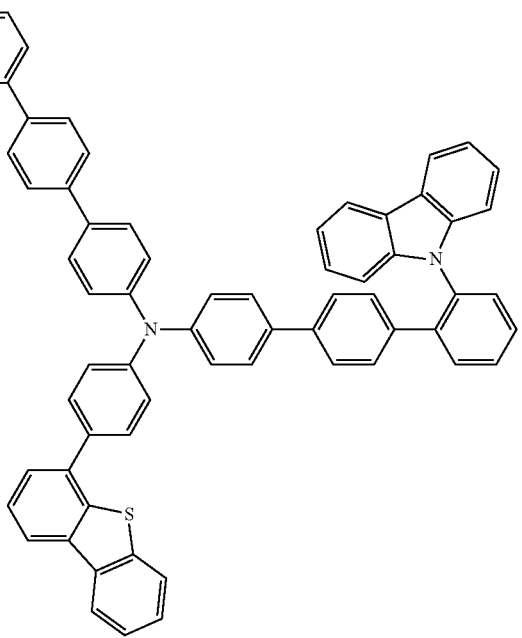

A1-26
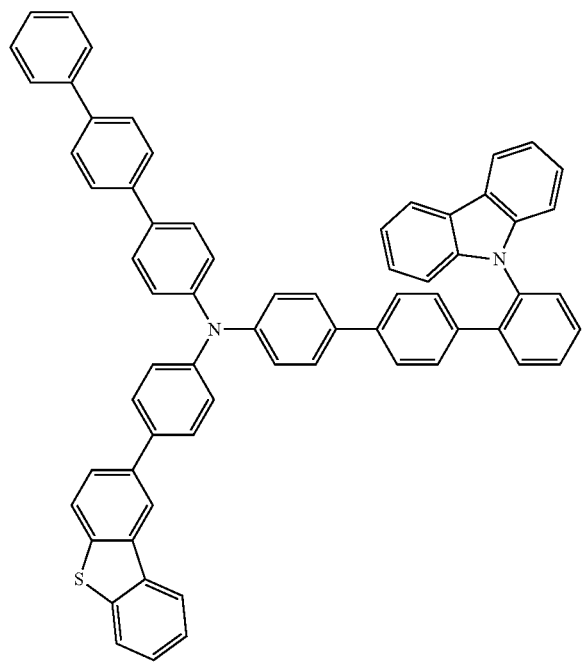
A1-28
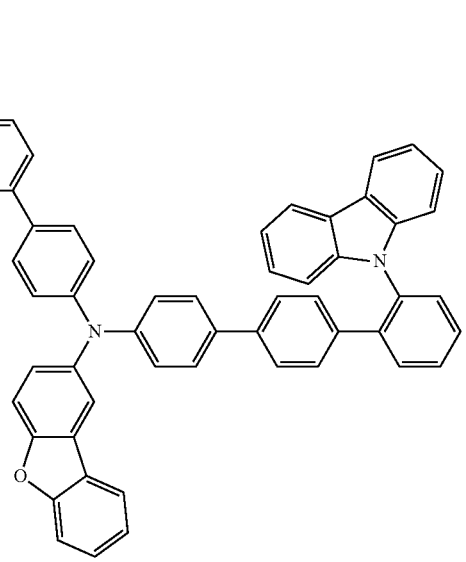
A1-27
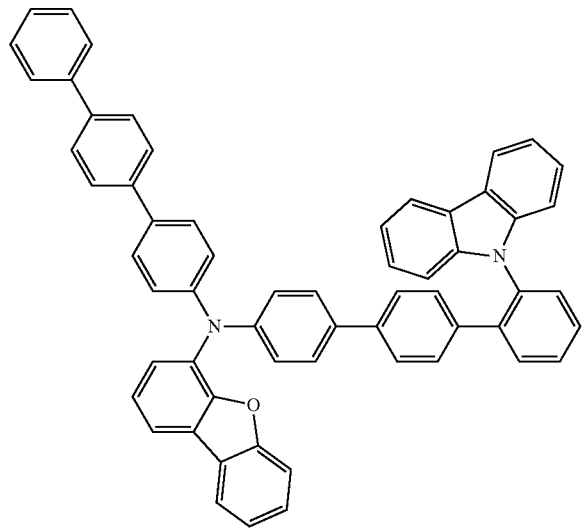
A1-29
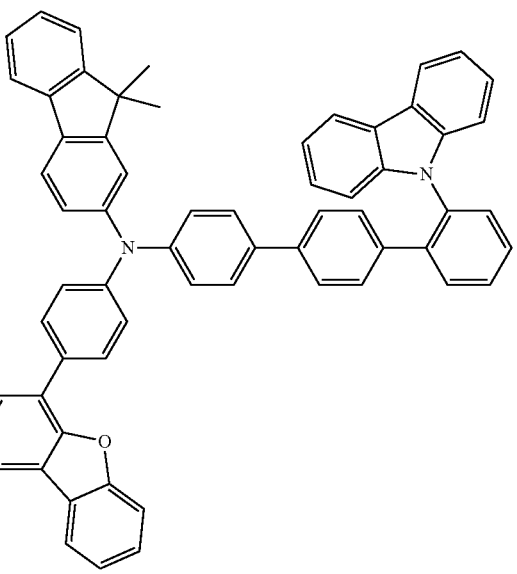

A1-30
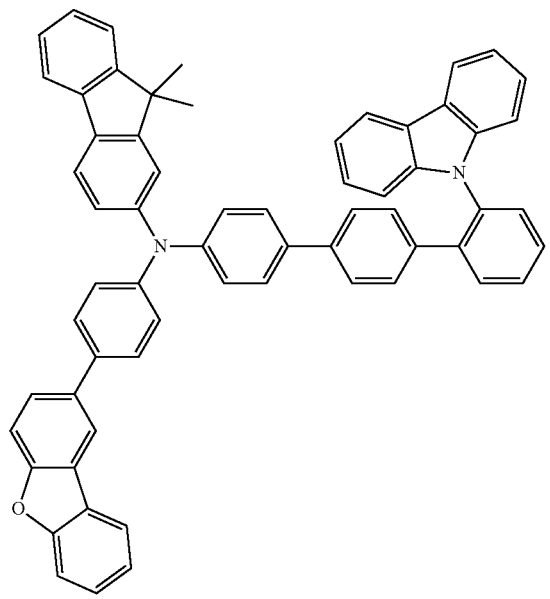
A1-32
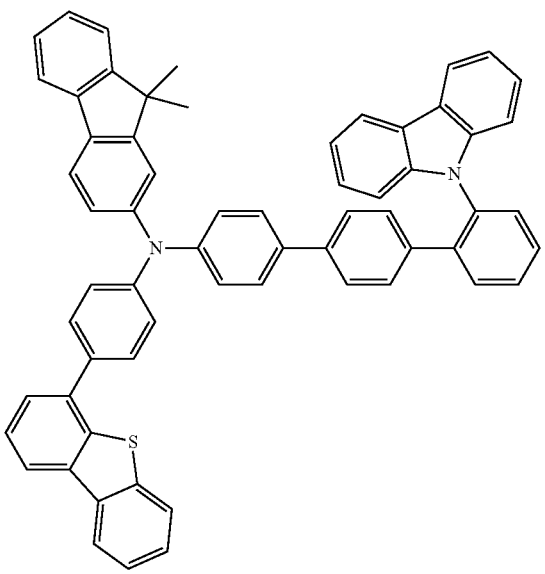
A1-33
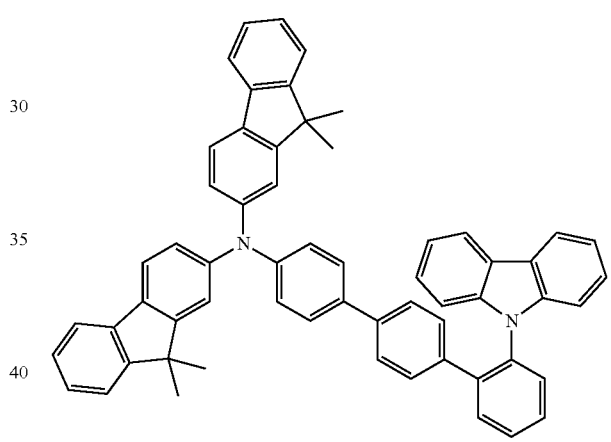
A1-31
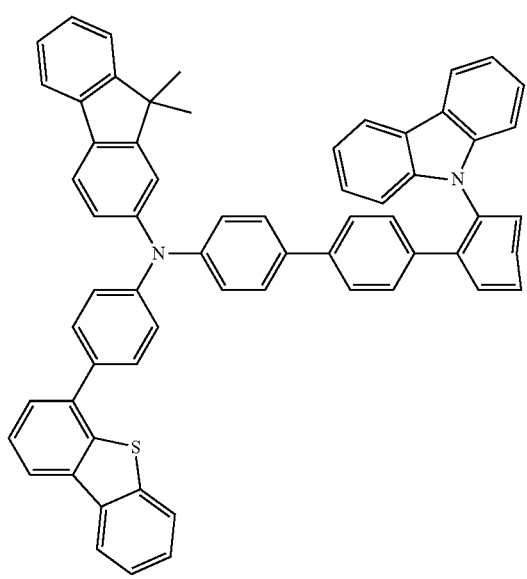
A1-34
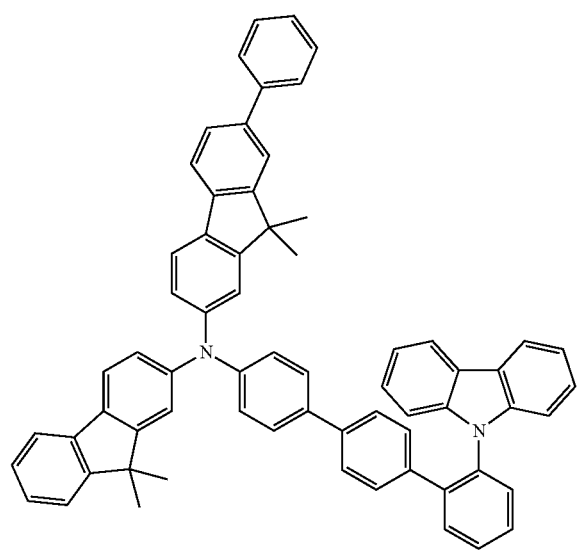

A1-35
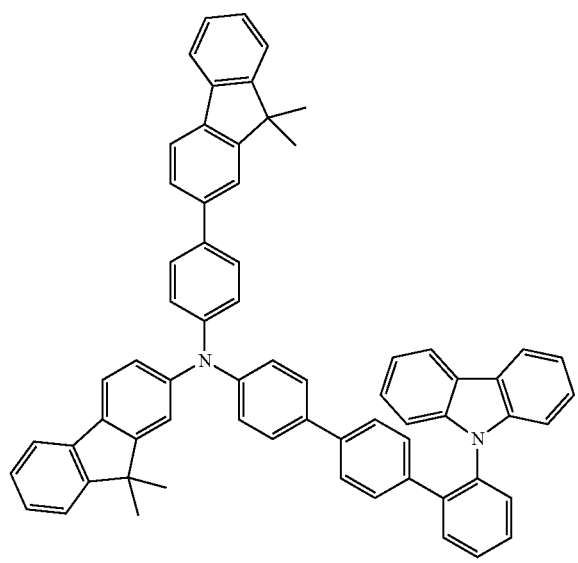
A1-36
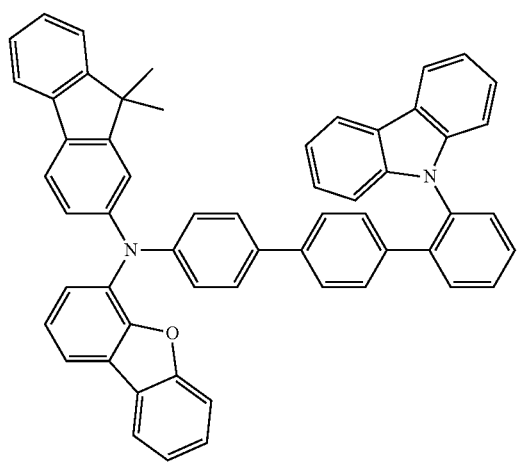
A1-37
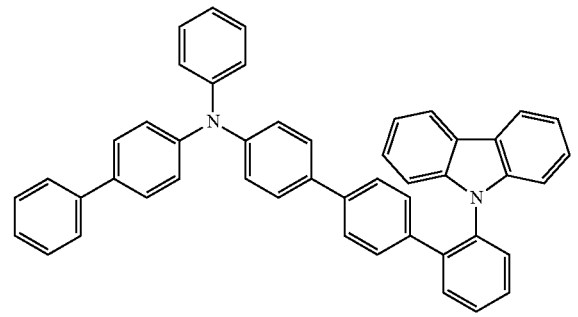
A1-38
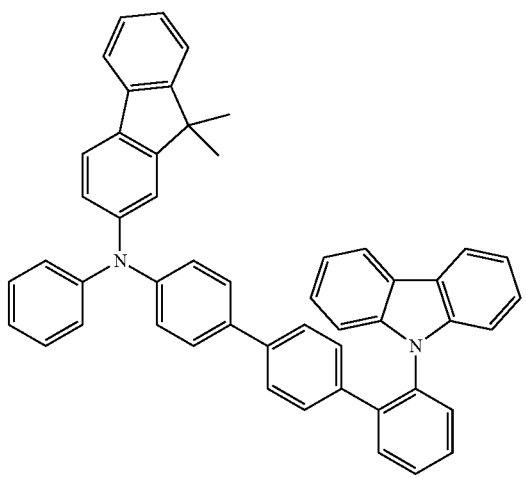
A1-39
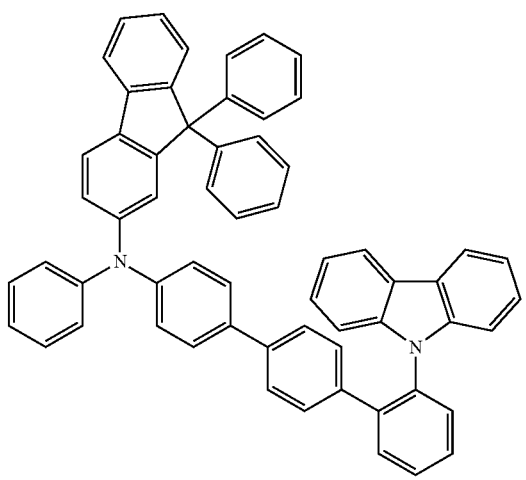
A1-40
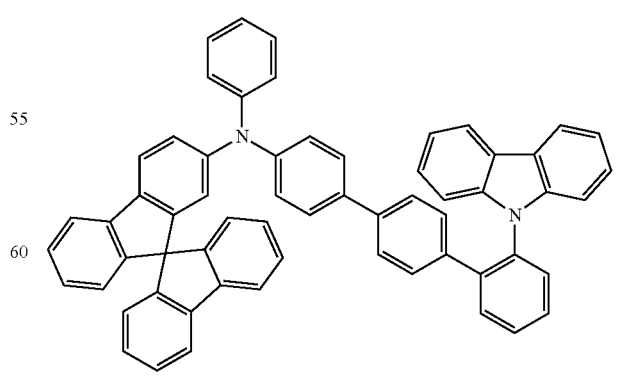

A1-41
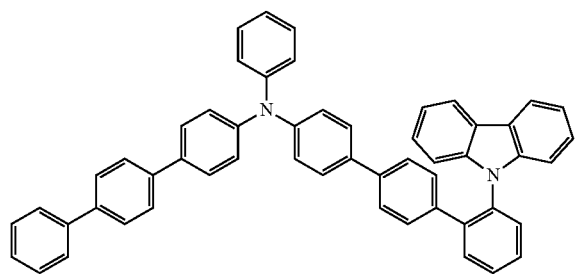
A1-42
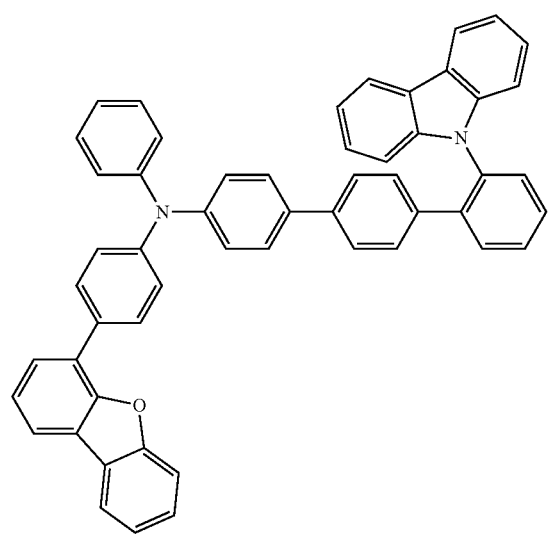
A1-43
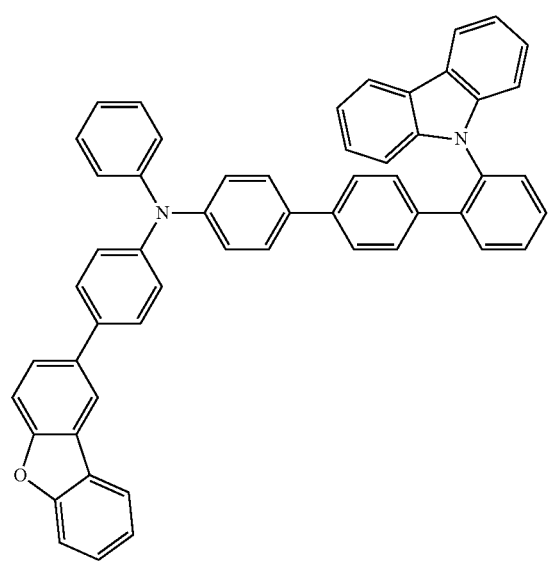
A1-44
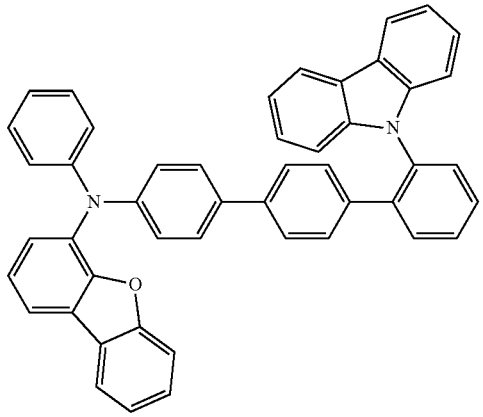
A1-45
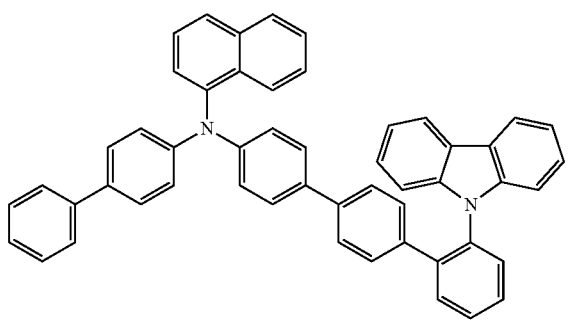
A1-46
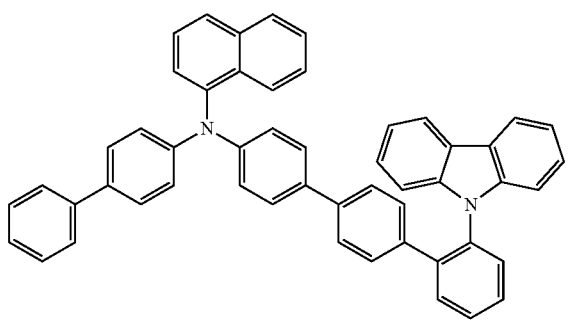

A1-47
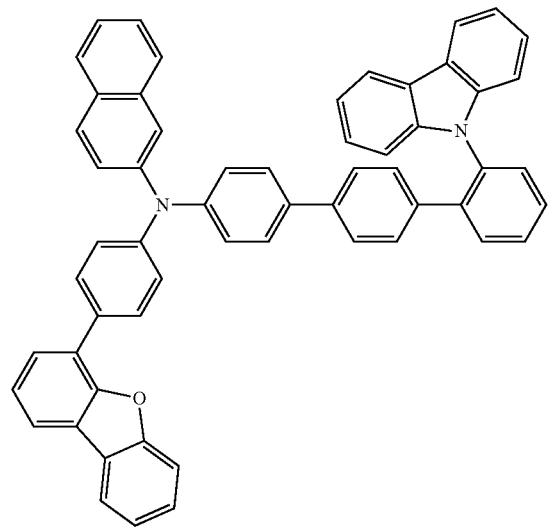
A1-48
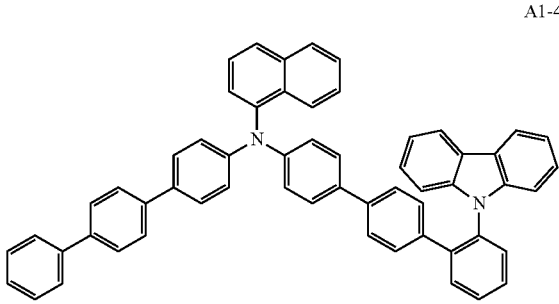
A2-1
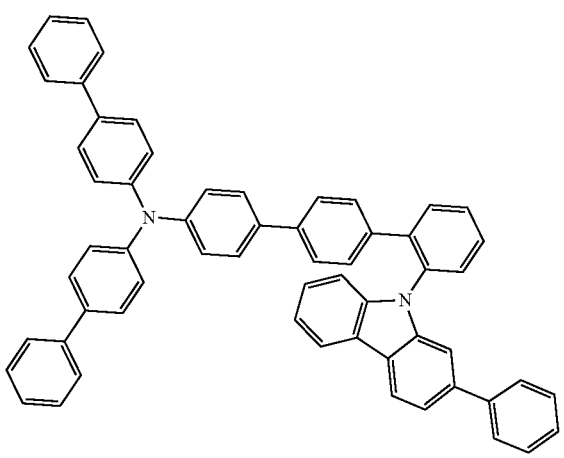
A2-2
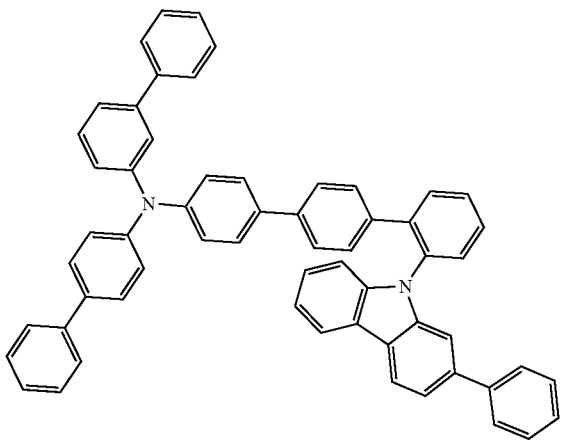
A2-3
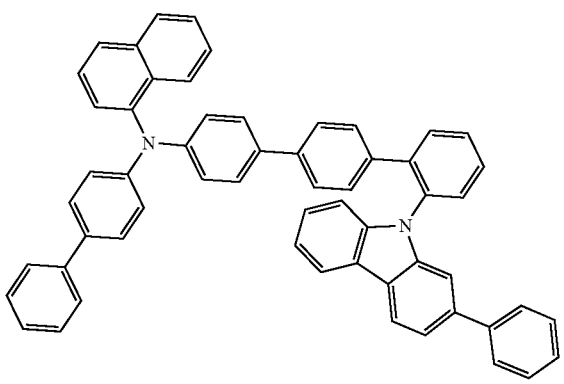
A2-4
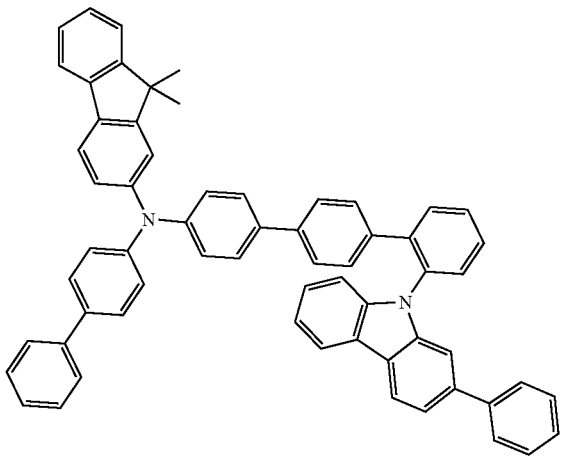

A2-5
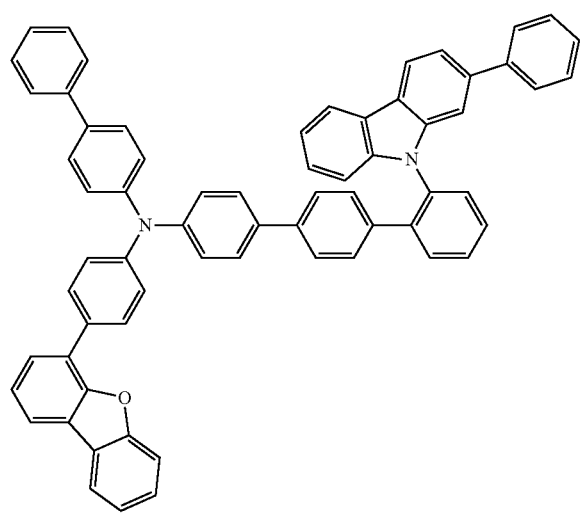
A2-8
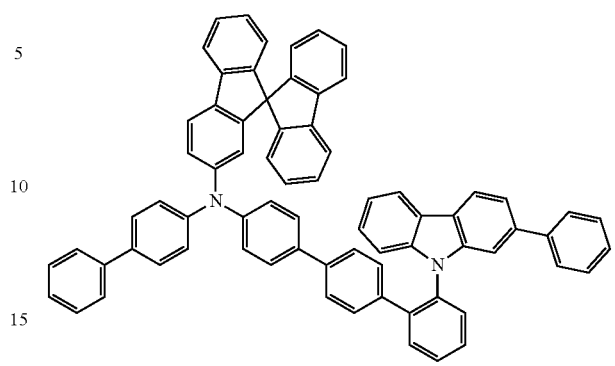
A2-6
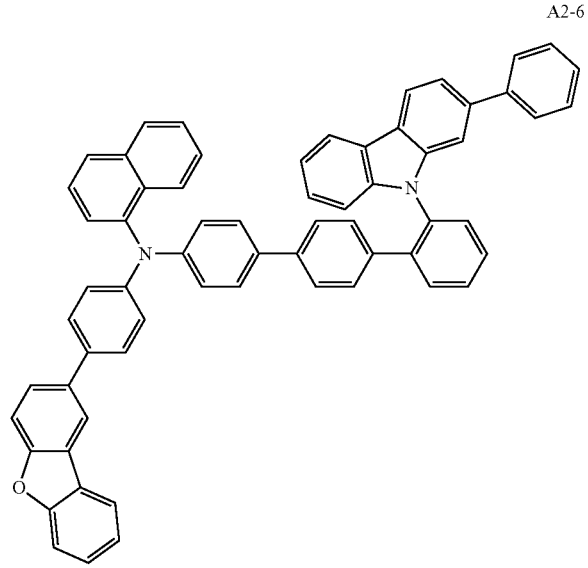
A2-9
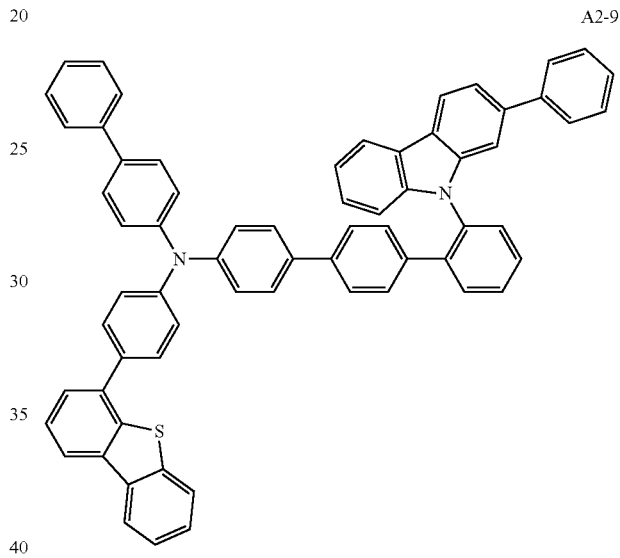
A2-7
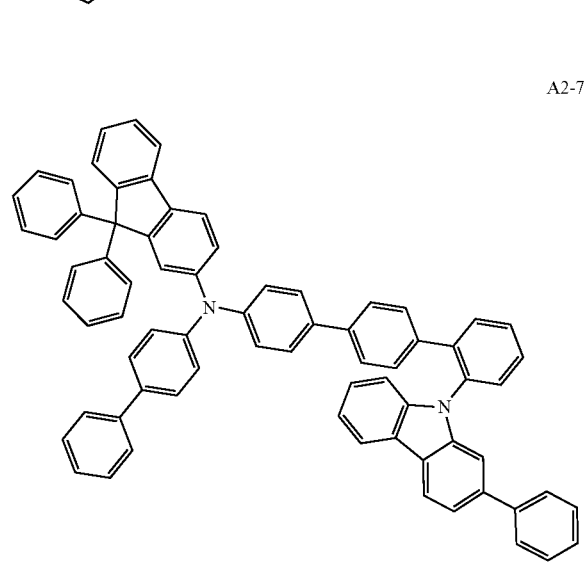
A2-10
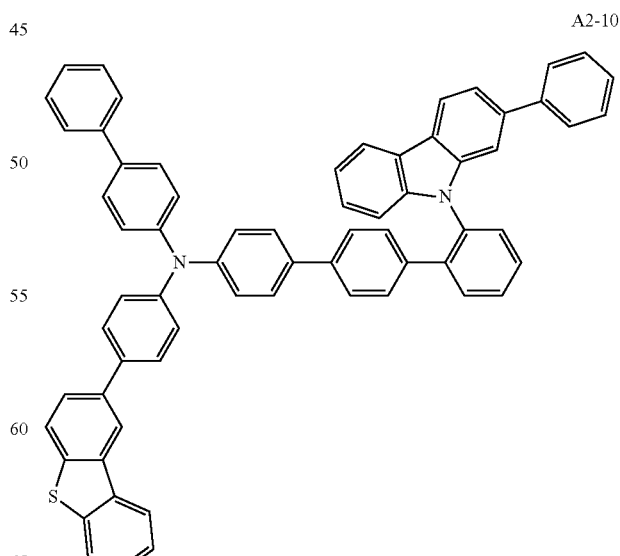

A2-11
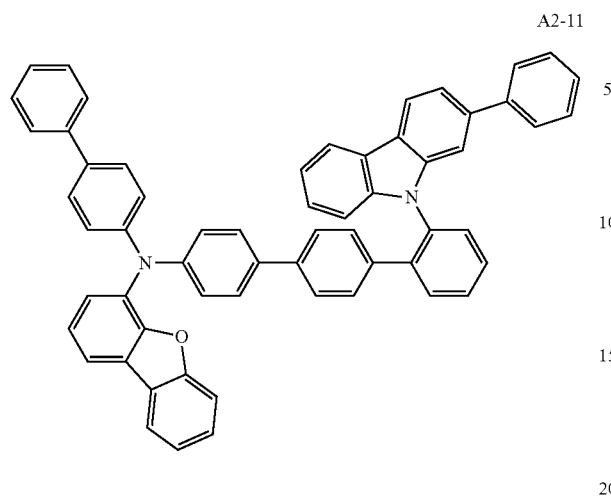
A2-12
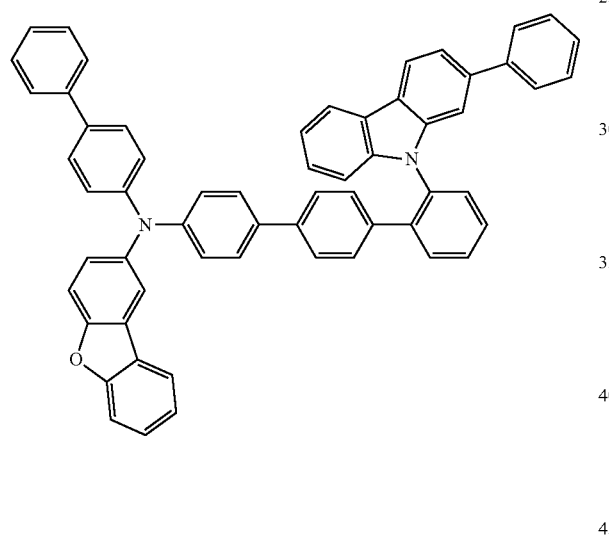
A2-13
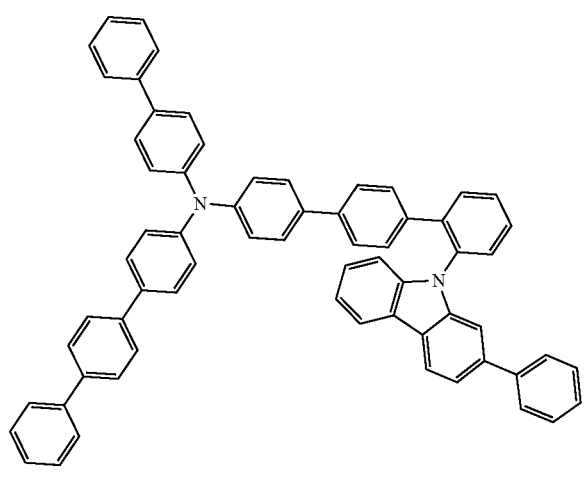
A2-14
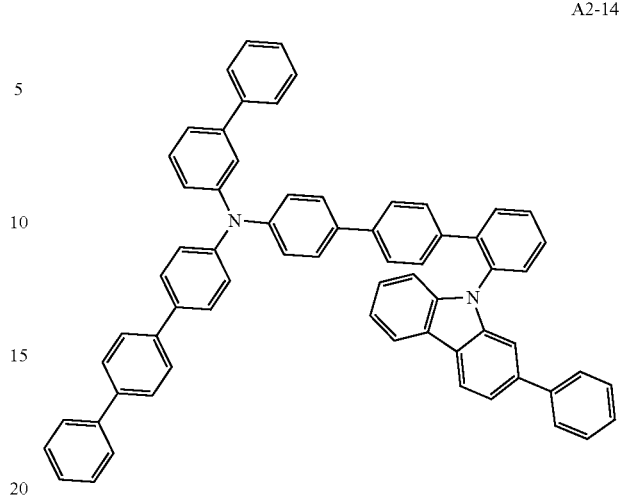
A2-15
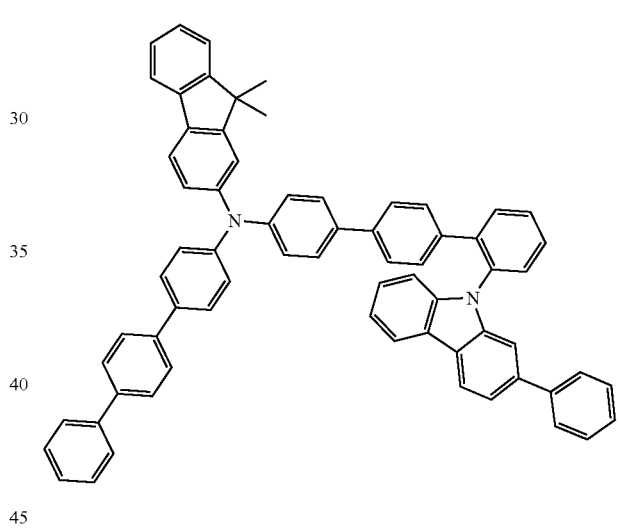
A2-16
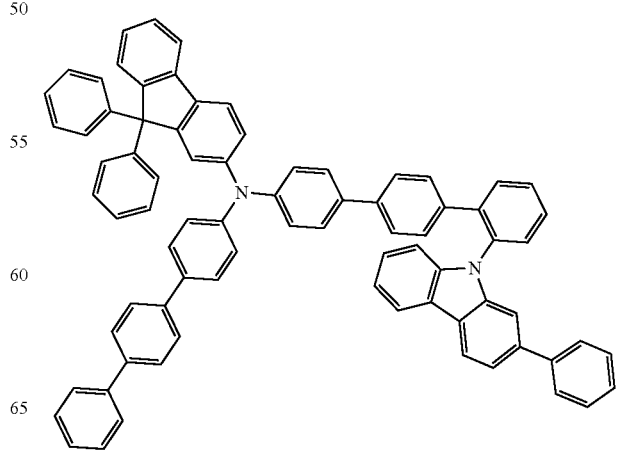

A2-17
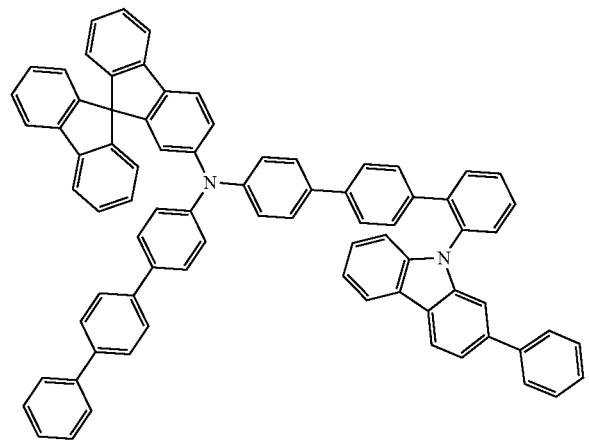
A2-20
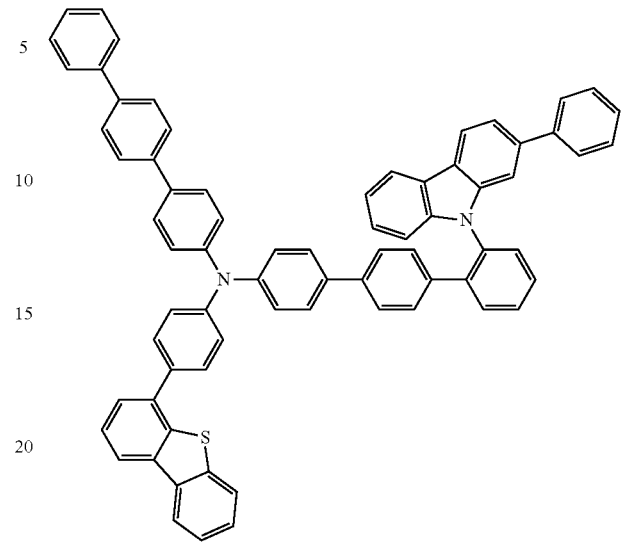
A2-18
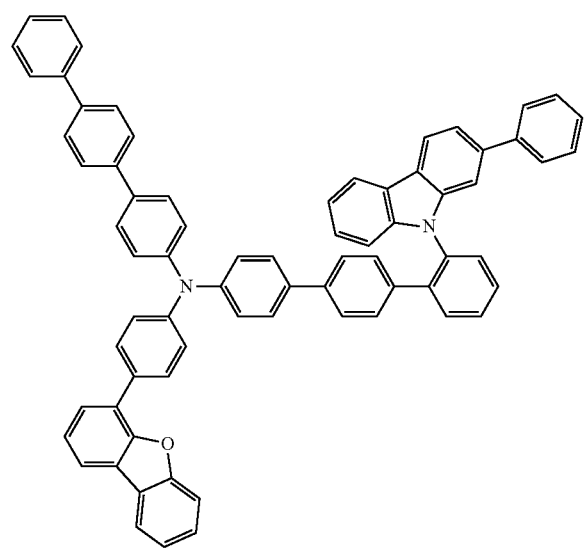
A2-21
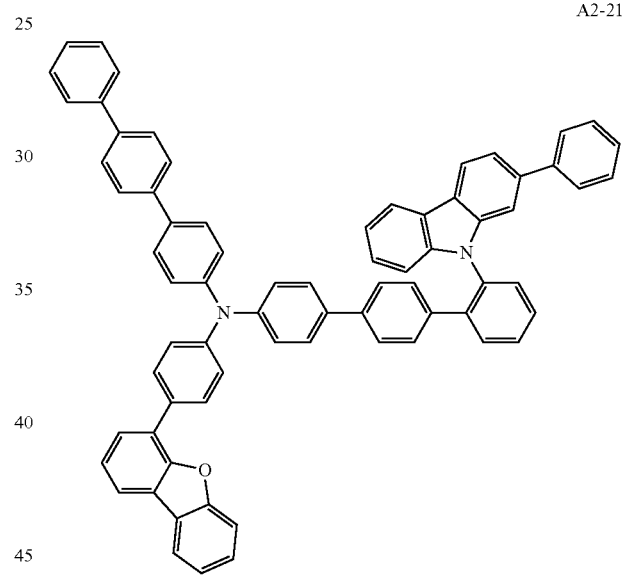
A2-19
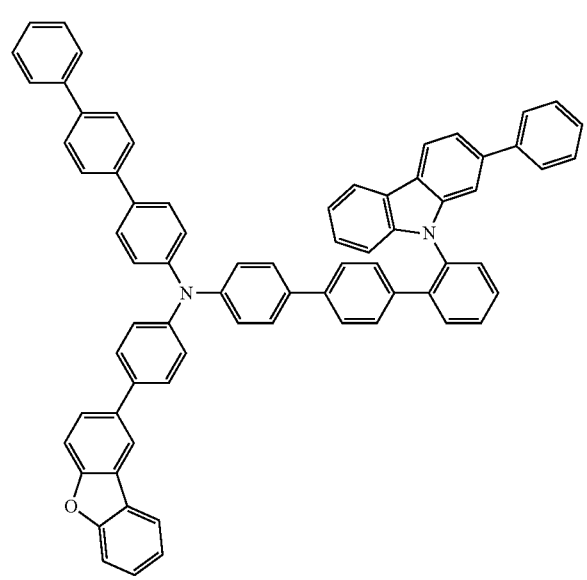
A2-22
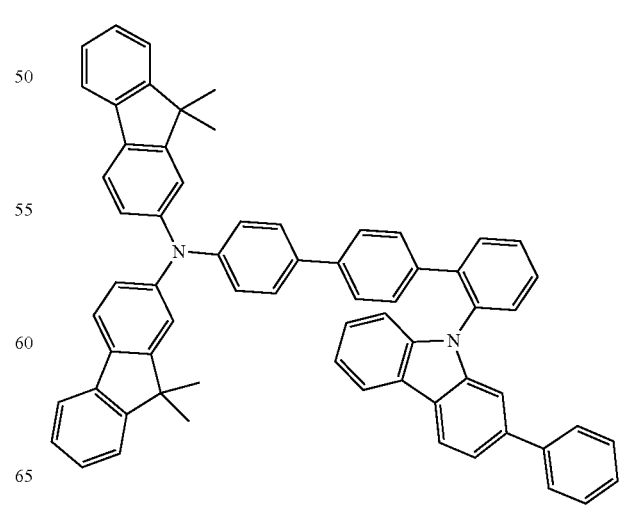

A2-23
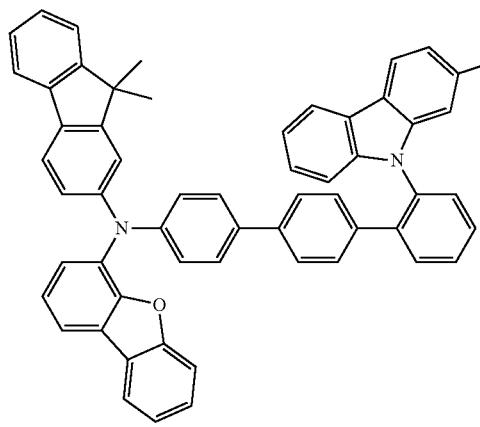
A2-24
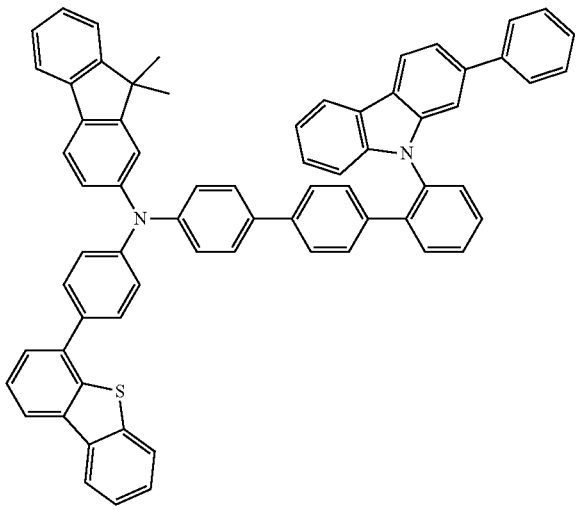
A2-25
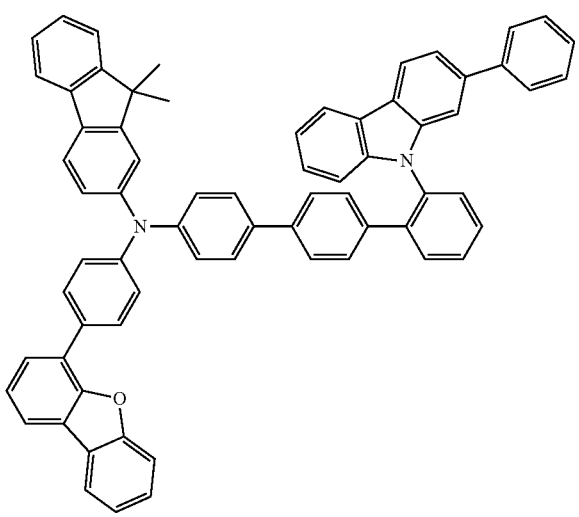
A2-26
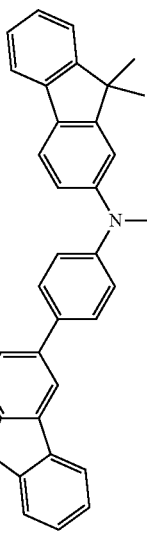
A2-27
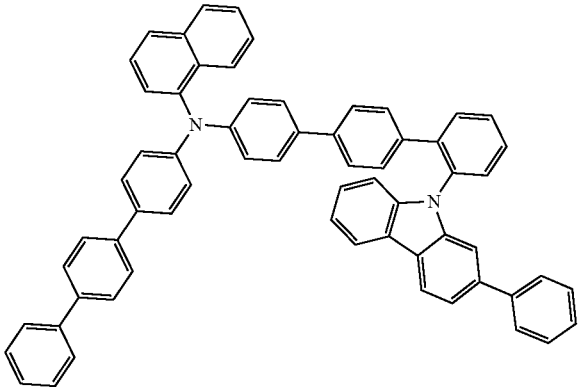
A2-28
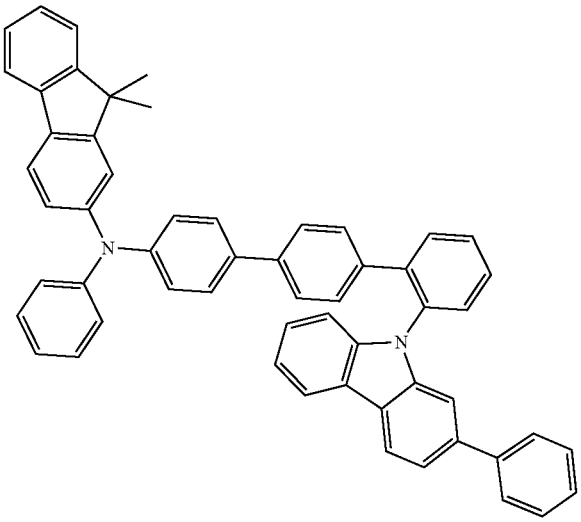

A2-29
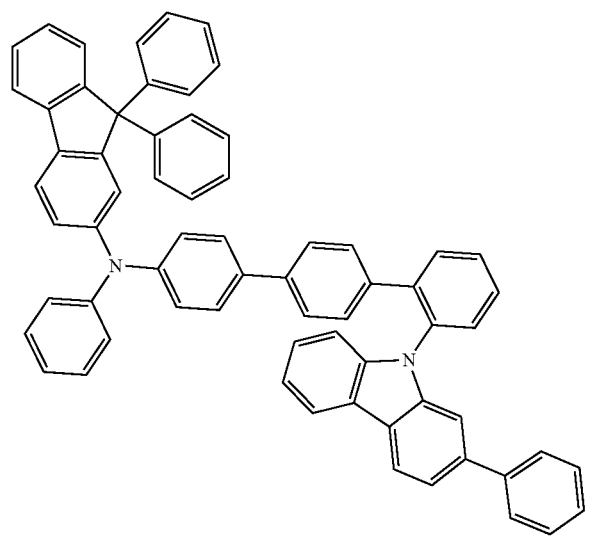
A2-30
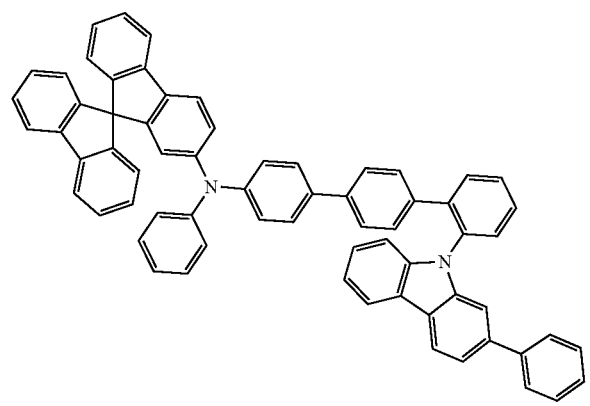
A2-31
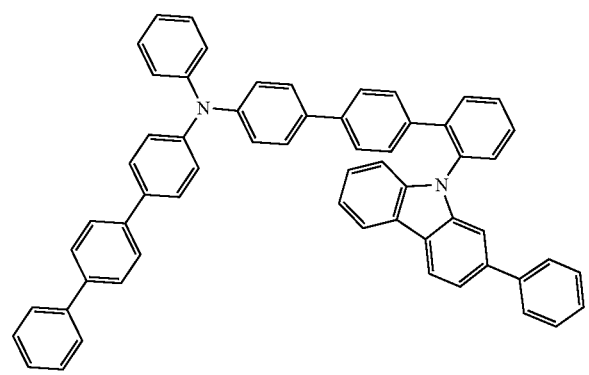
A2-32
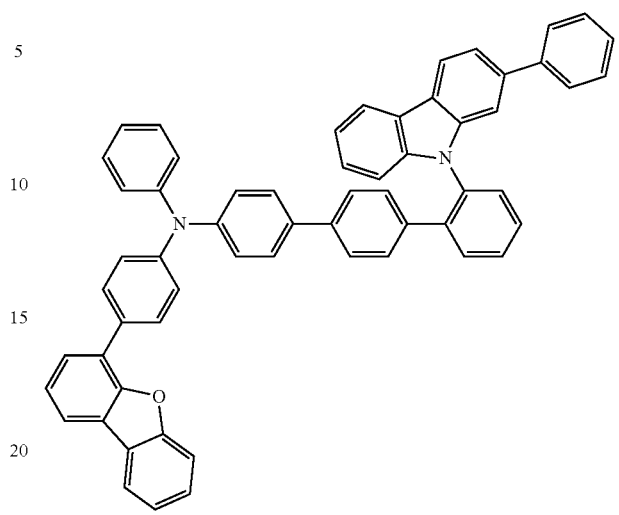
A2-33
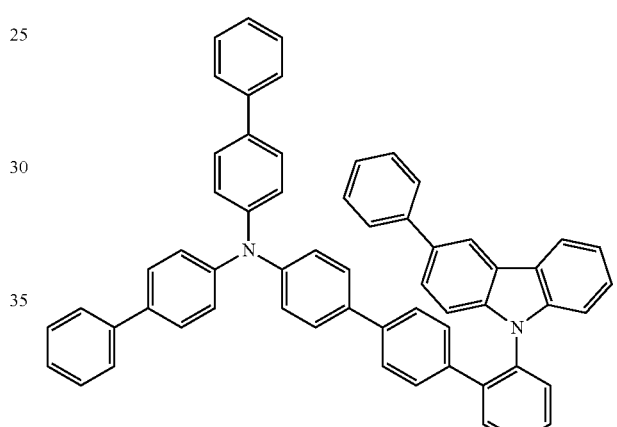
A2-34
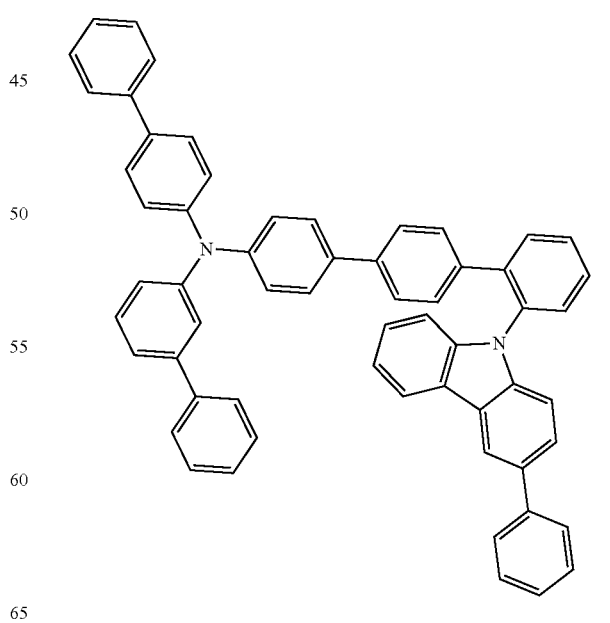

A2-35
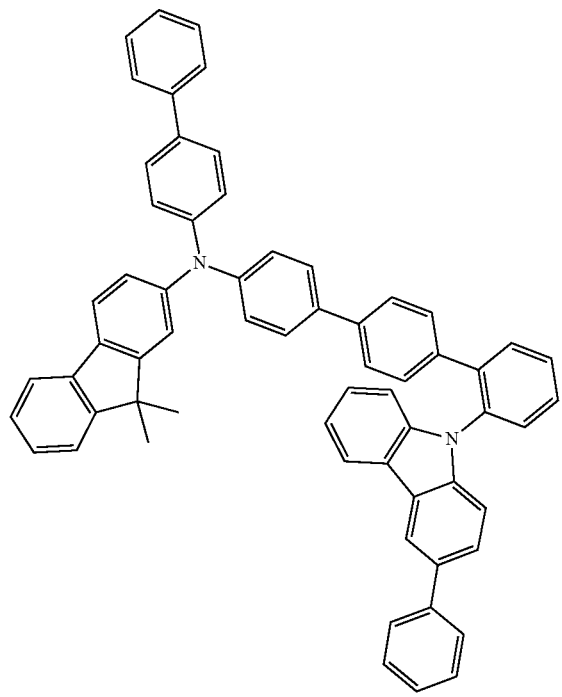
A2-36
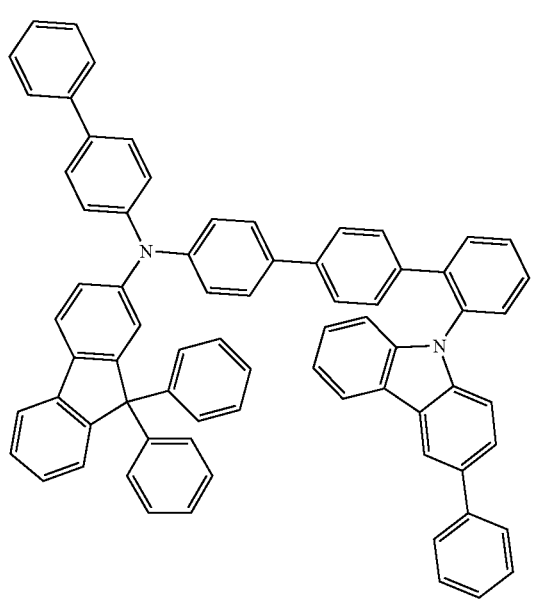
A2-37
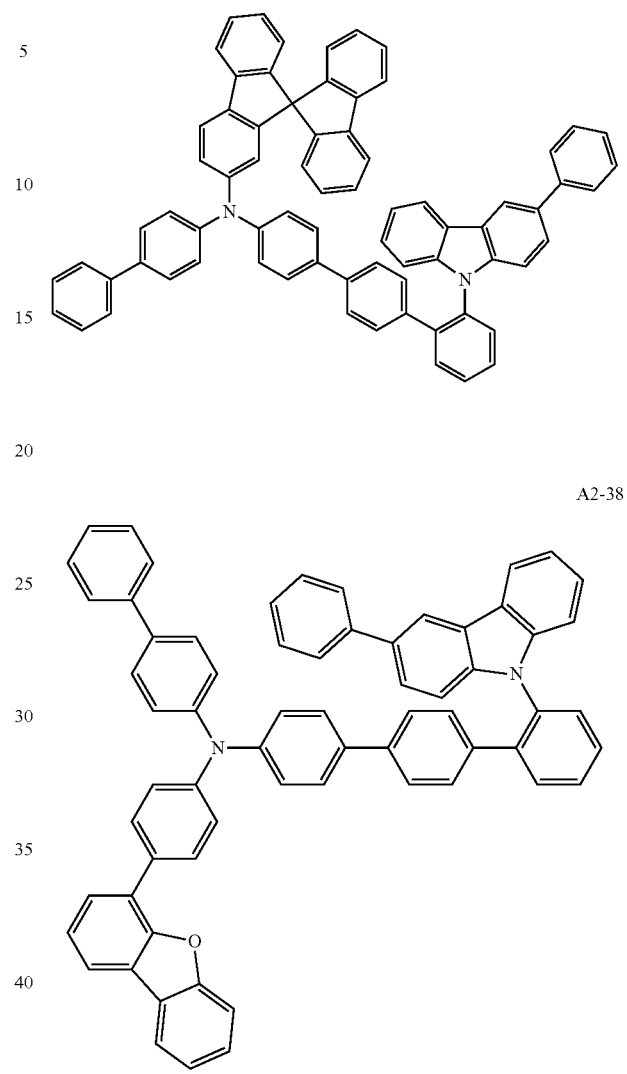
A2-38
A2-39
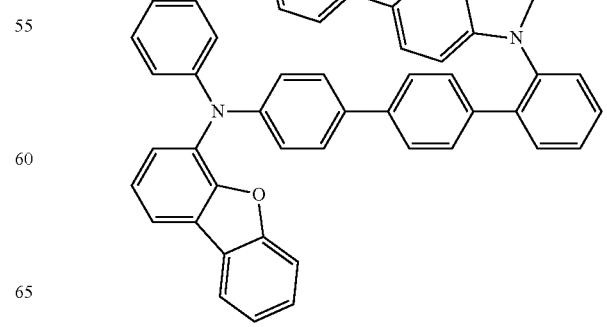

A2-40
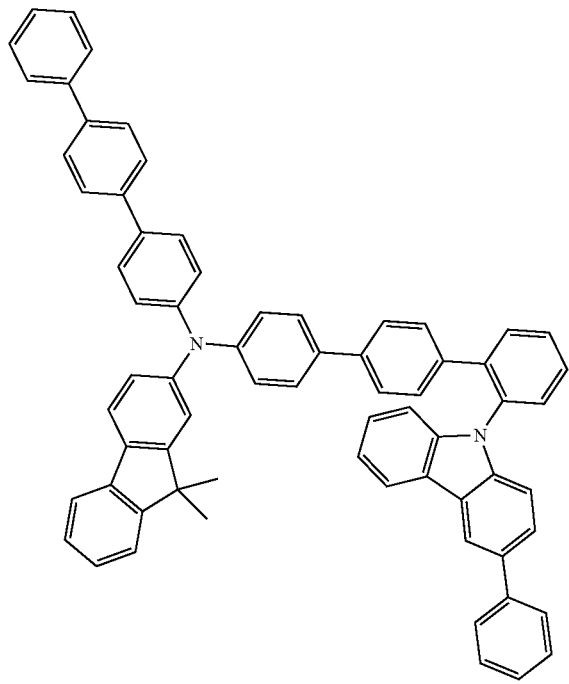
A2-43
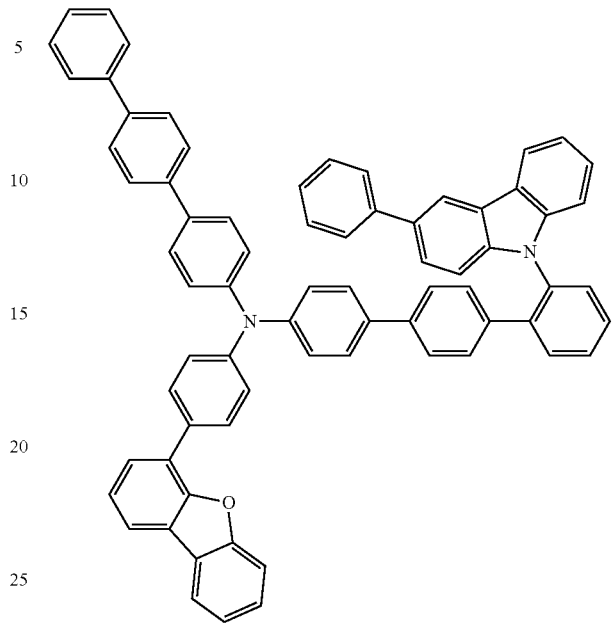
A2-41
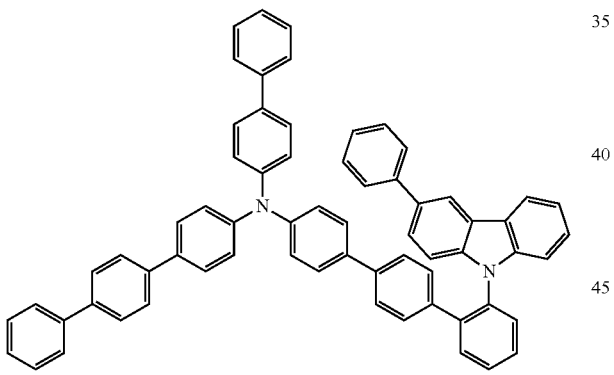
A2-42
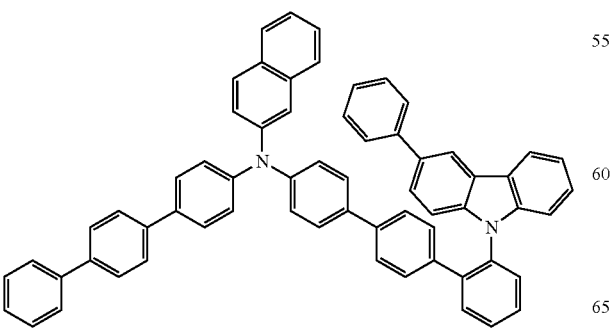
A2-44
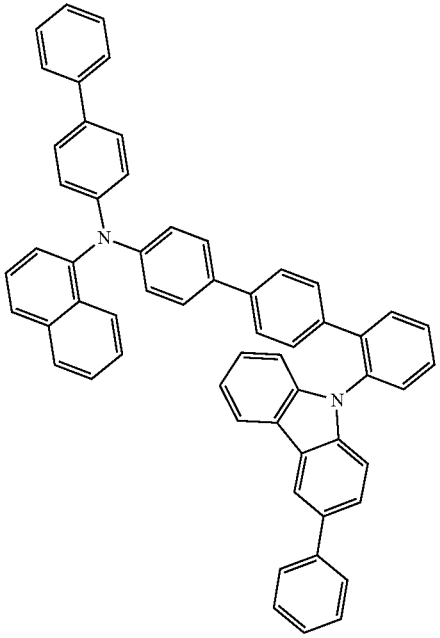

-continued
A2-45
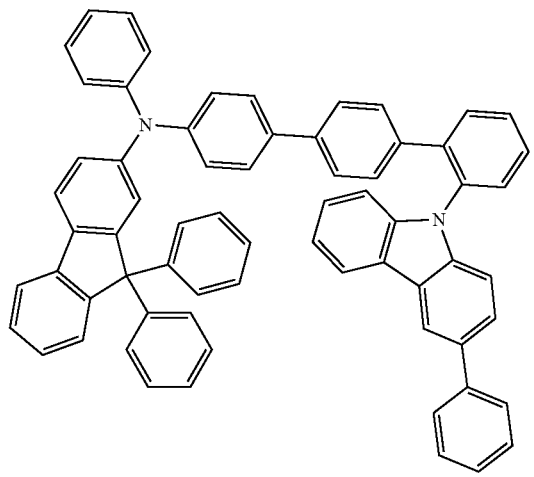
A2-46
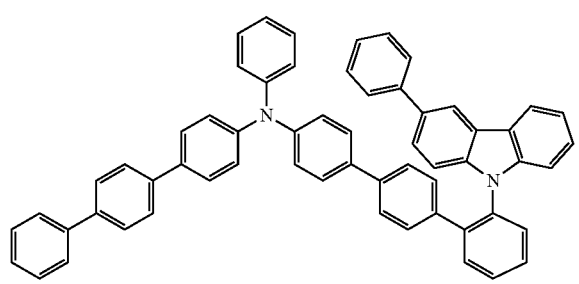
A2-47
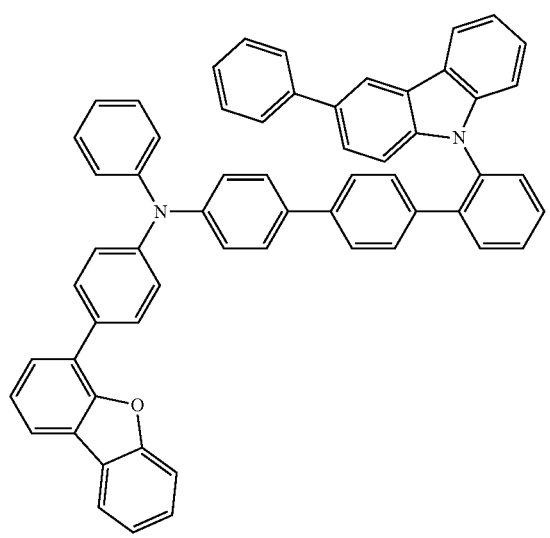
-continued
A2-48
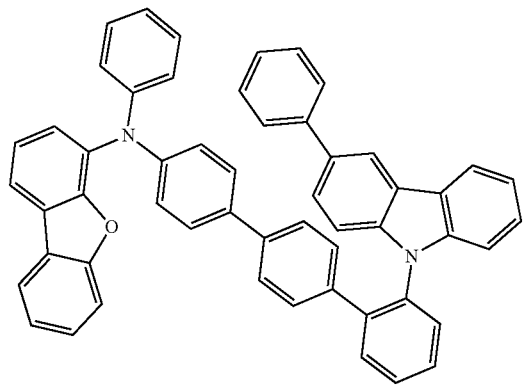
A2-49
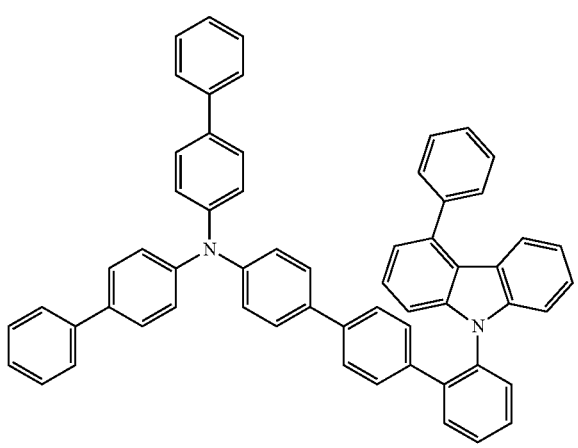
A2-50
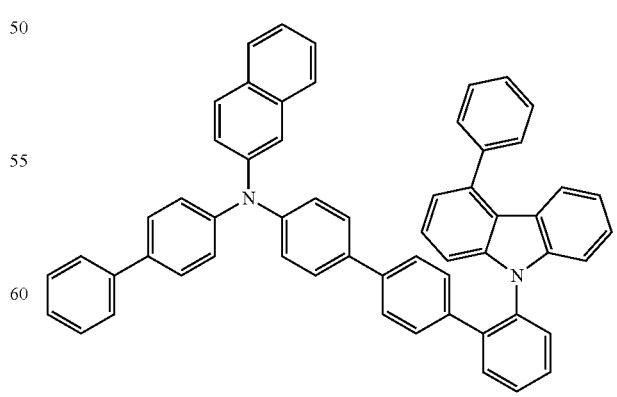

A2-51
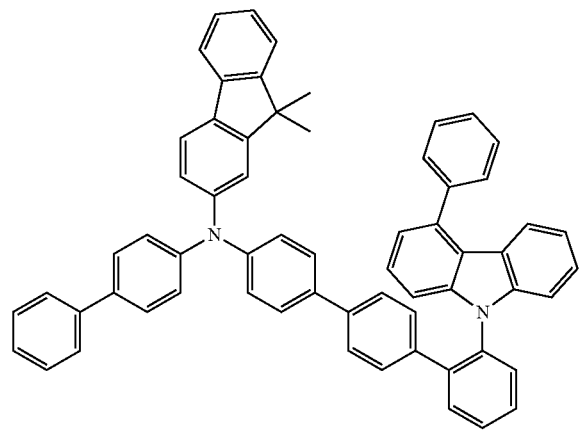
A2-54
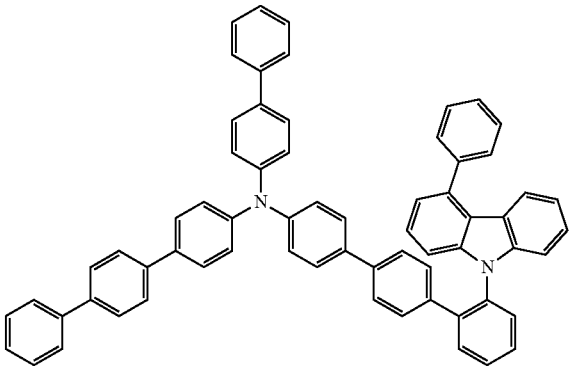
A2-52
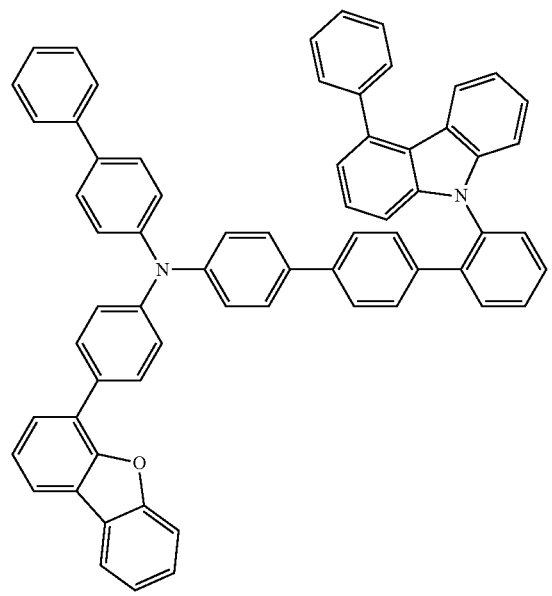
A2-55
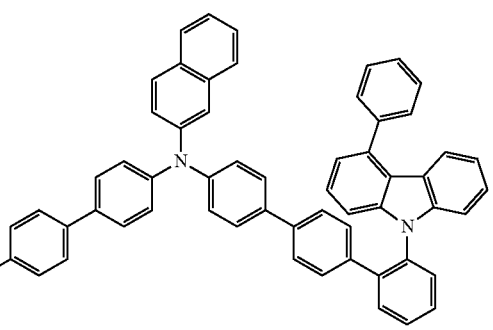
A2-56
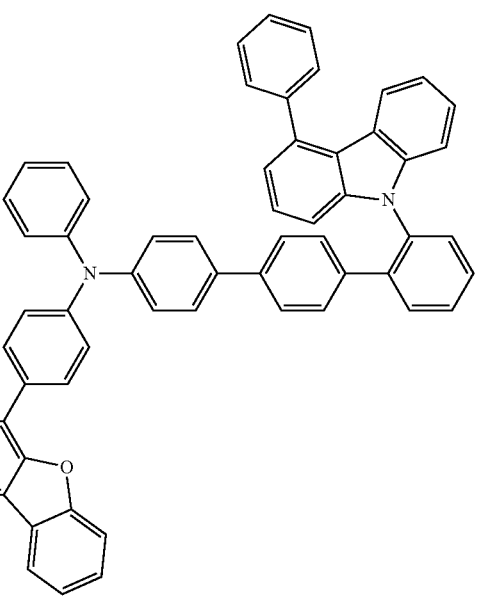
A2-53
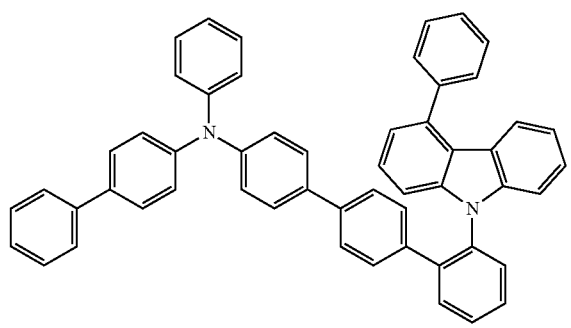

A2-57
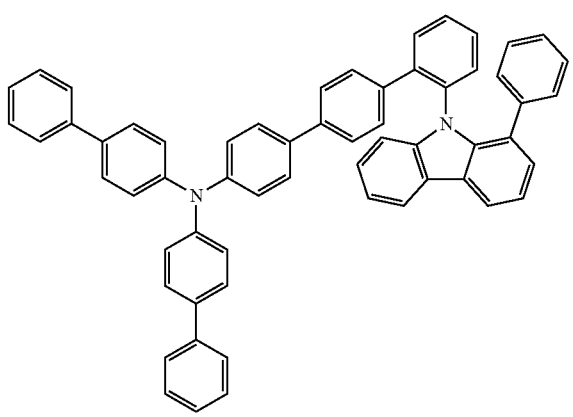
A2-60
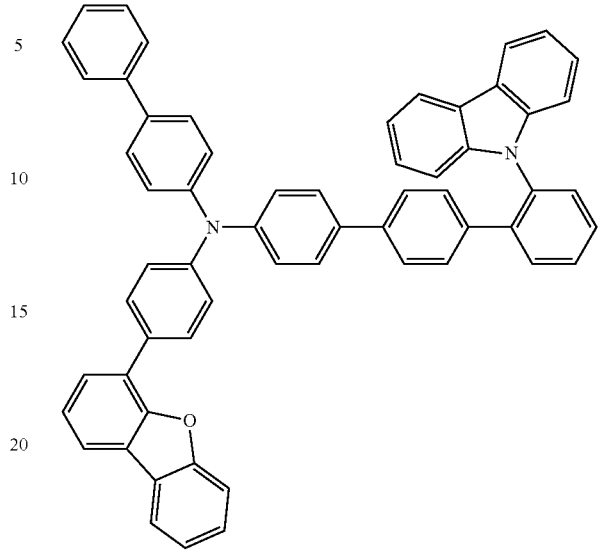
A2-58
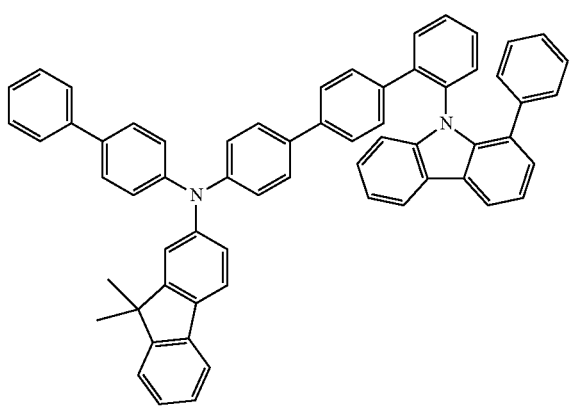
A2-61
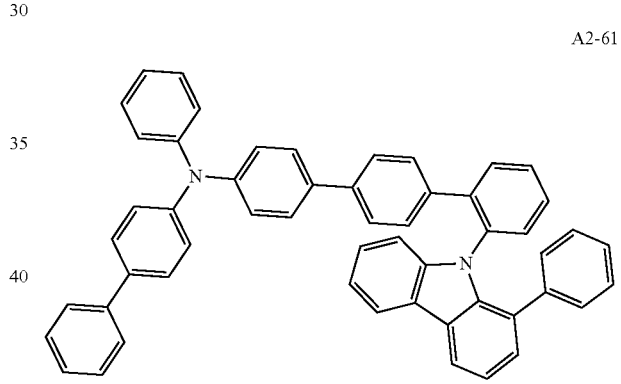
A2-59
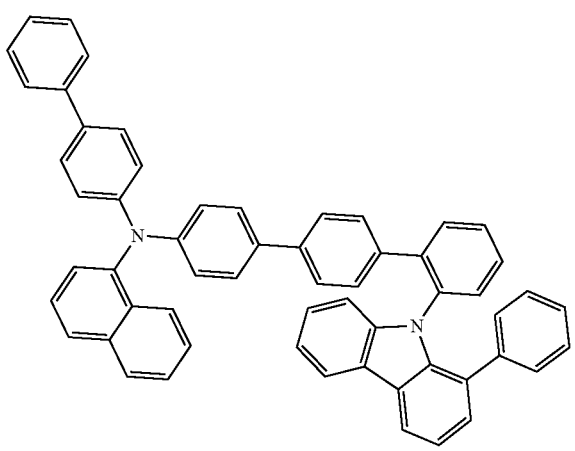
A2-62
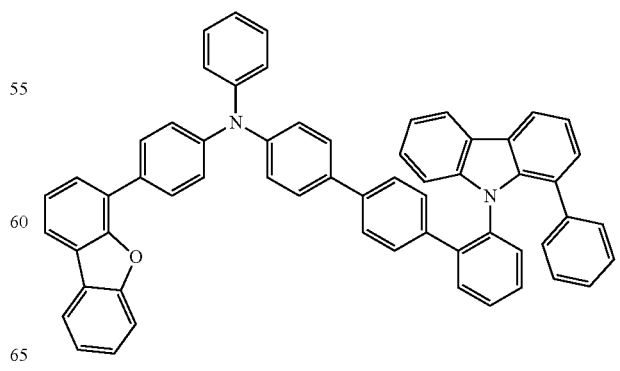

A3-1
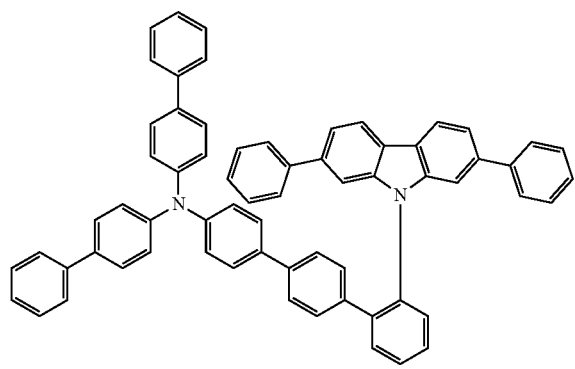
A3-2
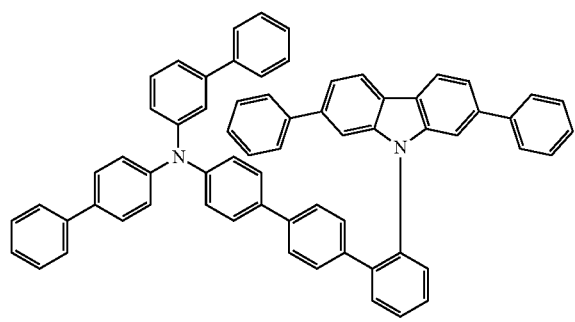
A3-3
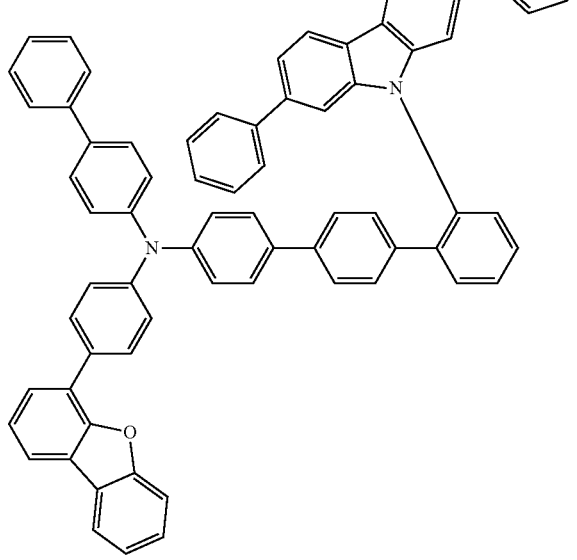
A3-4
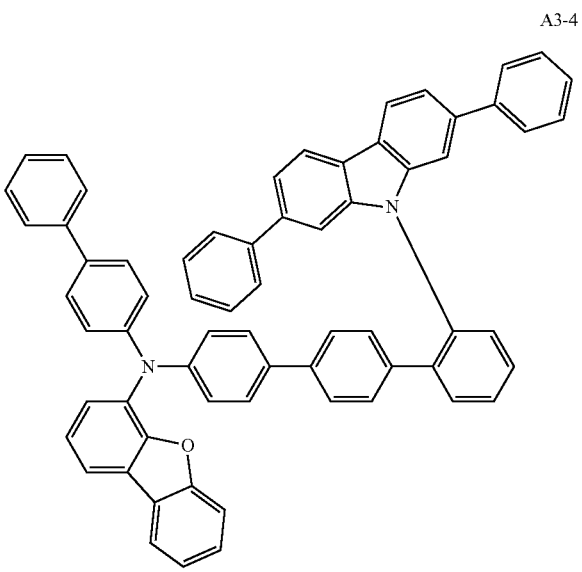
A3-5
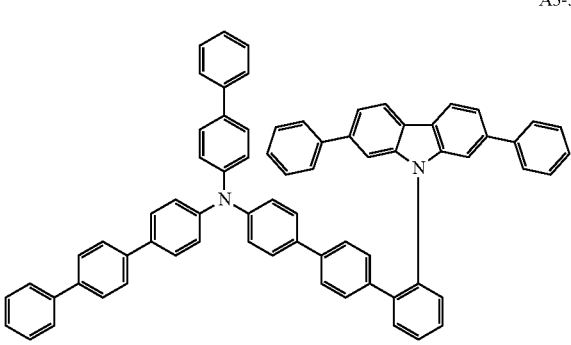
A3-6
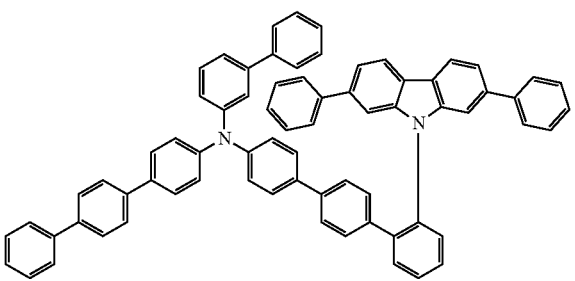
A3-7
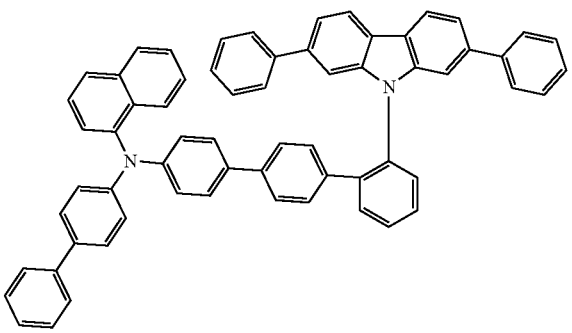

A3-8
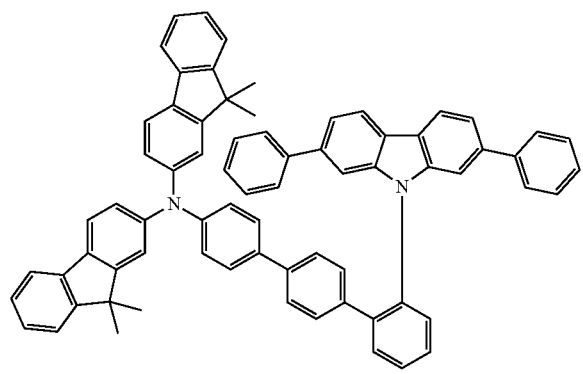
A3-9
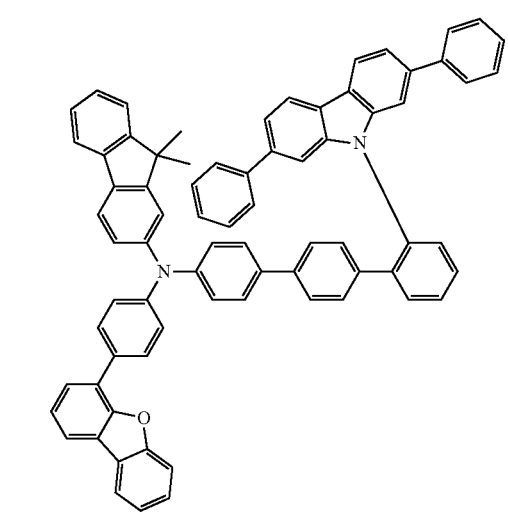
A3-10
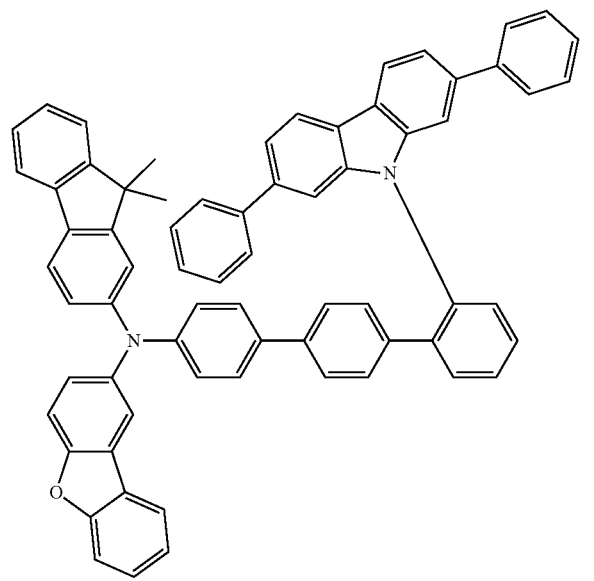
A3-11
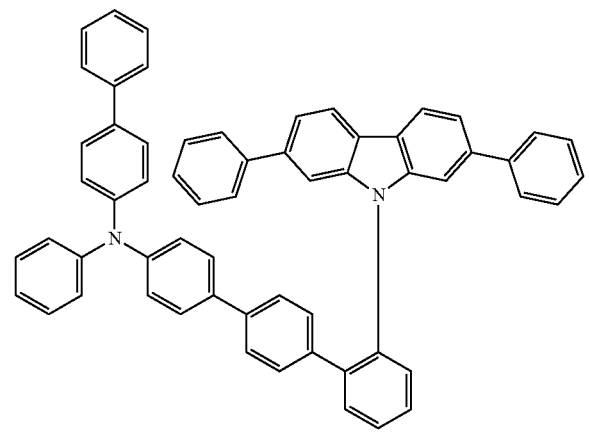
A3-12
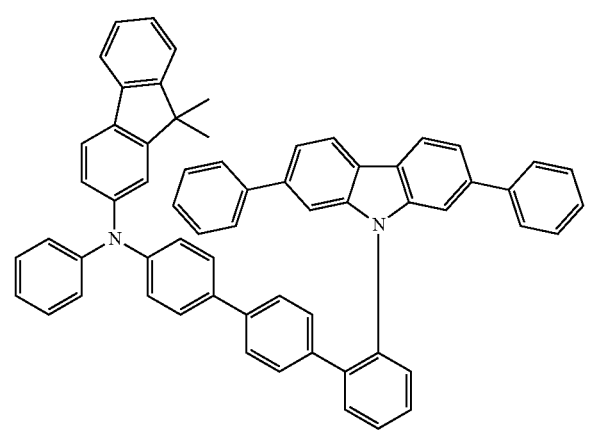
A3-13
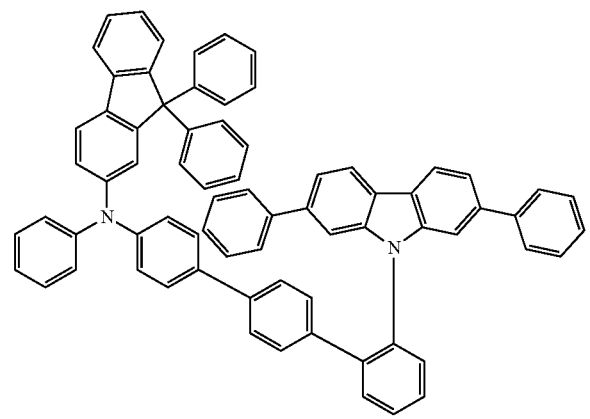

A3-14
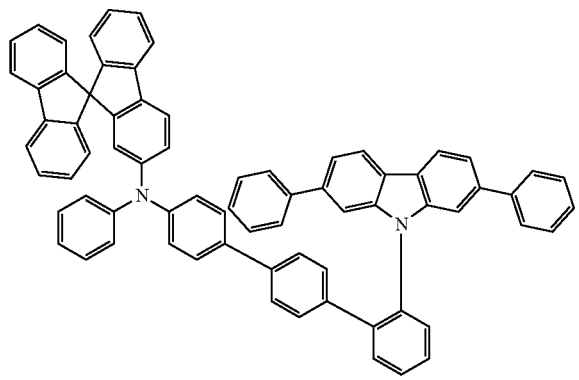
A3-17
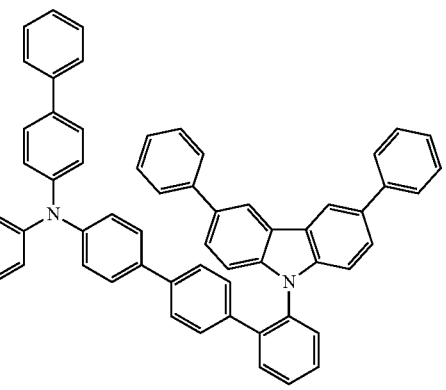
A3-15
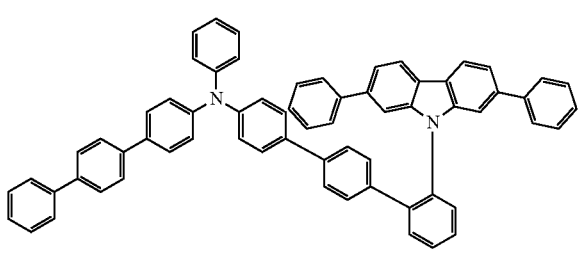
A3-16
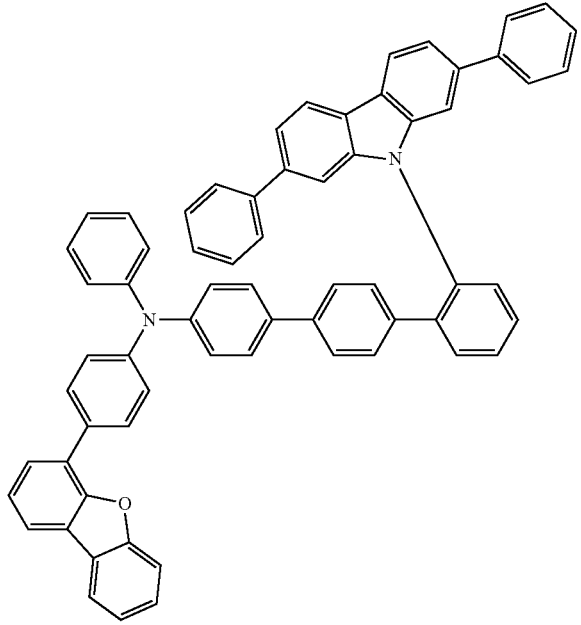
A3-18
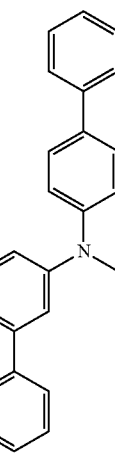
A3-19
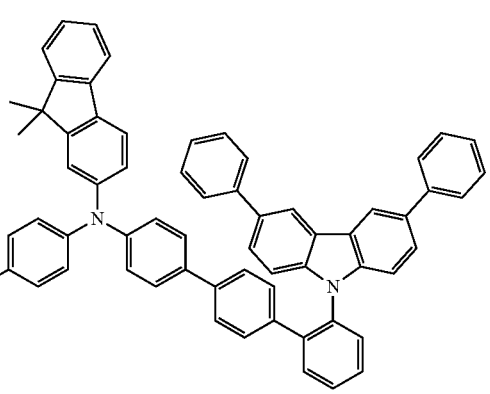

A3-20
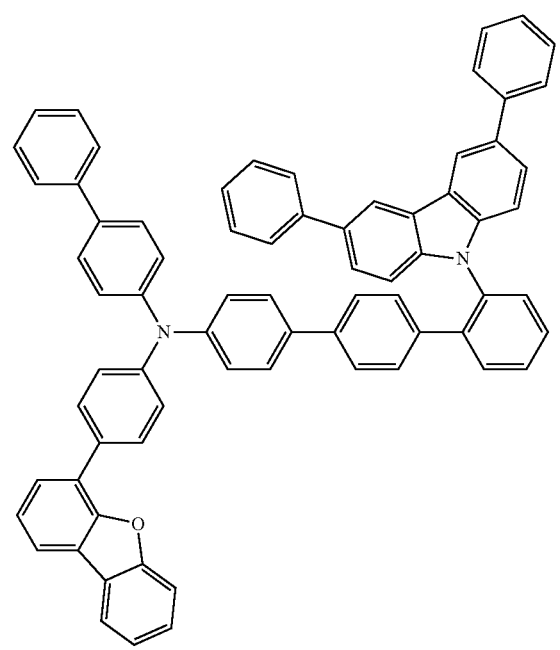
A3-21
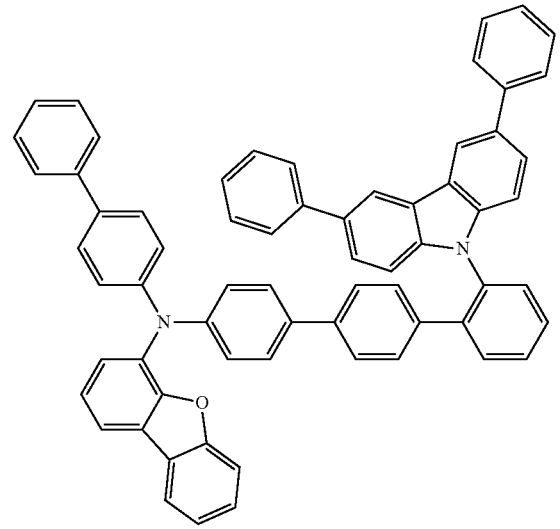
A3-22
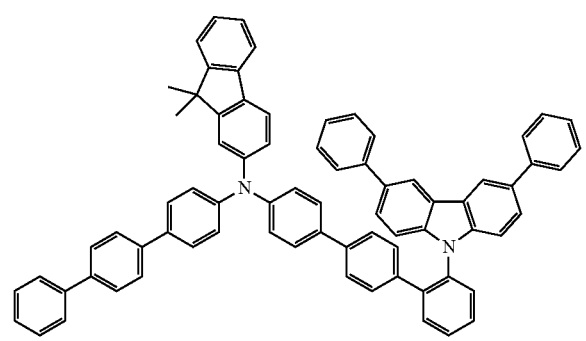
A3-23
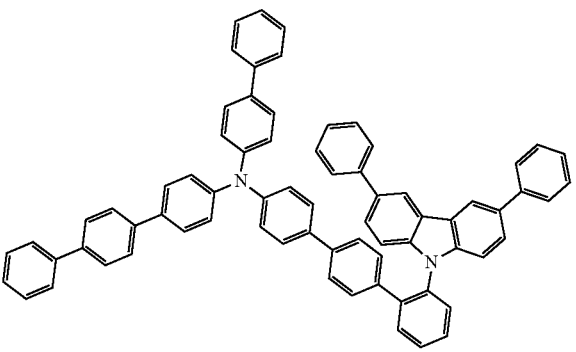
A3-24
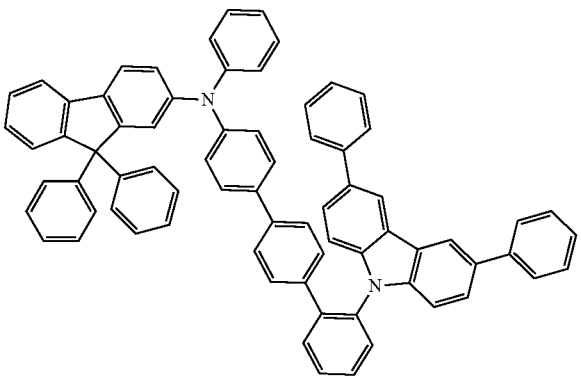
A3-25
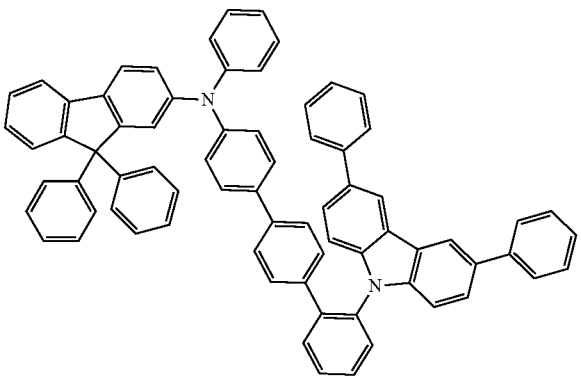
A3-26
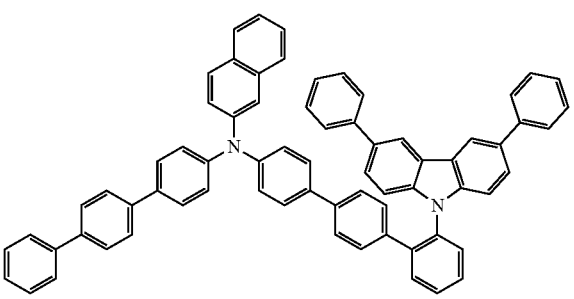

A3-27
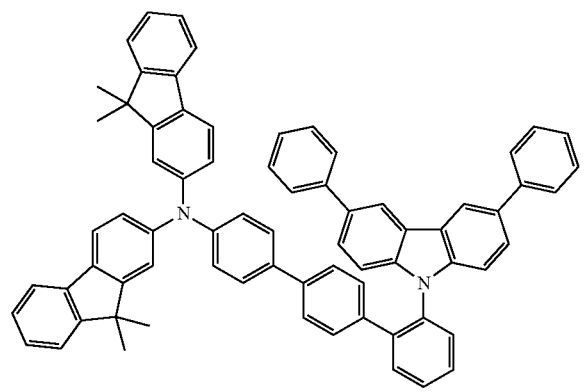
A3-28
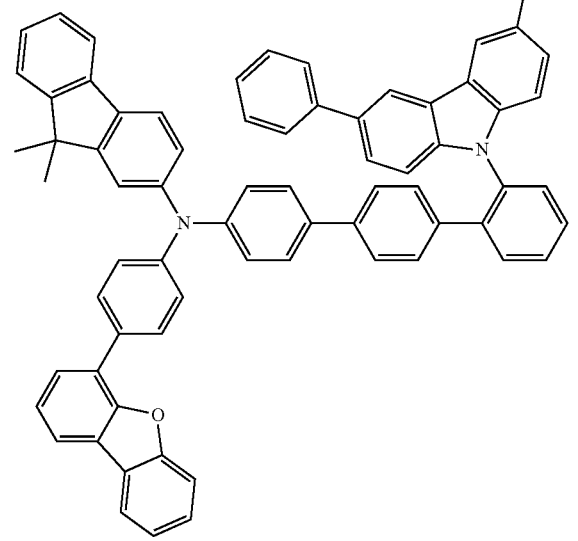
A3-29
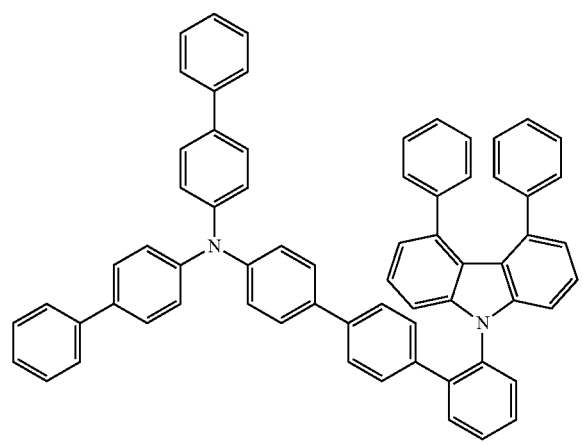
A3-30
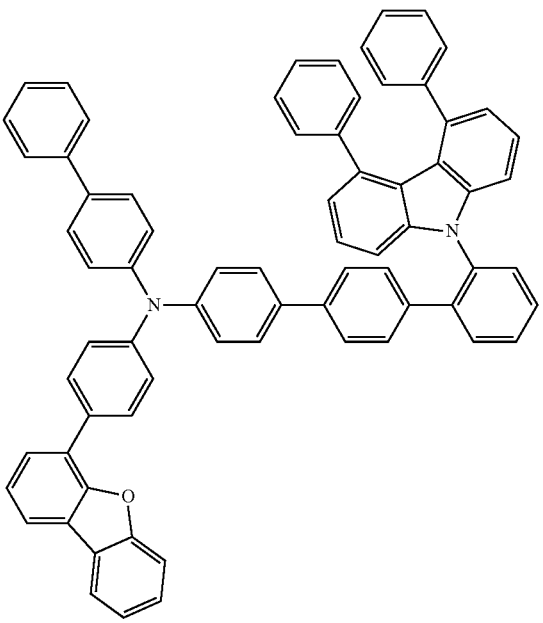
A3-31
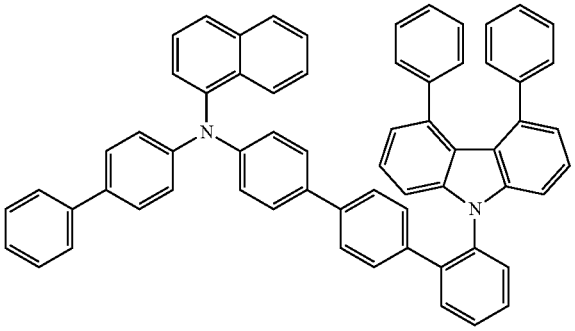
A3-32

-continued
A3-33
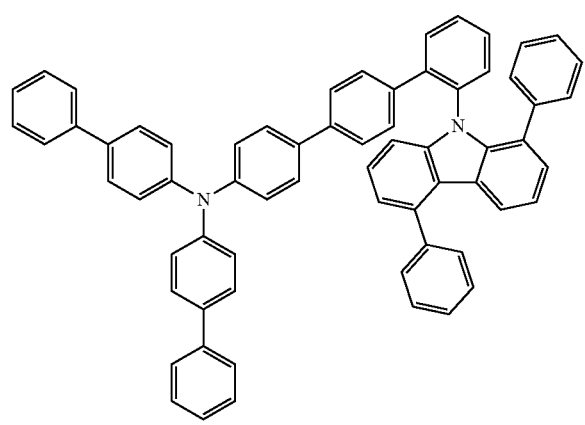
A3-36
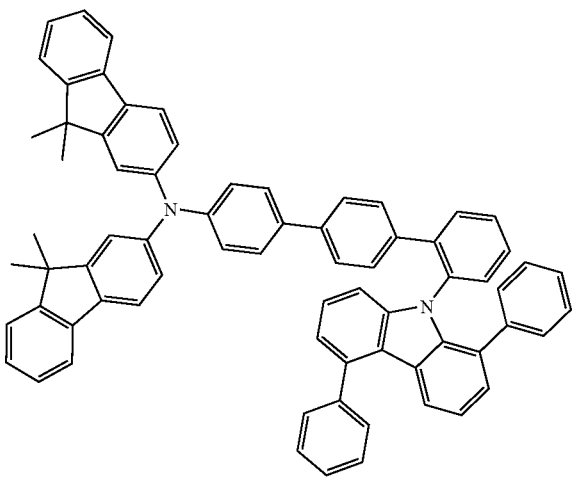
A3-34
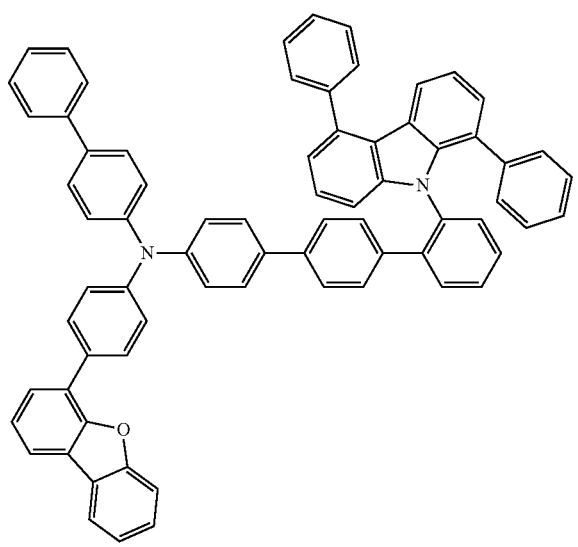
A3-37
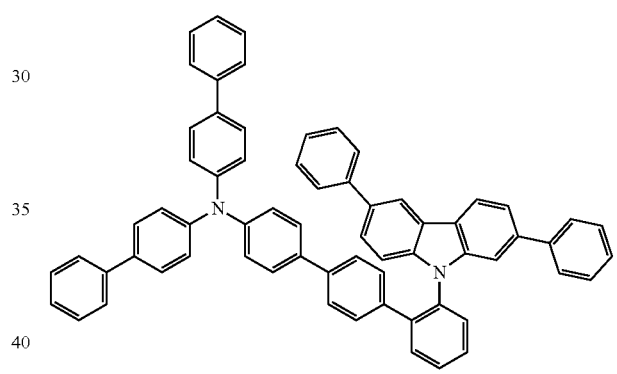
A3-35
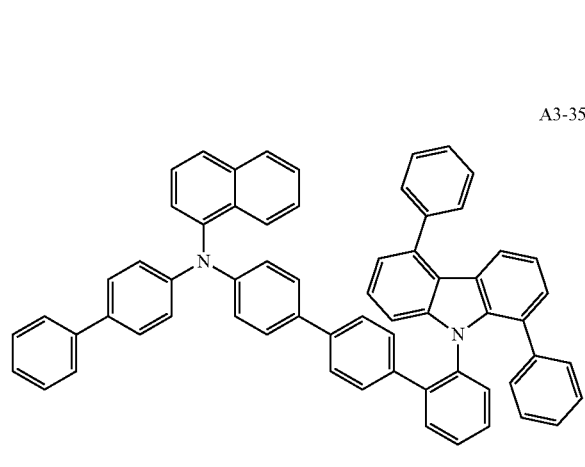
A3-38
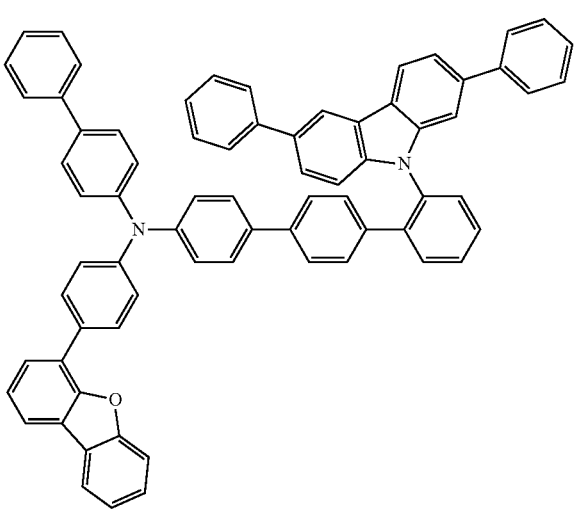

A3-39
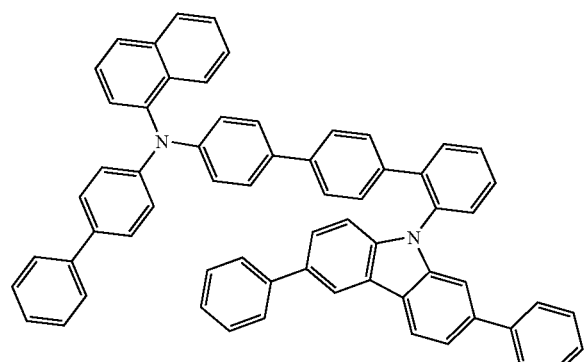
A4-3
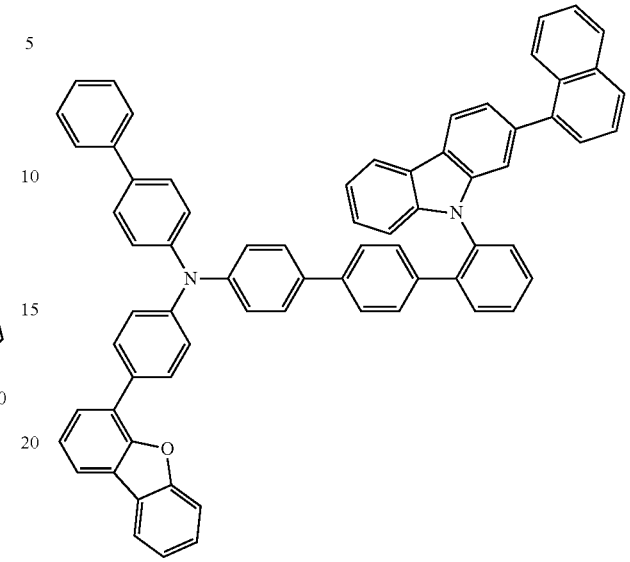
A3-40
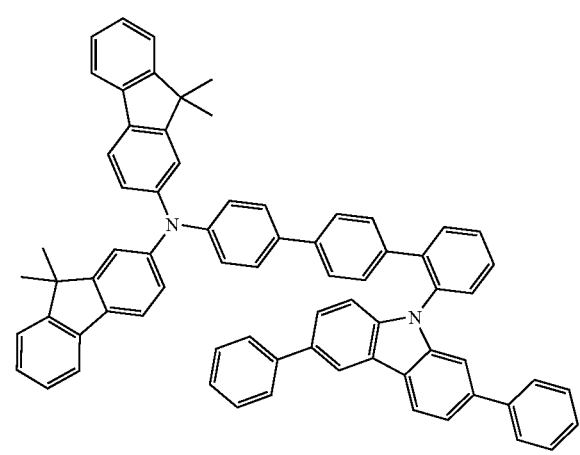
A4-4
A4-1
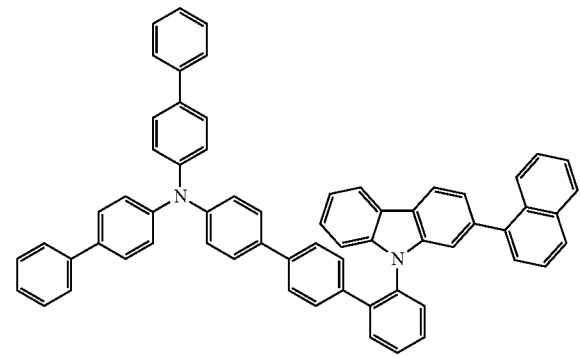
A4-2
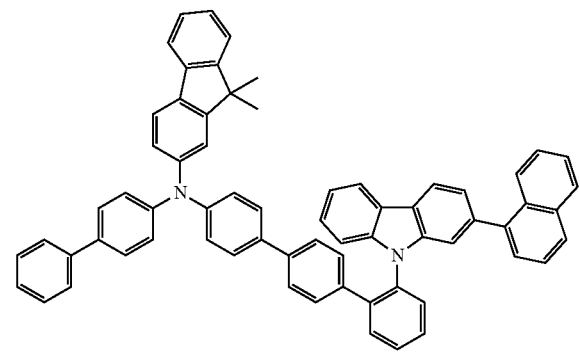
A4-5
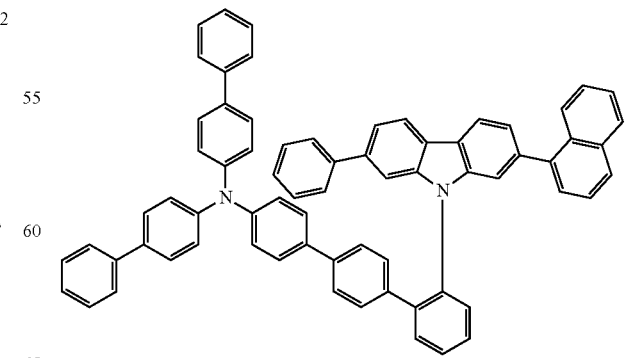

-continued
A4-6
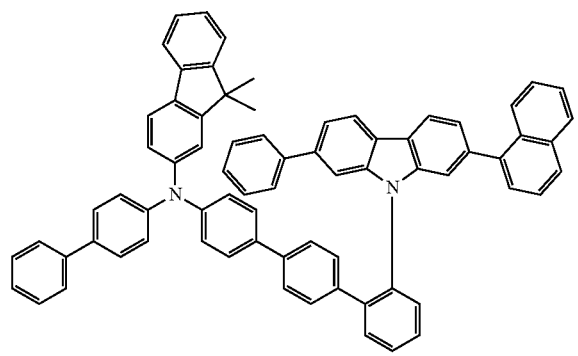
A4-7
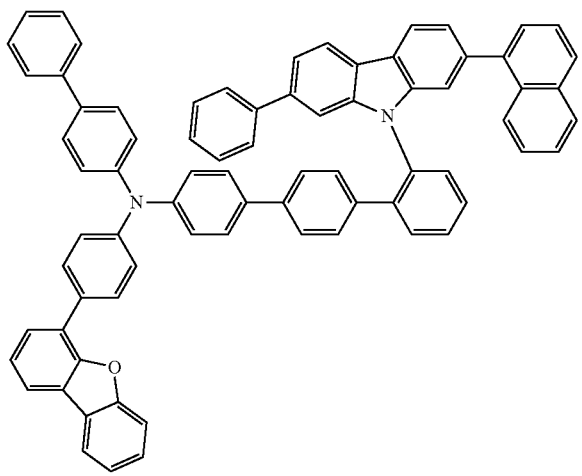
A4-8
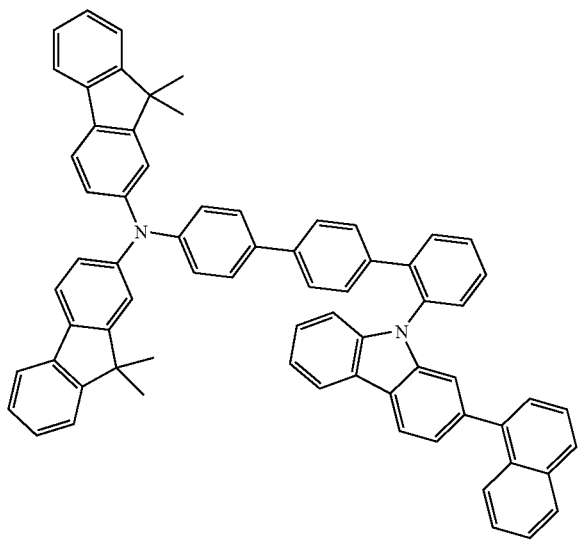
-continued
A4-9
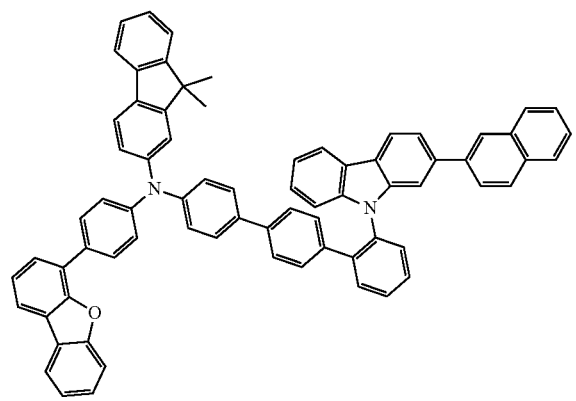
A4-10
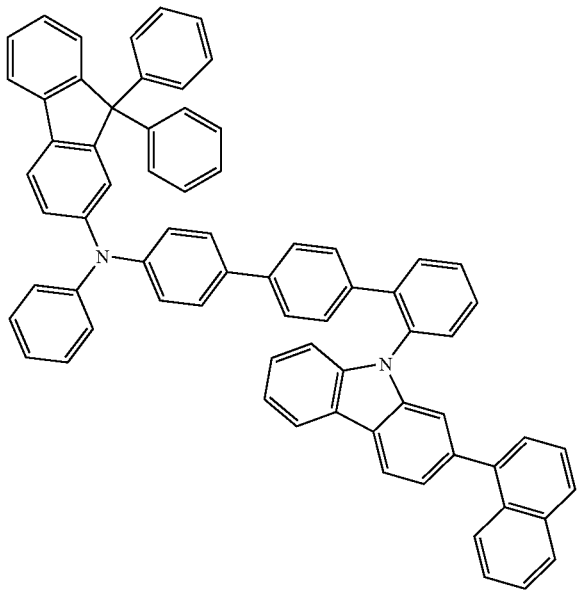
A4-11

A4-12
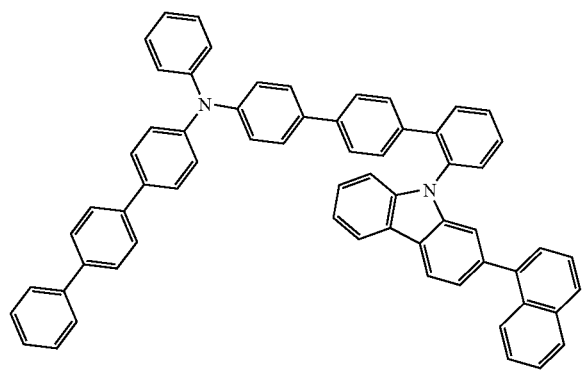
A4-16
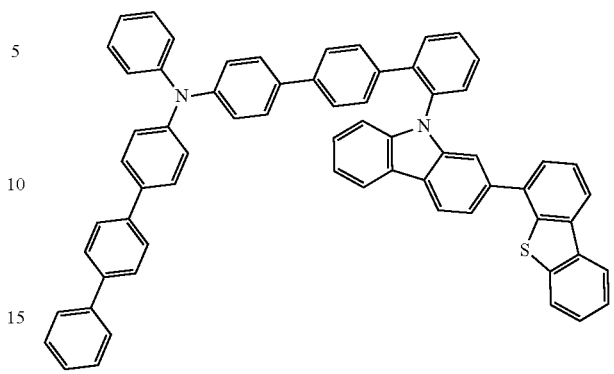
A4-13
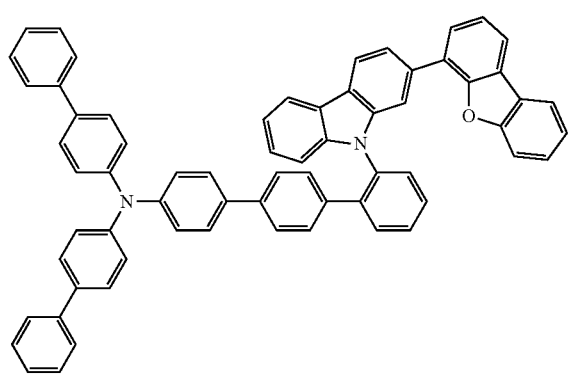
A4-17
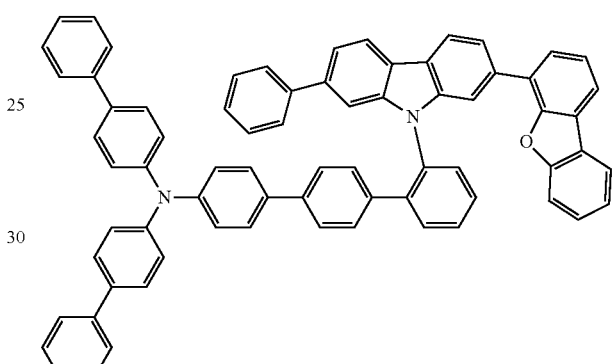
A4-14
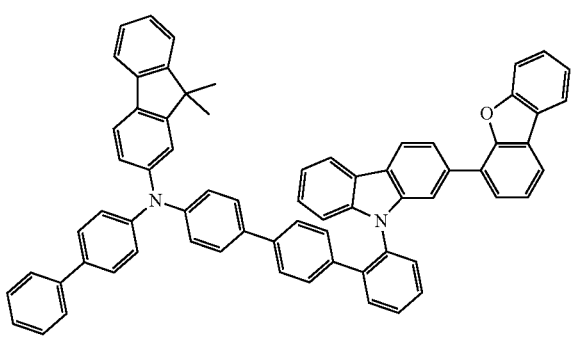
A4-18
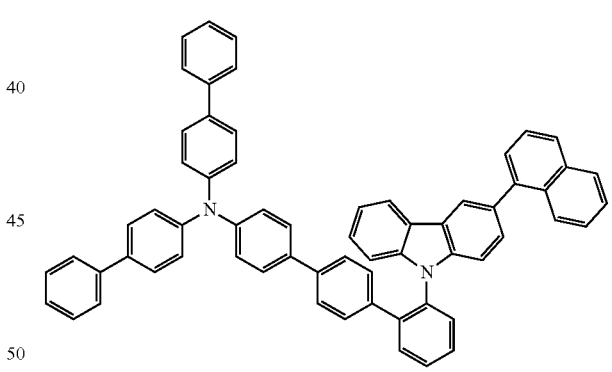
A4-15
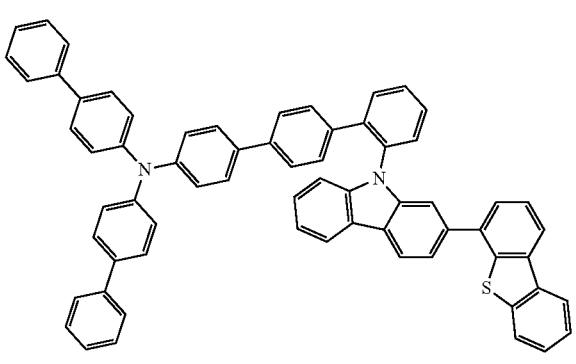
A4-19
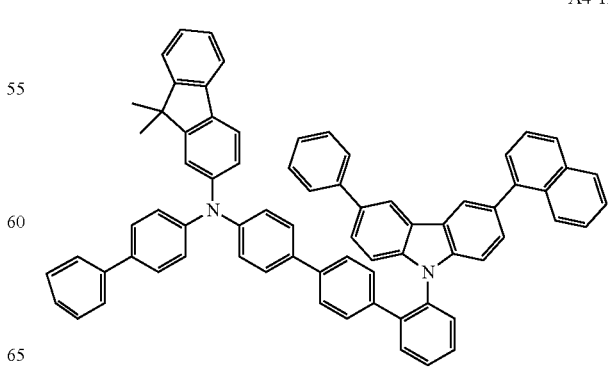

A-20
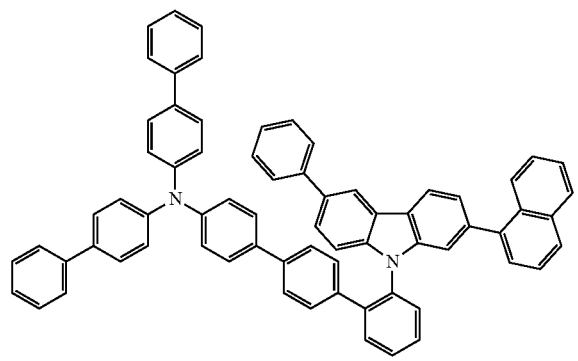
A4-21
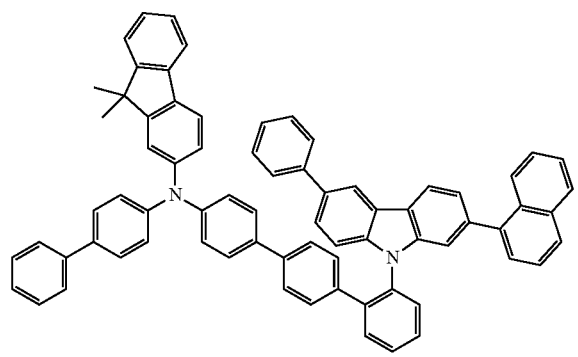
A4-22
A4-23
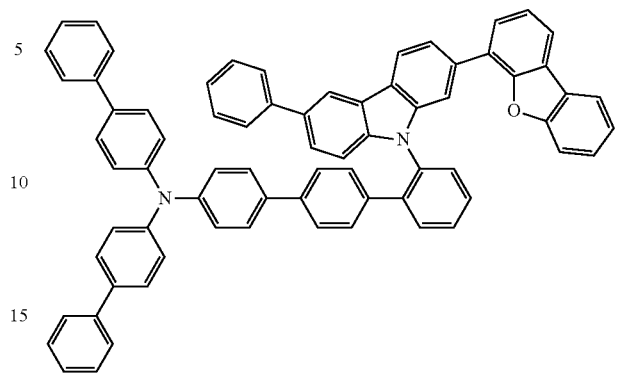
A4-24
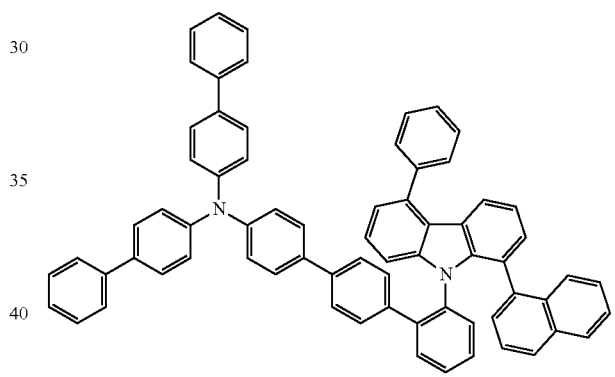
A4-25

A4-26
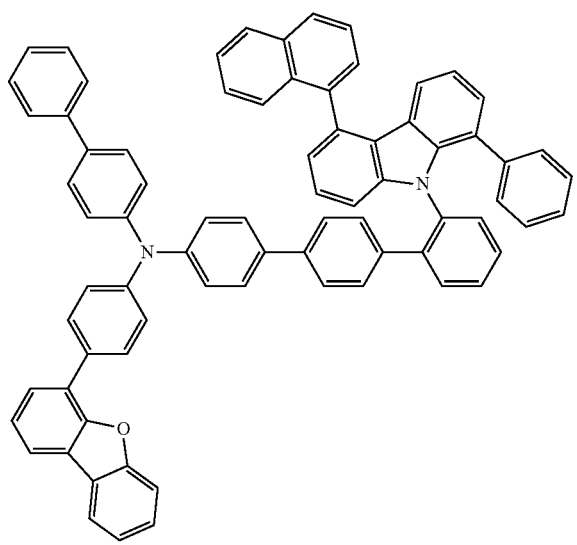
A4-30
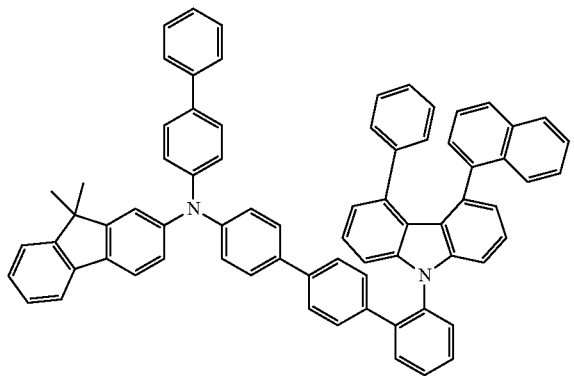
A4-27
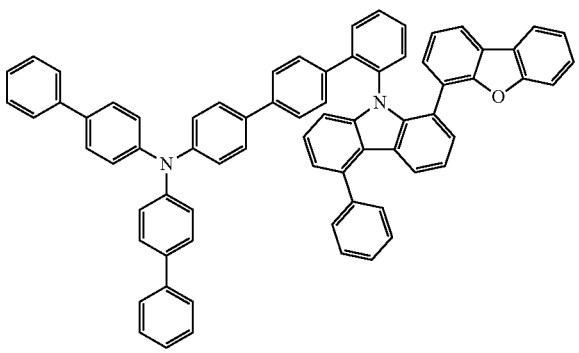
A4-30
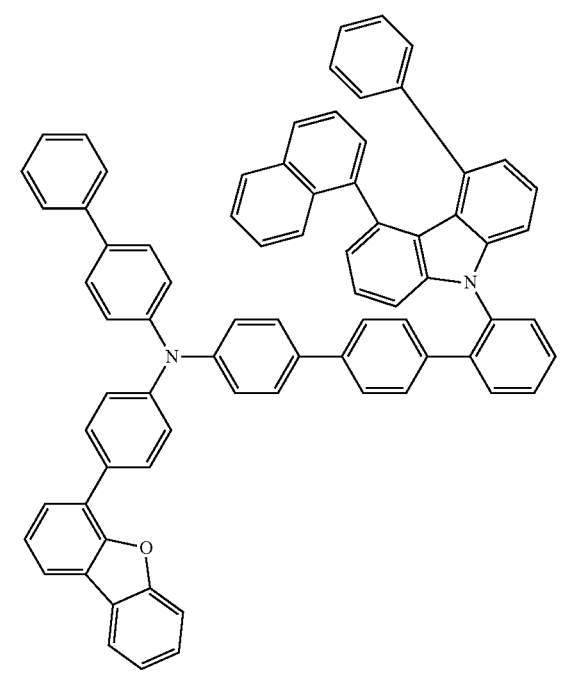
A4-28
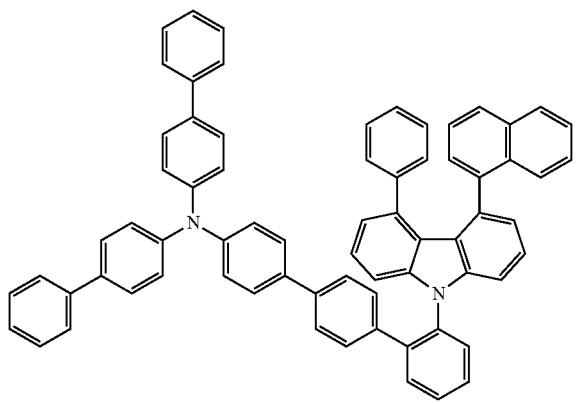
A4-31
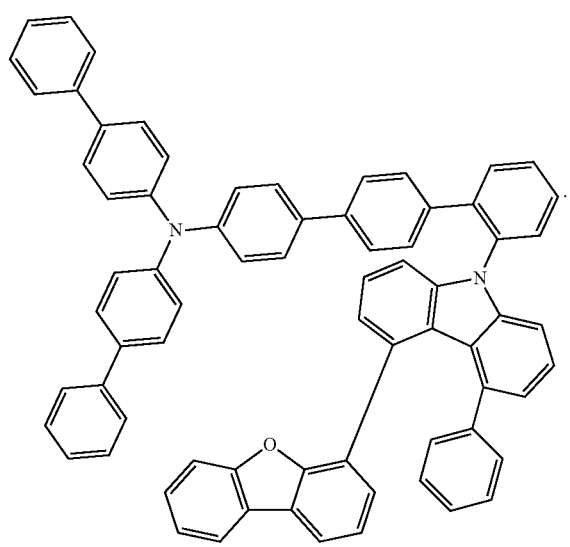

8. An organic optoelectronic diode comprising:
an anode and a cathode; and
at least one organic layer disposed between the anode and the cathode,
wherein the organic layer includes the compound of claim 1.

9. The organic optoelectronic diode of claim 8, wherein the organic layer includes a hole transfer layer, and the hole transfer layer includes the compound.

10. A display device comprising the organic optoelectronic diode of claim 8.

* * * * *